(12) United States Patent
Yao

(10) Patent No.: US 8,603,465 B1
(45) Date of Patent: Dec. 10, 2013

(54) METHODS FOR TREATMENT OF POLYPOSIS

(75) Inventor: Siu-Long Yao, West Windsor, NJ (US)

(73) Assignee: Merck Sharp & Dohme, Corp., Rahway, NJ (US)

( * ) Notice: Subject to any disclaimer, the term of this patent is extended or adjusted under 35 U.S.C. 154(b) by 973 days.

(21) Appl. No.: 11/834,303

(22) Filed: Aug. 6, 2007

Related U.S. Application Data

(60) Provisional application No. 60/835,941, filed on Aug. 7, 2006.

(51) Int. Cl.
*A61K 39/395* (2006.01)

(52) U.S. Cl.
USPC ............. 424/130.1; 424/133.1; 424/138.1; 424/143.1; 424/155.1; 424/174.1; 530/350; 530/387.1; 530/387.3; 530/387.7; 530/388.22; 530/388.8

(58) Field of Classification Search
USPC .......... 424/130.1, 133.1, 138.1, 143.1, 155.1, 424/174.1; 530/387.1, 387.3, 387.7, 530/388.22, 388.8, 389.1, 389.7
See application file for complete search history.

(56) References Cited

U.S. PATENT DOCUMENTS

| | | |
|---|---|---|
| 7,217,796 B2 | 5/2007 | Wang et al. |
| 2004/0018191 A1 | 1/2004 | Wang et al. |
| 2006/0233810 A1 * | 10/2006 | Wang et al. ............... 424/155.1 |

OTHER PUBLICATIONS

Stancoviski et al. (Proceedings of the National Academy of Science USA. 1991; 88: 8691-8695).*
Matsunaka et al (Mol Cancer Ther. Feb. 2010;9(2):419-28).*
Miyamato et al. (Clin Cancer Res. May 1, 2005;11(9):3494-502).*
Cui et al., "Loss of IGF2 imprinting: a potential marker of colorectal cancer risk". Science. Mar. 14, 2003;299(5613):1753-5.
Hassan et al., "Insulin-like growth factor II supply modifies growth of intestinal adenoma in Apc(Min/+) mice". Cancer Res. Feb. 15, 2000;60(4):1070-6.
Jacoby et al., "The cyclooxygenase-2 inhibitor celecoxib is a potent preventive and therapeutic agent in the min mouse model of adenomatous polyposis". Cancer Res. Sep. 15, 2000;60(18):5040-4.
Sakatani et al., "Loss of imprinting of Igf2 alters intestinal maturation and tumorgenesis in mice", Science. Mar. 25, 2005;307(5717):1976-8.

* cited by examiner

*Primary Examiner* — Stephen Rawlings

(57) ABSTRACT

The present invention relates to method for treating medical disorders mediated by mutations in the APC gene by administering an IGF1R inhibitor. Such disorders include, for example, familial adenomatous polyposis (FAP).

11 Claims, No Drawings

METHODS FOR TREATMENT OF POLYPOSIS

This application claims the benefit of U.S. provisional patent application No. 60/835,941, filed Aug. 7, 2006; which is herein incorporated by reference in its entirety.

FIELD OF THE INVENTION

The present invention relates to methods for treating diseases mediated by the APC gene, such as familial adenomatous polyposis.

BACKGROUND OF THE INVENTION

Gardner Syndrome, Turcot Syndrome, familial adenomatous polyposis (FAP) and attenuated FAP are diseases that have been liked to the APC gene. APC is located on the long arm of chromosome 5.

Patients with FAP typically develop hundreds to thousands of colon polyps, usually starting in their teens. Essentially all subjects with FAP will develop colorectal cancer from the colon polyps usually by age 40. Patients with FAP often must have the colon, and sometimes the rectum, removed to prevent colon cancer. A less severe variant of FAP is attenuated FAP.

Gardner syndrome, a variant of FAP, is disease typically characterized by gastrointestinal polyps, multiple osteomas, and skin and soft tissue tumors. Cutaneous findings typically include epidermoid cysts, desmoid tumors, and other benign tumors. Polyps have essentially a 100% risk of undergoing malignant transformation.

Turcot Syndrome is a genetic disease typically characterized by polyps in the colon in addition to tumors in the brain. The polyps in the colon tend to become malignant. The brain tumors are also malignant. There are sometimes also skin abnormalities including cafe-au-lait (coffee-with-milk) spots, multiple lipomas (fatty tumors), and multiple scalp basal cell carcinoma (skin cancers of the scalp). Some consider Turcot syndrome to be a variant of FAP.

A study in mice demonstrated a connection between FAP and insulin-like growth factor II (IGF-II) (Hassan et al., Cancer Res. 60:1070-1076 (2000)). In this study, it was demonstrated that mutation of the IGF-II gene attenuated the expression of the adenomatous phenotype of mice with a mutation in the APC gene.

Presently, there are limited treatment options for patients suffering from FAP and other APC-mediated medical disorders. One of the first medications that was found to shrink colon polyps in patients with FAP was an anti-inflammatory medicine called sulindac. Sulindac is a commonly used non-steroidal anti-inflammatory drug (NSAID). Many patients, however, cannot tolerate sulindac (e.g., due to gastrointestinal toxicity) and must discontinue taking it. An arthritis medication called celecoxib was approved by the FDA for the treatment of colon polyps in patients with FAP. Celecoxib, however, is a COX-2 inhibitor, and such medications have been linked recently to heart attacks (see e.g., Mukherjee et al., JAMA. 286:954-959 (2001)). Another routine treatment option is the drastic surgical measure of colectomy.

There clearly remains a need in the art for effective treatments of FAP and other APC-related medical disorders.

SUMMARY OF THE INVENTION

The present invention addresses the need in the art for additional treatments of FAP and other APC-related medical disorders by providing the methods and compositions of the invention as set forth herein.

The present invention comprises a method for treating or preventing an APC-mediated medical disorder in a subject, by administering, to the subject (e.g., a human), a therapeutically effective amount of an IGF1R inhibitor or a pharmaceutical composition thereof. In an embodiment of the invention, the disorder is a member selected from the group consisting of familial adenomatous polyposis (FAP), Gardner syndrome, Turcot syndrome and attenuated familial adenomatous polyposis. In an embodiment of the invention, the inhibitor is one or more members selected from the group consisting of an isolated antibody or antigen-binding fragment thereof that binds specifically to IGF1R (e.g., a monoclonal antibody, a polyclonal antibody, an anti-idiotypic antibody, a chimeric antibody, a bispecific antibody, a humanized antibody, a fully human antibody, a recombinant antibody, a Fab, a F(ab)2, an Fv, a single chain antibody, a dsFv and a linear antibody),

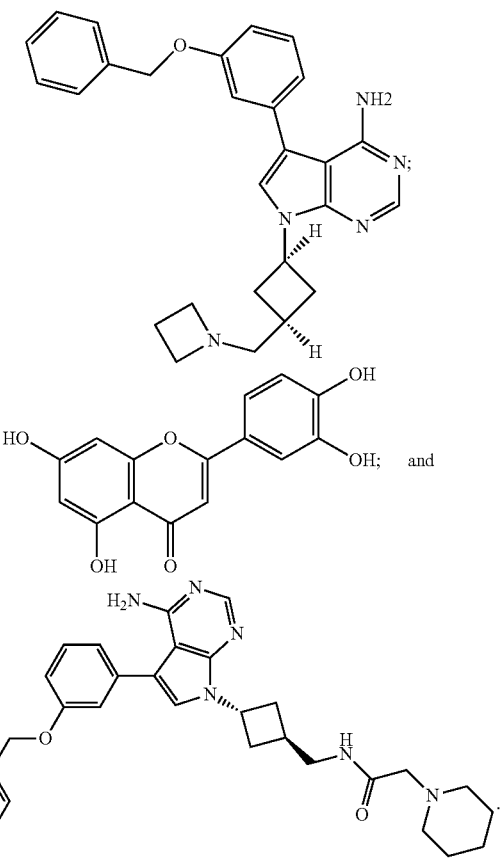

In an embodiment of the invention, the antibody or antigen-binding fragment thereof comprises one or more CDRs from a light chain variable region comprising the amino acid sequence of SEQ ID NO: 2, 4, 6, 8, or 10 and/or one or more CDRs from a heavy chain variable region comprising the amino acid sequence of SEQ ID NO: 10 or 12. In an embodiment of the invention, the antibody is an isolated antibody or antigen binding fragment thereof that binds to IGF1R comprising a light chain immunoglobulin amino acid sequence which comprises CDR-L1 comprising amino acids RASQSIGSSLH (SEQ ID NO: 106), CDR-L2 comprising amino acids YASQSLS (SEQ ID NO: 107) and CDR-L3 comprising amino acids HQSSRLPHT (SEQ ID NO: 108); and/or a heavy chain immunoglobulin amino acid sequence which comprises CDR-H1 comprising amino acids SFAMH (SEQ ID NO: 109) or GFTFSSFAMH (SEQ ID NO: 110), CDR-H2 comprising amino acids VIDTRGATYYADSVKG (SEQ ID NO: 111) and CDR-H3 comprising amino acids LGNFYYGMDV (SEQ ID NO: 112). In an embodiment of the invention, the antibody is an isolated antibody comprising a light chain variable region comprising amino acids 20-128 of SEQ ID NO: 2, 4, 6 or 8 and/or a heavy chain variable region comprising amino acids 20-137 of SEQ ID NO: 10 or 12. In an embodiment of the invention, the antibody or fragment comprises a light chain immunoglobulin variable region linked to a kappa light chain constant region. In an embodiment of the invention, the antibody or fragment comprises a heavy chain immunoglobulin variable region linked to a gamma 1 heavy chain constant region. In an embodiment of the invention, the antibody or fragment comprises a mature heavy chain immunoglobulin encoded by a polynucleotide in plasmid 15H12/19D12 HCA (γ4) which is obtainable from a cell line deposited at the American Type Culture Collection (ATCC) under number PTA-5214; and/or a mature light chain immunoglobulin encoded by a polynucleotide in plasmid 15H12/19D12 LCF (κ) which is obtainable from a cell line deposited at the American Type Culture Collection (ATCC) under number PTA-5220. In an embodiment of the invention, the IGF1R inhibitor is administered to the subject in association with one or more therapeutic procedures, diagnostic procedures or additional therapeutic agents (e.g., a non-steroidal anti-inflammatory agent) e.g., in a single or separate compositions. In an embodiment of the invention, the additional therapeutic agent is one or members selected from the group consisting of any nonsteroidal anti-inflammatory agent (NSAID), any selective COX-2 inhibitor, piroxicam, sulindac, aptosyn (sulindac sulfone), indomethacin, rofecoxib, celecoxib or aspirin, a dietary calcium supplement, a retinoid, a carotenoid, ascorbic acid, α-tocopherol, selenium, folate and methionine. In an embodiment of the invention, the additional therapeutic agent is in a pharmaceutical composition in association with a pharmaceutically acceptable carrier. In an embodiment of the invention, the IGF1R inhibitor is administered to the subject by a parenteral route.

The present invention also provides a composition comprising one or more IGF1R inhibitors (e.g., anti-IGF1R antibodies, e.g., as set forth herein) in association with one or more agents that are suitable for treating or preventing any APC-mediated medical disorder such as FAP including any non-steroidal anti-inflammatory agent, any selective COX-2 inhibitor, piroxicam, sulindac, aptosyn (sulindac sulfone), indomethacin, rofecoxib, celecoxib, aspirin, a dietary calcium supplement, a retinoid, a carotenoid, ascorbic acid, α-tocopherol, selenium, folate and methionine) or a pharmaceutical composition thereof (i.e., comprising a pharmaceutically acceptable carrier).

DETAILED DESCRIPTION OF THE INVENTION

The present invention provides methods for treating or preventing any APC-mediated medical disorder. APC-mediated medical disorders include, for example, FAP, Gardner syndrome, Turcot Syndrome and attenuated FAP. Such disorders are treated by administering an IGF1R inhibitor to the subject optionally in association with a further therapeutic agent (e.g., an anti-inflammatory drug such as an NSAID) or in association with a therapeutic or diagnostic procedure, such as X-ray, colonoscopy or surgery.

The terms "IGF1R", "IGFR1", "Insulin-like Growth Factor Receptor-I" and "Insulin-like Growth Factor Receptor, type I" are well known in the art. Although IGF1R may be from any organism, in an embodiment of the invention it is from an animal, such as a mammal (e.g., mouse, rat, rabbit, sheep or dog) including a human. The nucleotide and amino acid sequence of a typical human IGF1R precursor has the Genbank® Accession No. X04434 or NM_000875. Cleavage of the precursor (e.g., between amino acids 710 and 711) produces an α-subunit and a β-subunit which associate to form a mature receptor.

As stated above, the present invention comprises methods for treating or preventing any APC-mediated disease or medical disorder. Such diseases or disorders include, for example, familial adenomatous polyposis (FAP; also known as familial polyposis coli), Gardner syndrome (see e.g., Gardner et al. Am. J. Hum. Genet. 5:139-47 (1953)), Turcot syndrome and attenuated FAP.

In subjects suffering from familial adenomatous polyposis, colorectal adenomatous polyps typically begin to appear at an average age of 16 years (range 7-36 years). In general, by age 35 years, 95% of individuals have polyps. Once they appear, the polyps generally rapidly increase in number; when colonic expression is fully developed, hundreds to thousands of colonic adenomatous polyps are typically observed. Without colectomy, colon cancer is essentially inevitable. The average age of colon cancer diagnosis in untreated individuals is 39 years (range 34-43 years). Other symptoms that can appear in conjunction with FAP are gastric polyps, adenomatous polyps of the small bowel, and extraintestinal manifestations including osteomas, dental abnormalities (e.g., unerupted teeth, congenital absence of one or more teeth, supernumerary teeth, dentigerous cysts, and odontomas), congenital hypertrophy of the retinal pigment epithelium (CHRPE), benign cutaneous lesions, desmoid tumors, adrenal masses and extracolonic cancers (e.g., small bowel, stomach, pancreas, thyroid, central nervous system, liver, bile ducts and adrenal glands).

Individuals with Gardner syndrome (GS) typically suffer from the colonic adenomatous polyposis of classic FAP with osteomas, and soft tissue tumors. Osteomas are typically found on the mandible and skull, although any bone of the body may be involved. Epidermoid cysts occur on any cutaneous surface and are mainly of cosmetic concern, as they do not appear to have malignant potential.

Individual suffering from Turcot syndrome typically exhibit colonic adenomatous polyposis of classic FAP and CNS tumors such as medulloblastoma. The risk of CNS tumors is substantially increased in persons with FAP generally, although the absolute risk is only approximately 1%.

Attenuated FAP (AFAP) is typically characterized by a significant risk for colon cancer, but fewer colonic polyps (average of 30) than classic FAP. Polyps tend to be found more proximally in the colon than in classic FAP. The average age of colon cancer diagnosis in individuals with AFAP is age 50-55 years—10-15 years later than in those with classic FAP, but earlier than that seen in individuals with sporadically occurring colon cancer. Upper gastrointestinal polyps and cancers may be seen in individuals with AFAP and, although the extraintestinal manifestations of FAP may be present, CHRPE lesions and desmoid tumors are rare.

IGF1R Inhibitors

The present invention comprises methods for treating or preventing any APC-mediated medical disorder such as FAP, in a subject, by administering one or more IGF1R inhibitors to the subject.

The term "IGF1R inhibitor" includes any substance that decreases the expression, ligand binding, kinase activity or any other biological or biochemical activity (e.g., promotion of cellular growth) of IGF1R that will elicit a biological or medical response of a tissue, system or subject that is being sought by the administrator (such as a researcher, doctor or veterinarian) which includes any measurable alleviation of the signs, symptoms and/or clinical indicia of an APC-mediated medical disorder (e.g., FAP). An IGF1R inhibitor can be a small organic or inorganic molecule, or a large molecule such as a polypeptide, an antibody, an antigen-binding fragment of an antibody, a polymer or a nucleic acid.

In an embodiment of the invention, an IGF1R inhibitor that is administered to a patient in a method according to the invention is any isolated anti-insulin-like growth factor receptor-1 (IGF1R) antibody or antigen-binding fragment thereof (e.g., monoclonal antibodies (e.g., fully human monoclonal antibodies), polyclonal antibodies, bispecific antibodies, Fab antibody fragments, F(ab)$_2$ antibody fragments, Fv antibody fragments (e.g., VH or VL), linear antibodies, single chain Fv antibody fragments, dsFv antibody fragments, humanized antibodies, chimeric antibodies or anti-idiotypic antibodies) such as any of those disclosed in any of Burtrum et. al Cancer Research 63:8912-8921 (2003); in French Patent Applications FR2834990, FR2834991 and FR2834900 and in PCT Application Publication Nos. WO 03/100008; WO 03/59951; WO 04/71529; WO 03/106621; WO 04/83248; WO 04/87756 and WO 02/53596.

In an embodiment of the invention, an IGF1R inhibitor that is administered to a patient in a method according to the invention is an isolated anti-insulin-like growth factor receptor-1 (IGF1R) antibody or antigen-binding fragment thereof comprising a mature or unprocessed 19D12/15H12 Light Chain-C, D, E or F and/or a mature 19D12/15H12 heavy chain-A or B. In an embodiment of the invention, an IGF1R inhibitor that is administered to a patient in a method according to the invention is an isolated antibody that specifically binds to IGF1R that comprises one or more complementarity determining regions (CDRs) of 19D12/15H12 Light Chain-C, D, E or F and/or 19D12/15H12 heavy chain-A or B (e.g., all 3 light chain CDRs and all 3 heavy chain CDRs).

The amino acid and nucleotide sequences of the 19D12/15H12 antibody chains are shown below. Dotted, underscored type indicates the signal peptide. Solid underscored type indicates the CDRs. Plain type indicates the framework regions. Mature fragments lack the signal peptide. Such sequences are also disclosed in published U.S. patent application no. US 2004/0018191 and in published international patent application no. WO 03/100008; each of which is herein incorporated by reference in its entirety.

Modified 19D12/15H12 Light Chain-C (SEQ ID NO: 1)

ATG TCG CCA TCA CAA CTC ATT GGG TTT CTG CTG CTC TGG GTT CCA GCC TCC

AGG GGT GAA ATT GTG CTG ACT CAG AGC CCA GAC TCT CTG TCT GTG ACT CCA

GGC GAG AGA GTC ACC ATC ACC TGC CGG GCC AGT CAG AGC ATT GGT AGT AGC

TTA CAC TGG TAC CAG CAG AAA CCA GGT CAG TCT CCA AAG CTT CTC ATC AAG

TAT GCA TCC CAG TCC CTC TCA GGG GTC CCC TCG AGG TTC AGT GGC AGT GGA

TCT GGG ACA GAT TTC ACC CTC ACC ATC AGT AGC CTC GAG GCT GAA GAT GCT

GCA GCG TAT TAC TGT CAT CAG AGT AGT CGT TTA CCT CAC ACT TTC GGC CAA

GGG ACC AAG GTG GAG ATC AAA CGT ACG (SEQ ID NO: 2)

M S P S Q L I G F L L L W V P A S

R G E I V L T Q S P D S L S V T P

G E R V T I T C R A S Q S I G S S

L H W Y Q Q K P G Q S P K L L I K

Y A S Q S L S G V P S R F S G S G

S G T D F T L T I S S L E A E D A

A A Y Y C H Q S S R L P H T F G Q

G T K V E I K R T

Modified 19D12/15H12 Light Chain-D (SEQ ID NO: 3)

ATG TCG CCA TCA CAA CTC ATT GGG TTT CTG CTG CTC TGG GTT CCA GCC TCC

AGG GGT GAA ATT GTG CTG ACT CAG AGC CCA GAC TCT CTG TCT GTG ACT CCA

GGC GAG AGA GTC ACC ATC ACC TGC CGG GCC AGT CAG AGC ATT GGT AGT AGC

TTA CAC TGG TAC CAG CAG AAA CCA GGT CAG TCT CCA AAG CTT CTC ATC AAG

TAT GCA TCC CAG TCC CTC TCA GGG GTC CCC TCG AGG TTC AGT GGC AGT GGA

TCT GGG ACA GAT TTC ACC CTC ACC ATC AGT AGC CTC GAG GCT GAA GAT TTC

GCA GTG TAT TAC TGT CAT CAG AGT AGT CGT TTA CCT CAC ACT TTC GGC CAA

GGG ACC AAG GTG GAG ATC AAA CGT ACG (SEQ ID NO: 4)

M S P S Q L I G F L L L W V P A S
R G E I V L T Q S P D S L S V T P
G E R V T I T C R A S Q S I G S S
L H W Y Q Q K P G Q S P K L L I K
Y A S Q S L S G V P S R F S G S G
S G T D F T L T I S S L E A E D F
A V Y Y C H Q S S R L P H T F G Q
G T K V E I K R T

Modified 19D12/15H12 Light Chain-E (SEQ ID NO: 5)

ATG TCG CCA TCA CAA CTC ATT GGG TTT CTG CTG CTC TGG GTT CCA GCC TCC
AGG GGT GAA ATT GTG CTG ACT CAG AGC CCA GGT ACC CTG TCT GTG TCT CCA
GGC GAG AGA GCC ACC CTC TCC TGC CGG GCC AGT CAG AGC ATT GGT AGT AGC
TTA CAC TGG TAC CAG CAG AAA CCA GGT CAG GCT CCA AGG CTT CTC ATC AAG
TAT GCA TCC CAG TCC CTC TCA GGG ATC CCC GAT AGG TTC AGT GGC AGT GGA
TCT GGG ACA GAT TTC ACC CTC ACC ATC AGT AGA CTG GAG CCT GGA GAT GCT
GCA GCG TAT TAC TGT CAT CAG AGT AGT CGT TTA CCT CAC ACT TTC GGC CAA
GGG ACC AAG GTG GAG ATC AAA CGT ACA (SEQ ID NO: 6)

M S P S Q L I G F L L L W V P A S
R G E I V L T Q S P G T L S V S P
G E R A T L S C R A S Q S I G S S
L H W Y Q Q K P G Q A P R L L I K
Y A S Q S L S G I P D R F S G S G
S G T D F T L T I S R L E P E D A
A A Y Y C H Q S S R L P H T F G Q
G T K V E I K R T

19D12/15H12 Light Chain-F (LCF; SEQ ID NO: 7)

ATG TCG CCA TCA CAA CTC ATT GGG TTT CTG CTG CTC TGG GTT CCA GCC TCC
AGG GGT GAA ATT GTG CTG ACT CAG AGC CCA GGT ACC CTG TCT GTG TCT CCA
GGC GAG AGA GCC ACC CTC TCC TGC CGG GCC AGT CAG AGC ATT GGT AGT AGC
TTA CAC TGG TAC CAG CAG AAA CCA GGT CAG GCT CCA AGG CTT CTC ATC AAG
TAT GCA TCC CAG TCC CTC TCA GGG ATC CCC GAT AGG TTC AGT GGC AGT GGA
TCT GGG ACA GAT TTC ACC CTC ACC ATC AGT AGA CTG GAG CCT GGA GAT TTC
GCA GCG TAT TAC TGT CAT CAG AGT AGT CGT TTA CCT CAC ACT TTC GGC CAA
GGG ACC AAG GTG GAG ATC AAA CGT ACA (SEQ ID NO: 8)

M S P S Q L I G F L L L W V P A S
R G E I V L T Q S P G T L S V S P
G E R A T L S C R A S Q S I G S S
L H W Y Q Q K P G Q A P R L L I K
Y A S Q S L S G I P D R F S G S G
S G T D F T L T I S R L E P E D F
A V Y Y C H Q S S R L P H T F G Q
G T K V E I K R T

19D12/15H12 heavy Chain-A (HCA; SEQ ID NO: 9)

ATG GAG TTT GGG CTG AGC TGG GTT TTC CTT GTT GCT ATA TTA AAA GGT GTC
CAG TGT GAG GTT CAG CTG GTG CAG TCT GGG GGA GGC TTG GTA AAG CCT GGG
GGG TCC CTG AGA CTC TCC TGT GCA GCC TCT GGA TTC ACC TTC AGT AGC TTT
GCT ATG CAC TGG GTT CGC CAG GCT CCA GGA AAA GGT CTG GAG TGG ATA TCA
GTT ATT GAT ACT CGT GGT GCC ACA TAC TAT GCA GAC TCC GTG AAG GGA CGA
TTC ACC ATC TCC AGA GAC AAT GCC AAG AAC TCC TTG TAT CTT CAA ATG AAC
AGC CTG AGA GCC GAG GAC ACT GCT GTG TAT TAC TGT GCA AGA CTG GGG AAC
TTC TAC TAC GGT ATG GAC GTC TGG GGC CAA GGG ACC ACG GTC ACC GTC TCC
TCA (SEQ ID NO: 10)

Met Glu Phe Gly Leu Ser Trp Val Phe Leu Val Ala Ile Leu Lys Gly Val
Gln Cys Glu Val Gln Leu Val Gln Ser Gly Gly Gly Leu Val Lys Pro Gly
Gly Ser Leu Arg Leu Ser Cys Ala Ala Ser Gly Phe Thr Phe Ser Ser Phe
Ala Met His Trp Val Arg Gln Ala Pro Gly Lys Gly Leu Glu Trp Ile Ser
Val Ile Asp Thr Arg Gly Ala Thr Tyr Tyr Ala Asp Ser Val Lys Gly Arg
Phe Thr Ile Ser Arg Asp Asn Ala Lys Asn Ser Leu Tyr Leu Gln Met Asn
Ser Leu Arg Ala Glu Asp Thr Ala Val Tyr Tyr Cys Ala Arg Leu Gly Asn
Phe Tyr Tyr Gly Met Asp Val Trp Gly Gln Gly Thr Thr Val Thr Val Ser
Ser

Modified 19D12/15H12 heavy Chain-B (SEQ ID NO: 11)

ATG GAG TTT GGG CTG AGC TGG GTT TTC CTT GTT GCT ATA TTA AAA GGT GTC
CAG TGT GAG GTT CAG CTG GTG CAG TCT GGG GGA GGC TTG GTA CAG CCC GGG
GGG TCC CTG AGA CTC TCC TGT GCA GCC TCT GGA TTC ACC TTC AGT AGC TTT
GCT ATG CAC TGG GTT CGC CAG GCT CCA GGA AAA GGT CTG GAG TGG ATA TCA
GTT ATT GAT ACT CGT GGT GCC ACA TAC ATA GCA GAC TCC GTG AAG GGC CGA
TTC ACC ATC TCC AGA GAC AAT GCC AAG AAC TCC TTG TAT CTT CAA ATG AAC
AGC CTG CGC GCC GAG GAC ACT GCT GTG TAT TAC TGT GCA AGA CTG GGG AAC
TTC TAC TAC GGT ATG GAC GTC TGG GGC CAA GGG ACC ACG GTC ACC GTC TCC
TCA

-continued (SEQ ID NO: 12)

Met Glu Phe Gly Leu Ser Trp Val Phe Leu Val Ala Ile Leu Lys Gly Val

Gln Cys Glu Val Gln Leu Val Gln Ser Gly Gly Gly Leu Val Gln Pro Gly

Gly Ser Leu Arg Leu Ser Cys Ala Ala Ser Gly Phe Thr Phe Ser Ser Phe

Ala Met His Trp Val Arg Gln Ala Pro Gly Lys Gly Leu Glu Trp Ile Ser

Val Ile Asp Thr Arg Gly Ala Thr Tyr Tyr Ala Asp Ser Val Lys Gly Arg

Phe Thr Ile Ser Arg Asp Asn Ala Lys Asn Ser Leu Tyr Leu Gln Met Asn

Ser Leu Arg Ala Glu Asp Thr Ala Val Tyr Tyr Cys Ala Arg Leu Gly Asn

Phe Tyr Tyr Gly Met Asp Val Trp Gly Gln Gly Thr Thr Val Thr Val Ser

Ser

Cell lines comprising plasmids comprising a CMV promoter operably linked to the 15H12/19D12 LCC, LCD, LCE, LCF or to the 15H12/19D12 HCA or HCB have been deposited at the American Type Culture Collection (ATCC); University Boulevard; Manassas, Va. 20110-2209 on May 21, 2003. The deposit names and the ATCC accession numbers for the cell lines are set forth below:

(1) CMV promoter-15H12/19D12 HCA (γ4)—
Deposit name: "15H12/19D12 HCA (γ4)"
ATCC accession No.: PTA-5214
(2) CMV promoter-15H12/19012 HOB (γ4)—
Deposit name: "15H12/19D12 HCB (γ4)"
ATCC accession No.: PTA-5215
(3) CMV promoter-15H12/19D12 HCA (γ1)—
Deposit name: "15H12/19D12 RCA (γ1)";
ATCC accession No.: PTA-5216
(4) CMV promoter-15H12/19D12 LCC (κ)—
Deposit name: "15H12/19D12 LCC (κ)";
ATCC accession No.: PTA-5217
(5) CMV promoter-15H12/19D12 LCD (κ)—
Deposit name: "15H12/19D12 LCD (κ)";
ATCC accession No.: PTA-5218
(6) CMV promoter-15H12/19D12 LCE (κ)—
Deposit name: "15H12/19D12 LCE (κ)";
ATCC accession No.: PTA-5219
(7) CMV promoter-15H12/19D12 LCF (κ)—
Deposit name: "15H12/19D12 LCF (κ)";
ATCC accession No.: PTA-5220

All restrictions on access to the plasmids deposited in ATCC will be removed upon grant of a patent. In an embodiment of the present invention, an anti-IGF1R antibody or antigen-binding fragment thereof of the invention comprises any of the CDRs or Ig heavy or light chains or variable regions thereof (mature or unprocessed) in any of PTA-5214-PTA-5220. In an embodiment of the invention, the antibody comprises a mature (lacking signal sequence) light chain encoded by the plasmid deposited under number PTA-5220 and a mature (lacking signal sequence) heavy chain encoded by the plasmid deposited under number PTA-5214 or PTA-5216.

In an embodiment of the invention, the anti-IGF1R antibody or antigen-binding fragment thereof comprises one or more (e.g., 3) CDRs taken from 19D12/15H12 LC-C, D, E or F and/or one or more (e.g., 3) CDRs taken from 19D12/15H12 HC-A or B or any other immunoglobulin set forth herein as identified by the Chothia and/or Kabat system for identifying immunoglobulin domains (Chothia et al., J. Mol. Biol. 186:651-663 (1985); Novotny and Haber, Proc. Natl. Acad. Sci. USA 82:4592-4596 (1985) or Kabat, E. A. et al., *Sequences of Proteins of Immunological Interest*, National Institutes of Health, Bethesda, Md., (1987)).

In an embodiment, an antibody that binds "specifically" to human IGF1R binds with Kd of about $1.28 \times 10^{-10}$ M or less by Biacore measurement or with a Kd of about $2.05 \times 10^{-12}$ or less by KinExA measurement.

In an embodiment of the invention, an IGF1R inhibitor that can be administered to a patient in a method according to the invention comprises any light chain immunoglobulin and/or a heavy chain immunoglobulin as set forth in Published International Application No. WO 2002/53596 which is herein incorporated by reference in its entirety. For example, in an embodiment, the antibody comprises a light chain variable region comprising an amino acid sequence selected from the group consisting of SEQ ID NOs: 2, 6, 10, 14, 18, 22, 47 and 51 as set forth in WO 2002/53596 and/or a heavy chain variable region comprising an amino acid sequence selected from the group consisting of SEQ ID NOs: 4, 8, 12, 16, 20, 24, 45 and 49 as set forth in WO 2002/53596.

In an embodiment of the invention, an IGF1R inhibitor that can be administered to a patient in a method according to the invention comprises any light chain immunoglobulin and/or a heavy chain immunoglobulin as set forth in Published International Application No. WO 2003/59951 which is herein incorporated by reference in its entirety. For example, in an embodiment, the antibody comprises a light chain variable region comprising an amino acid sequence selected from the group consisting of SEQ ID NOs: 54, 61 and 65 as set forth in WO 2003/59951 and/or a heavy chain variable region comprising an amino acid sequence selected from the group consisting of SEQ ID NOs: 69, 75, 79 and 83 as set forth in WO 2003/59951.

In an embodiment of the invention, an IGF1R inhibitor that can be administered to a patient in a method according to the invention comprises any light chain immunoglobulin and/or a heavy chain immunoglobulin as set forth in Published International Application No. WO 2004/83248 which is herein incorporated by reference in its entirety. For example, in an embodiment, the antibody comprises a light chain variable region comprising an amino acid sequence selected from the group consisting of SEQ ID NOs: 109, 111, 113, 115, 117, 119, 121, 123, 125, 127, 129, 131, 133, 135, 137, 139, 141 and 143 as set forth in WO 2004/83248 and/or a heavy chain variable region comprising an amino acid sequence selected from the group consisting of SEQ ID NOs: 108, 110, 112, 114, 116, 118, 120, 122, 124, 126, 128, 130, 132, 134, 136, 138, 140 and 142 as set forth in WO 2004183248.

In an embodiment of the invention, an IGF1R inhibitor that can be administered to a patient in a method according to the invention comprises any light chain immunoglobulin and/or a heavy chain immunoglobulin as set forth in Published International Application No. WO 2003/106621 which is herein incorporated by reference in its entirety. For example, in an embodiment, the antibody comprises a light chain variable region comprising an amino acid sequence selected from the group consisting of SEQ ID NOs: 8-12, 58-69, 82-86, 90, 94, 96, 98, as set forth in WO 2003/106621 and/or a heavy chain variable region comprising an amino acid sequence selected from the group consisting of SEQ ID NOs: 7, 13, 70-81, 87, 88, 92 as set forth in WO 2003/106621.

In an embodiment of the invention, an IGF1R inhibitor that can be administered to a patient in a method according to the invention comprises any light chain immunoglobulin and/or a heavy chain immunoglobulin as set forth in Published International Application No. WO 2004/87756 which is herein incorporated by reference in its entirety. For example, in an embodiment, the antibody comprises a light chain variable region comprising an amino acid sequence of SEQ ID NO: 2 as set forth in WO 2004/87756 and/or a heavy chain variable region comprising an amino acid sequence of SEQ ID NO: 1 as set forth in WO 2004/87756.

Furthermore, the scope of the present invention comprises any antibody or antibody fragment comprising one or more CDRs and/or framework regions of any of the light chain immunoglobulin or heavy chain immunoglobulins set forth in WO 2002/53596; WO 2003/59951; WO 2004/83248; WO 2003/106621 or WO 2004/87756 as identified by any of the methods set forth in Chothia et al., J. Mol. Biol. 186:651-663 (1985); Novotny and Haber, Proc. Natl. Acad. Sci. USA 82:4592-4596 (1985) or Kabat, E. A. et al., *Sequences of Proteins of Immunological Interest*, National Institutes of Health, Bethesda, Md., (1987)).

In an embodiment of the invention, anti-IGF1R antibody is produced by a hybridoma that is deposited at the American Type Culture Collection under deposit no. PTA-2792, PTA-2788, PTA-2790, PTA-2791, PTA-2789 or PTA-2793.

In an embodiment of the invention, an anti-IGF1R antibody of the invention comprises an immunoglobulin heavy chain variable region comprising an amino acid sequence selected from the group consisting of:

```
  1  grlgqawrsl  rlscaasgft  fsdyymswir  qapgkglewv  syisssgstr     (SEQ ID NO: 13)

51  dyadsvkgrf  tisrdnakns  lylqmnslra  edtavyycvr  dgvettfyyy 101  yygmdvwgqg  ttvtvssast  kgpsvfplap  csrstsesta  algclvkdyf 151  pepvtvswns  galtsgvhtf  psca 1  vqilesgggl  vqpggslrls  ctasgftfss  yamnwvrqap  gkglewvsai    (SEQ ID NO: 14)

51  sgsggttfya  dsvkgrftis  rdnsrttlyl  qmnslraedt  avyycakdig 101  wsdsyyyyyg  mdvwgqgttv  tvss 1  gpglvkpset  lsltctvsgg  sisnyywswi  rqpagkglew  igriytsgsp    (SEQ ID NO: 15)

51  nynpslksrv  tmsvdtsknq  fslklnsvta  adtavyycav  tifgvviifd 101  ywgqgtlvtv  ss 1  evqllesggg  lvqpggslrl  scaasgftfs  syamswvrqa  pgkglewvsa    (SEQ ID NO: 16)

51  isgsggityy  adsvkgrfti  srdnskntly  lqmnslraed  tavyycakdl 101  gygdfyyyyy  gmdvwgqgtt  vtvss 1  pglvkpsetl  sltctvsggs  issyywswir  qppgkglewi  gyiyysgstn    (SEQ ID NO: 17)

51  ynpslksrvt  isvdtsknqf  slklssvtaa  dtavyycart  ysssfyyygm 101  dvwgqgttvt  vss 1  evqllesggg  lvqpggslrl  scaasgftfs  syamswvrqa  pgkglewvsg    (SEQ ID NO: 18)

51  itgsggstyy  adsvkgrfti  srdnskntly  iqmnslraed  tavyycakdp 101  gttvimswfd  pwgqgtlvtv  ss
```

In an embodiment of the invention, an anti-IGF1R antibody of the invention comprises an immunoglobulin light chain variable region comprising an amino acid sequence selected from the group consisting of:

```
  1  asvgdrvtft  crasqdirrd  lgwyqqkpgk  apkrliyaas  rlgsgvpsrf    (SEQ ID NO: 19)

51  sgsgsgteft  ltisslqped  fatyyclqhn  nyprtfgqgt  eveiirtvaa 101  psvfifppsd  eqlksgtasv  vcllnnfypr  eakvqw 1  diqmtqfpss  isasvgdrvt  itcrasqgir  ndlgwyqqkp  gkapkrliya    (SEQ ID NO: 20)

51  asrlhrgvps  rfsgsgsgte  ftltisslqp  edfatyyclq  hnsypcsfgq 101  gtkleik
```

```
  1 sslsasvgdr vtftcrasqd irrdlgwyqq kpgkapkrli yaasrlqsgv    (SEQ ID NO: 21)
 51 psrfsgsgsg teftltissl qpedfatyyc lqhnnyprtf gqgteveiir 1 diqmtqspss lsasvgdrvt itcrasqgir sdlgwfqqkp gkapkrliya    (SEQ ID NO: 22)
 51 asklhrgvps rfsgsgsgte ftltisriqp edfatyyclq hnsypltfgg
101 gtkveik 1 gdrvtitcra sqsistflnw yqqkpgkapk llihvassiq ggvpsrfsgs    (SEQ ID NO: 23)
 51 gsgtdftlti ssiqpedfat yycqqsynap ltfgggtkve ik 1 ratlscrasq svrgrylawy qqkpgqaprl liygassrat gipdrfsgsg    (SEQ ID NO: 24)
 51 sgtdftltis rlepedfavf ycqqygsspr tfgqgtkvei k
```

In an embodiment of the invention, the anti-IGF1R antibody comprises a light chain immunoglobulin, or a mature fragment thereof (i.e., lacking signal sequence), or variable region thereof, comprising the amino acid sequence of:

```
  1 mdmrvpaqll glllwfpga rcdiqmtqsp sslsasvgdr vtitcrasqg    (SEQ ID NO: 25)
 51 irndlqwyqq kpgkapkrli yaasslqsgv psrfsgsgsg teftltissl
101 qpedfatyyc lqhnsypwtf gqgtkveikr tvaapsvfif ppsdeqlksg
151 tasvvcllnn fypreakvqw kvdnalqsgn sqesvteqds kdstyslsst
201 ltlskadyek hkvyacevth qglsspvtks fnrgec;

1 mdmrvpaqll glllwfpga rcdiqmtqsp sslsasvgdr vtftcrasqd    (SEQ ID NO: 26)
 51 irrdlqwvqq kpgkapkrli yaasrlqsgv psrfsgsgsg teftltissl
101 qpedfatyyc lqhnnyprtf gqgteveiir tvaapsvfif ppsdeqlksg
151 tasvvcllnn fypreakvqw kvdnalqsgn sqesvteqds kdstyslsst
201 ltlskadyek hkvyacevth qglsspvtks fnrgec;

1 mdmrvpaqll glllwfpga rcdiqmtqsp sslsasvgdr vtitcrasqg    (SEQ ID NO: 27)
 51 irndlqwyqq kpgkapkrli yaasslqsgv psrfsgsgsg teftltissl
101 qpedfatyyc lqhnsypytf gqgtkleikr tvaapsvfif ppsdeqlksg
151 tasvvcllnn fypreakvqw kvdnalqsgn sqesvteqds kdstyslsst
201 ltlskadyek hkvyacevth qgisspvtks fnrgec;
or
  1 mdmrvpaqll glllwfpga rcdiqmtqfp sslsasvgdr vtitcrasqg    (SEQ ID NO: 28)
 51 irndlqwyqq kpgkapkrli vaasrlhrgv pprfsgsgsg teftltissl
101 qpedfatyyc lqhnsypcsf gqgtkleikr tvaapsvfif ppsdeqlksg
151 tasvvcllnn fypreakvqw kvdnalqsgn sqesvteqds kdstyslsst
201 ltlskadyek hkvyacevth qglsspvtks fnrgec.
```

In an embodiment of the invention, the signal sequence is amino acids 1-22 of SEQ ID NOs: 25-28. In an embodiment of the invention, the mature variable region is underscored.

In an embodiment of the invention, the anti-IGF1R antibody comprises a heavy chain immunoglobulin or a mature fragment thereof (i.e., lacking signal sequence), or a variable region thereof, comprising the amino acid sequence of:

```
  1   mefglswvfl vaiikgvqcq vqlvesqqgl vkpqgslrls caasqftfsd   (SEQ ID NO: 29)
 51   yymswirqap gkglewvsyi sssqstiyya dsvkgrftis rdnaknslyl
101   qmnslraedt avyycarvlr flewllyyyy yyqmdvwqqq ttvtvssast
151   kgpsvfplap csrstsesta algclvkdyf pepvtvswns galtsgvhtf
201   pavlqssgly slssvvtvps snfgtqtytc nvdhkpsntk vdktverkcc
251   vecppcpapp vagpsvflfp pkpkdtlmis rtpevtcvvv dvshedpevq
301   fnwyvdgvev hnaktkpree qfnstfrvvs vltvvhqdwl ngkeykckvs
351   nkglpapiek tisktkgqpr epqvytlpps reemtknqvs ltclvkgfyp
401   sdiavewesn gqpennykttt ppmldsdgsf flyskltvdk srwqqgnvfs
451   csvmhealhn hytqkslsls pgk;

1   mefglswvfl vaiikgvqcq aqlvesqqgl vkpqgslrls caasqftfsd   (SEQ ID NO: 30)
 51   yymswirqap gkglewvsyi sssgstrdya dsvkgrftis rdnaknslyl
101   qmnslrsedt avyycvrdqv ettfyyyyyq mdvwqqgttv tvssastkgp
151   svfplapcsr stsestaalg clvkdyfpep vtvswnsgal tsgvhtfpav
201   lgssglysls svvtvpssnf gtqtytcnvd hkpsntkvdk tverkccvec
251   ppcpappvag psvflfppkp kdtlmisrtp evtcvvvdvs hedpevqfnw
301   yvdgvevhna ktkpreeqfn stfrvvsvlt vvhqdwlngk eykckvsnkg
351   lpapiektis ktkgqprepq vytlppsree mtknqvsltc lvkgfypsdi
401   avewesngqp ennykttppm ldsdgsffly skltvdksrw qqgnvfscsv
451   mhealhnhyt qkslslspgk;

1   mefglswlfl vailkgvqce vqllesqqgl vqpqgslrls caasqftfss   (SEQ ID NO: 31)
 51   yamswvrqap gkglewvsai sgsggstyya dsvkgrftis rdnskntlyl
101   qmnslraedt avyycakgys sqwyyyyyyq mdvwqqgttv tvssastkgp
151   svfplapcsr stsestaalg clvkdyfpep vtvswnsgal tsgvhtfpav
201   lqssglysls svvtvpssnf gtqtytcnvd hkpsntkvdk tverkccvec
251   ppcpappvag psvflfppkp kdtlmisrtp evtcvvvdvs hedpevqfnw
301   yvdgvevhna ktkpreeqfn stfrvvsvlt vvhqdwlngk eykckvsnkg
351   lpapiektis ktkgqprepq vytlppsree mtknqvsltc lvkgfypsdi
401   avewesngqp ennykttppm ldsdgsffly skltvdksrw qqgnvfscsv
451   mhealhnhyt gkslslspgk;
      or 1   mefglswlfl vailkgvqce vqllesqggl vqpggslrls ctasqftfss   (SEQ ID NO: 32)
 51   yamnwvrqap gkglewvsai sqsqqttfya dsvkgrftis rdnsrttlyl
101   qmnslraedt avyycakdlg wsdsyyyyyq mdvwqqgttv tvssastkgp
151   svfplapcsr stsestaalg clvkdyfpep vtvswnsgal tsgvhtfpav
201   lqssglysls svvtvpssnf gtqtytcnvd hkpsntkvdk tverkccvec
251   ppcpappvag psvflfppkp kdtlmisrtp evtcvvvdvs hedpevqfnw
```

```
301  yvdgvevhna  ktkpreeqfn  stfrvvsvlt  vvhqdwlngk  eykckvsnkg 351  lpapiektis  ktkgqprepq  vytlppsree  mtknqvsltc  lvkgfypsdi 401  avewesngqp  ennykttppm  ldsdgsffly  skltvdksrw  gqgnvfscsv 451  mhealhnhyt  qkslslspgk.
```

In an embodiment of the invention, the signal sequence is amino adds 1-19 of SEQ ID NOs: 29-32. In an embodiment of the invention, the mature variable region is underscored.

In an embodiment of the invention, the anti-IGF1R antibody comprises a light chain variable region comprising the amino acid sequence of any of SEQ ID NOs: 19-24 paired with a heavy chain variable region comprising an amino acid sequence of any of SEQ ID NOs: 13-18, respectively. In an embodiment of the invention, the anti-IGF1R antibody comprises a mature light chain variable region comprising an amino acid sequence of any of SEQ ID NOs: 25 or 26 paired with a heavy chain variable region comprising an amino acid sequence of any of SEQ ID NOs: 29 or 30. In an embodiment of the invention, the anti-IGF1R antibody comprises a mature light chain variable region comprising an amino acid sequence of any of SEQ ID NOs: 27 or 28 paired with a heavy chain variable region comprising an amino acid sequence of any of SEQ ID NOs: 31 or 32.

In an embodiment of the invention, an anti-IGF1R antibody of the invention comprises an immunoglobulin heavy chain or mature fragment or variable region of 2.12.1 fx (SEQ ID NO: 33) (in an embodiment of the invention, the leader sequence is underscored):

```
  1  mefqlswvfl  vaiikqvacq  vqlvesgggl  vkpggslrls  caasgftfsd 51  yymswirqap  gkglewvsyi  sssgstrdya  dsvkgrftis  rdnaknslyl 101  qmnslraedt  avyycardgv  ettfyyyyg   mdvwgqgttv  tvssastkgp 151  svfplapcsr  stsestaalg  clvkdyfpep  vtvswnsgal  tsavhtfpav 201  lqssglysls  svvtvpssnf  gtqtytcnvd  hkpsntkvdk  tverkccvec 251  ppcpappvag  psvflfppkp  kdtlmisrtp  evtcvvvdvs  hedpevqfnw 301  yvdgvevhna  ktkpreeqfn  stfrvvsvlt  vvhqdwlngk  eykckvsnkg 351  lpapiektis  ktkgqprepq  vytlppsree  mtknqvsltc  lvkgfypsdi 401  avewesngqp  ennykttppm  ldsdgsffly  skltvdksrw  qqgnvfscsv 451  mhealhnhyt  gkslslspgk
```

In an embodiment of the invention, an anti-IGF1R antibody of the invention comprises mature immunoglobulin heavy chain variable region 2.12.1 fx (amino acids 20-144 or SEQ ID NO: 33; SEQ ID NO: 34):

```
q  vqlvesgggl  vkpggslrls  caasgftfsd  yymswirqap gkglewvsyi  sssgstrdya  dsvkgrftis  rdnaknslyl qmnslraedt  avyycardgv  ettfyyyyg   mdvwgqgttv  tvss
```

In an embodiment of the invention, an anti-IGF1R antibody of the invention comprises an immunoglobulin light chain or mature fragment or variable region 2.12.1 fx (SEQ ID NO: 35) (in an embodiment of the invention, the leader sequence is underscored):

```
  1  mdmrvpaqll  qllllwfpga  rcdiqmtqsp  sslsasvgdr  vtitcrasqd 51  irrdlgwyqq  kpgkapkrli  yaasrlqsgv  psrfsgsgsg  teftltissl 101  qpedfatyyc  lqhnnyprtf  gqgtkveikr  tvaapsvfif  ppsdeqlksg 151  tasvvcllnn  fypreakvqw  kvdnalqsgn  sqesvteqds  kdstyslsst 201  ltlskadyek  hkvyacevth  qglsspvtks  fnrgec
```

In an embodiment of the invention, an anti-IGF1R antibody of the invention comprises mature immunoglobulin light chain variable region 2.12.1 fx (amino acids 23-130 of SEQ ID NO: 35; SEQ ID NO: 36):

```
diqmtqsp sslsasvgdr vtitcrasqd irrdlgwyqq kpgkapkrli yaasrlqsgv psrfsgsgsg teftltissl qpedfatyyc lqhnnyprtf gqgtkveikr
```

In an embodiment of the invention, an anti-IGF1R antibody of the invention comprises a humanized 7010 immunoglobulin light chain variable region; version 1 (SEQ ID NO: 37):

```
  1  dvvmtqspls lpvtpgepas iscrssqsiv hsngntylqw ylqkpgqspq 51  lliykvsnrl ygvpdrfsgs gsgtdftlki srveaedvgv yycfqgshvp 101  wtfgqgtkve ik
```

In an embodiment of the invention, an anti-IGF1R antibody of the invention comprises humanized 7010 immunoglobulin light chain variable region; version 2 (SEQ ID NO: 38):

```
  1  divmtqspls lpvtpgepas iscrssqsiv hsngntylqw ylqkpgqspq 51  lliykvsnrl ygvpdrfsgs gsgtdftlki srveaedvgv yycfqgshvp 101  wtfgqgtkve ik
```

In an embodiment of the invention, an anti-IGF1R antibody of the invention comprises a humanized 7010 immunoglobulin heavy chain variable region; version 1 (SEQ ID NO: 39):

```
  1  qvqlqesgpg lvkpsetlsl tctvsgysit ggylwnwirq ppgkglewmg 51  yisydgtnny kpslkdriti srdtsknqfs lklssvtaad tavyycaryg 101  rvffdywgqg tlvtvss
```

In an embodiment of the invention, an anti-IGF1R antibody of the invention comprises the humanized 7010 immunoglobulin heavy chain variable region; version 2 (SEQ ID NO: 40):

```
  1  qvqlqesgpg lvkpsetlsl tctvsgysit ggylwnwirq ppgkglewig 51  yisydgtnny kpslkdrvti srdtsknqfs lklssvtaad tavyycaryg 101  rvffdywgqg tivtvss
```

In an embodiment of the invention, an anti-IGF1R antibody of the invention comprises the humanized 7010 immunoglobulin heavy chain variable region; version 3 (SEQ ID NO: 41):

```
  1  qvqlqesgpg lvkpsetlsl tctvsgysis ggylwnwirq ppgkglewig 51  yisydgtnny kpslkdrvti svdtsknqfs lklssvtaad tavyycaryg 101  rvffdywgqg tlvtvss
```

In an embodiment of the invention, an anti-IGF1R antibody of the invention comprises A12 immunoglobulin heavy chain variable region (SEQ ID NO: 42):

```
  1  evqlvqsgae vkkpgssvkv sckasggtfs syaiswvrqa pgqglewmgg
 51  iipifgtany aqkfqgrvti tadkststay melsslrsed tavyycarap
101  lrflewstqd hyyyyymdvw gkgttvtvss
```

In an embodiment of the invention, an anti-IGF1R antibody of the invention comprises A12 immunoglobulin light chain variable region (SEQ ID NO: 43):

```
  1  sseltqdpav svalgqtvri tcqgdslrsy yaswyqqkpg qapvlviygk
 51  nnrpsgipdr fsgsssgnta sltitgaqae deadyycnsr dnsdnrlifg
101  ggtkltvls
```
or (SEQ ID NO: 105):
```
  1  sseltqdpav svalgqtvri tcqgdslrsy yatwyqqkpg qapilviyge
 51  nkrpsgipdr fsgsssgnta sltitgaqae deadyycksr dgsgqhlvfg
101  ggtkltvlg
```

In an embodiment of the invention, an anti-IGF1R antibody of the invention comprises 1A immunoglobulin heavy chain variable region (SEQ ID NO: 44):

```
  1  evqlvqsggg lvhpggslrl scagsgftfr nyamywvrqa pgkglewvsa
 51  igsgggtyya dsvkgrftis rdnaknslyl qmnslraedm avyycarapn
101  wgsdafdiwg qgtmvtvss
``` optionally including one or more of the following mutations: R30, S30, N31, S31, Y94, H94, D104, E104.

In an embodiment of the invention, an anti-IGF1R antibody of the invention comprises 1A immunoglobulin light chain variable region (SEQ ID NO: 45):

```
  1  digmtqspss lsasvgdrvt itcrasqgis swlawyqqkp ekapksliya
 51  asslqsgvps rfsgsgsgtd ftltisslqp edfatyycqq ynsypptfgp
101  gtkvdik
``` optionally including one or more of the following mutations: P96, I96, P100, Q100, 8103, K103, V104, L104, D105, E105

In an embodiment of the invention, an anti-IGF1R antibody of the invention comprises single chain antibody (fv) 8A1 (SEQ ID NO: 46):

```
  1  evglvqsgae vkkpgeslti sckgpgynff nywigwvrqm pgkglewmgi
 51  iyptdsdtry spsfqgqvti svdksistay lqwsslkasd tamyycarsi
101  rycpggrcys gyygmdvwgq gtmvtvssgg ggsggggsgg ggsseltqdp
151  avsvalgqtv ritcqgdslr syyaswyqqk pgqapvlviy gknnrpsgip
201  drfsgsssgn tasltitgaq aedeadyycn srdssgnhvv fgggtkltvl
251  g
```

In an embodiment of the invention, an anti-IGF1R antibody of the invention comprises single chain antibody (fv) 9A2 (SEQ ID NO: 47):

```
  1  qvqlvqsgae vrkpgasvkv scktsgytfr nydinwvrqa pgqglewmgr
 51  isghygntdh agkfqgrftm tkdtststay melrsltfdd tavyycarsq
101  wnvdywgrgt lvtvssgggg sggggsgggg salnfmltqp hsvsespgkt
151  vtisctrssg siasnyvqwy qqrpgssptt vifednrrps gvpdrfsgsi
201  dtssnsaslt isglktedea dyycqsfdst nlvvfgggtk vtvlg
```

In an embodiment of the invention, an anti-IGF1R antibody of the invention comprises single chain antibody (fv) 11A4 (SEQ ID NO: 48):

```
  1  evgllesggg lvqpggslrl scaasgftfs syamswvrga pgkglewvsa
 51  isgsggstyy adsvkgrfti srdnskntly lgmnslraed tavyycassp
101  yssrwysfdp wgqgtmvtvs sggggsgggg sggggsalsy eltqppsysv
151  spgqtatitc sgddlgnkyv swyqqkpgqs pvlviyqdtk rpsgiperfs
201  gsnsgniatl tisgtgavde adyycqvwdt gtvvfgggtk ltvlg
```

In an embodiment of the invention, an anti-IGF1R antibody of the invention comprises single chain antibody (fv) 7A4 (SEQ ID NO: 49):

```
  1  evglvgsgae vkkpgeslti sckgsgynff nywigwvrgm pgkdlewmgi
 51  iyptdsdtry spsfqgqvti svdksistay lqwsslkasd tamyycarsi
101  rycpggrcys gyygmdvwgq gtmvtvssgg gssggggsgg ggsseltqdp
151  avsvalgqtv ritcrgdslr nyyaswyqqk pgqapvlviy gknnrpsgip
201  drfsgsssgn tasltitgaq aedeadyycn srdssgnhmv fgggtkltvl
251  g
```

In an embodiment of the invention, an anti-IGF1R antibody of the invention comprises single chain antibody (fv) 11A1 (SEQ ID NO: 50):

```
  1  evqlvesggg vvqpgrslrl scaasgftfs dfamhwvrqi pgkglewlsg
 51  lrhdgstayy agsvkgrfti srdnsrntvy lqmnslraed tatyycvtgs
131  gssgphafpv wgkgtlvtvs sggggsgggg sggggsalsy vltqppsasg
151  tpgqrvtisc sgsnsnigty tvnwfqqlpg tapklliysn nqrpsgvpdr
201  fsgsksgtsa slaisglqse deadyycaaw ddslngpvfg ggtkvtvlg
```

In an embodiment of the invention, an anti-IGF1R antibody of the invention comprises single chain antibody (fv) 7A6 (SEC) ID NO: 51)

```
  1  evqlvqsgae vkkpgeslti sckgsgynff nywigwvrqm pgkglewmgi
 51  iyptdsdtry spsfqgqvti svdksistay lqwsslkasd tamyycarsi
101  rycpggrcys gyygmdvwgq gtlvtvssgg ggsggggsgg ggsseltqdp
```

```
151 avsvalgqtv ritcqgdslr syytnwfqqk pgqapllvvy aknkrpsgip 201 drfsgsssgn tasltitgaq aedeadyycn srdssgnhvv fgggtkltvl 251 g
```

In an embodiment of the invention, an anti-IGF1R antibody or an antigen-binding fragment thereof (e.g., a heavy chain or light chain immunoglobulin) of the invention comprises one or more complementarity determining regions (CDR) selected from the group consisting of:

```
                                            (SEQ ID NO: 52)
       sywmh;
                                            (SEQ ID NO: 53)
       einpsngrtnynekfkr;
                                            (SEQ ID NO: 54)
       grpdyygsskwyfdv;
                                            (SEQ ID NO: 55)
       rssqsivhsnvntyle;
                                            (SEQ ID NO: 56)
       kvsnrfs;
       and
                                            (SEQ ID NO: 57)
       fqgshvppt.
```

In an embodiment of the invention, an anti-IGF1R antibody or an antigen-binding fragment thereof of the invention comprises a heavy chain immunoglobulin variable region selected from the group consisting of:

```
                                            (SEQ ID NO: 58)
  1 qvqlvqsgae vvkpgasvkl sckasgytft sywmhyvkqr pgqglewige
 51 inpsngrtny nqkfqgkatl tvdkssstay mqlssltsed savyyfargr
101 pdyygsskwy fdvwgqgttv tvs;
                                            (SEQ ID NO: 59)
  1 qvqfqqsgae lvkpgasvkl sckasgytft sylmhwikqr pgrglewigr
 51 idpnnvvtkf nekfkskatl tvdkpsstay melssltsed savyycarya
101 ycrpmdywgq gttvtvss;
                                            (SEQ ID NO: 60)
  1 qvqlqqsgae lvkpgasvkl sckasgytft sywmhwvkqr pgqglewige
 51 inpsngrtny nekfkrkatl tvdkssstay mqlssltsed savyyfargr
101 pdyygsskwy fdvwgagttv tvs;
                                            (SEQ ID NO: 61)
  1 qvqlqqsgae lmkpgasvki sckatgytfs sfwiewvkqr pghglewige
 51 ilpgsggthy nekfkgkatf tadkssntay mqlssltsed savyycargh
101 syyfydgdyw gqgtsvtvss;
                                            (SEQ ID NO: 62)
  1 qvqlqqpgsv lvrpgasvkl sckasgytft sswihwakqr pgqglewige
 51 ihpnsgntny nekfkgkatl tvdtssstay vdlssltsed savyycarwr
101 ygspyyfdyw gqgttltvss;
                                            (SEQ ID NO: 63)
  1 qvqiqqpgae lvkpgasvkl sckasgytft sywmhwvkqr pgrglewigr
 51 idpnsggtky nekfkskatl tvdkpsstay mqlssltsed savyycaryd
101 yygssyfdyw gqgttltvss;
                                            (SEQ ID NO: 64)
  1 qvqlvqsgae vvkpgasvkl sckasgytft sywmhwvkqr pgqglewige
 51 inpsngrtny nqkfqgkatl tvdkssstay mqlssltsed savyyfargr
101 pdyygsskwy fdvwgqgttv tvs;
                                            (SEQ ID NO: 65)
  1 qvqlqqsgae lvkpgasvkl sckasgytft sywmhwvkqr pgqglewige
 51 inpsngrtny nekfkrkatl tvdkssstay mqlssltsed savyyfargr
101 pdyygsskwy fdvwgagttv tvss;
                                            (SEQ ID NO: 66)
  1 qvqlvqsgae vvkpgasvkl sckasgytft sywmhwvkqr pgqglewige
 51 inpsngrtny nqkfqgkatl tvdkssstay mqlssltsed savyyfargr
101 pdyygsskwy fdvwgqgttv tvss;
                                            (SEQ ID NO: 67)
  1 qvqlqqsgae lvkpgasvkl sckasgytft sywmhwvkqr pgrglewigr
 51 idpnsggtky nekfkskatl tvdkpsstay mqlssltsed savyycaryd
101 yygssyfdyw gqgttvtvss;
                                            (SEQ ID NO: 68)
  1 qiqlqqsgpe lvrpgasvki sckasgytft dyyinwvkqr pgeglewigw
 51 iypgsgntky nekfkgkatl tvdtssstay mqlssltsed savyfcargg
101 kfamdywgqg tsvtvss;
```

-continued

```
                                          (SEQ ID NO: 69)
  1  qvqlqqsgae lvkpgasvkl sckasgytft sywmhwvkqr pgqglewige
 51  inpsngrtny nekfkrkatl tvdkssstay mqlssltsed savyyfargr
101  pdyygsskwy fdvwgagttv tvss;

(SEQ ID NO: 70)
  1  qiqlqqsgpe lvkpgasvki sckasgytft dyyinwmkqk pgqglewigw
 51  idpgsgntky nekfkgkatl tvdtssstay mqlssltsed tavyfcarek
101  ttyyyamdyw gqgtsvtvsa;

(SEQ ID NO: 71)
  1  vqlqqsgael mkpgasvkis ckasgytfsd ywiewvkqrp ghglewigei
 51  lpgsgstnyh erfkgkatft adtssstaym qlnsltseds gvyyclhgny
101  dfdgwgqgtt ltvss;
     and (SEQ ID NO: 72)
  1  qvqllesgae lmkpgasvki sckatgytfs sfwiewvkqr pghglewige
 51  ilpgsggthy nekfkgkatf tadkssntay mqlssltsed savyycargh
101  syyfydgdyw gqgtsvtvss;
``` and/or a light chain immunoglobulin variable region selected from the group consisting of:

```
                                          (SEQ ID NO: 73)
  1  dvlmtqipvs lpvslgdgas iscrssqiiv hnngntylew ylqkpgqspq
 51  lliykvsnrf sgvpdrfsgs gsgtdftlki srveaedlgv yycfqgshvp
101  ftfgsgtkle ikr;

(SEQ ID NO: 74)
  1  dvlmtqtpls lpvsigdpas iscrssqsiv hsnvntylew ylqkpgqspk
 51  lliykvsnrf sgvpdrfsgs gagtdftlri srveaedlgi yycfqgshvp
101  ptfgggtkle ikr;

(SEQ ID NO: 75)
  1  dvlmtqfpls lpvslgdpas iscrssqsiv hsnvntylew ylqkpgqspr
 51  lliykvsnrf sgvpdrfsgs gagtdftlri srveaedlgi yycfqgshvp
101  ptfgggtkle ikr;

(SEQ ID NO: 76)
  1  dvlmtqtpls lpvslgdpas iscrssgsiv hsnvntylew ylqkpgqspk
 51  lliykvsnrf sgvpdrfsgs gagtdftlri srveaedlgi yycfqgshvp
101  ptfgggtkle ikr;
                                          (SEQ ID NO: 77)
  1  dvlmtqtpls lpvslgdpas iscrssgsiv hsnvntylew ylqkpgqspr
 51  lliykvsnrf sgvpdrfsgs gagtdftlri srveaedlgi yycfqgshvp
101  ptfgggtkle ikr;
                                          (SEQ ID NO: 78)
  1  dvlmtqtpls lpvslgdqas iscrssgxiv hsngntylew ylqkpgqspk
 51  lliykvsnrf sgvpdrfsgs gsgtdftlki srveaedlgv yycfqgshvp
101  xtfgggtkle ikr;
                                          (SEQ ID NO: 79)
  1  dvvmtqtpls lpvslgdpas iscrssqsiv hsnvntylew ylqkpgqspk
 51  lliykvsnrf sgvpdrfsgs gagtdftlri srveaedlgi yycfqgshvp
101  ptfgggtkle ikr;

(SEQ ID NO: 80)
  1  dvvmtqtpls lpvslgdpas iscrssgsiv hsnvntylew ylqkpgqspr
 51  lliykvsnrf sgvpdrfsgs gagtdftlri srveaedlgi yycfqgshvp
101  ptfgggtkle ikr;

(SEQ ID NO: 81)
  1  dvlmtqtpls lpvslgdpas iscrssqsiv hsnvntylew ylqkpgqspr
 51  lliykvsnrf sgvpdrfsgs gagtdftlri srveaedlgi yycfqgshvp
101  ptfgggtkle ikr;

(SEQ ID NO: 82)
  1  dvlmtqipvs lpvslgdqas iscrssqiiv hnngntylew ylgkpgqspg
 51  lliykvsnrf sgvpdrfsgs gsgtdftlki srveaedlgv yycfqgshvp
101  ftfgsgtkle ikr;

(SEQ ID NO: 83)
  1  dvlmtqtpis lpvslgdgas iscrfsqsiv hsngntylew ylqksgqspk
 51  lliykvsnrf sgvpdrfsgs gsgtdftlki srveaedlgv yycfqgshvp
101  rtfgggtkle ikr;
```

-continued (SEQ ID NO: 84)
```
  1 dvlmtqtpls lpvslgdqas iscrssqsiv hsnvntylew ylqkpgqspk
 51 lliykvsnrf sgvpdrfsgs gsgtdftlri srveaedigi yycfqgshvp
101 ptfgggtkle ikr;
```

(SEQ ID NO: 85)
```
  1 dvvmtqtpls lpvslgdpas iscrssqsiv hsnvntylew ylqkpgqspk
 51 lliykvsnrf sgvpdrfsgs gagtdftlri srveaedlgi yycfqgshvp
101 ptfgggtkle ikr;
```

(SEQ ID NO: 86)
```
  1 elvmtqtpls lpvslgdpas iscrssqtiv hsngdtyldw flqkpgqspk
 51 lliykvsnrf sgvpdrfsgs gsgtdftlki srveaedlgv yycfqgshvp
101 ptfgggtkle ikr;
```

(SEQ ID NO: 87)
```
  1 dvlmtqtpls lpvslgdpas iscrssgsiv hsnvntylew ylqkpgqspk
 51 lliykvsnrf sgvpdrfsgs gagtdftlri srveaedlgi yycfqgshvp
101 ptfgggtkle ikr;
```

(SEQ ID NO: 88)
```
  1 dvvmtqtpls lpvslgdpas iscrssqsiv hsnvntylew ylqkpgqspr
 51 lliykvsnrf sgvpdrfsgs gagtdftlri srveaedlgi yycfqgshvp
101 ptfgggtkle ikr;
```

(SEQ ID NO: 89)
```
  1 dvlmtqtpvs lsvslgdgas iscrssqsiv hstgntylew ylqkpgqspk
 51 lliykisnrf sgvpdrfsgs gsgtdftlki srveaedlgv yycfqashap
101 rtfgggtkle ikr;
```

(SEQ ID NO: 90)
```
  1 dvlmtqtpls lpvslgdpas isckssqsiv hssgntyfew ylqkpgqspk
 51 lliykvsnrf sgvpdrfsgs gsgtdftlki srveaedlgv yycfqgship
101 ftfgsgtkle ikr;
```

(SEQ ID NO: 91)
```
  1 dieltqtpls lpvslgdqas iscrssqsiv hsngntylew ylqkpgqspk
 51 lliykvsnrf sgvpdrfsgs gsgtdftlki srveaedlgv yycfqgshvp
101 ytfgggtkle ikr;
```

(SEQ ID NO: 92)
```
  1 dvlmtqtpls lpvslgdqas iscrssqsiv hsnvntylew ylqkpgqspk
 51 lliykvsnrf sgvpdrfsgs gsgtdftlki srveaedlgi yycfqgshvp
101 ptfgggtkle ikr;
```

(SEQ ID NO: 93)
```
  1 dvvmtqtpls lpvslgdgas iscrssqsiv hsnvntylew ylqkpgqspr
 51 lliykvsnrf sgvpdrfsgs gagtdftlri srveaedlgi yycfqgshvp
101 ptfgggtkle ikr;
```

(SEQ ID NO: 94)
```
  1 dvlmtqtpls lpvslgdqas iscrssqsiv hsnvntylew ylqkpgqspk
 51 lliykvsnrf sgvpdrfsgs gsgtdftlri srveaedlgi yycfqgshvp
101 ptfgggtkle ikr;
```

(SEQ ID NO: 95)
```
  1 dvvmtqtpls lpvslgdpas iscrssqsiv hsnvntylew ylqkpgqspk
 51 lliykvsnrf sgvpdrfsgs gagtdftlri srveaedlgi yycfqgshvp
101 ptfgggtkle ikr;
```

(SEQ ID NO: 96)
```
  1 dvlmtqtpls lpvslgdqas iscrsnqtil lsdgdtylew ylqkpgqspk
 51 lliykvsnrf sgvpdrfsgs gsgtdftlki srveaedlgv yycfqgshvp
101 ptfgggtkle ikr;
```

(SEQ ID NO: 97)
```
  1 dvlmtqtpls lpvslgdqas iscrssqtiv hsngntylew ylqkpgqspk
 51 lliykvtnrf sgvpdrfsgs gsgtdftlki srveaedlgv yycfqgthap
101 ytfgggtkle ikr;
    and
```

(SEQ ID NO: 98)
```
  1 dvlmtqtpls lpvslgdqas iscrssqsiv hsngntylew ylqkpgqspk
 51 lliysissrf sgvpdrfsgs gsgtdftlki srvgaedlgv yycfqgshvp
101 ytfgggtkle ikr.
```

The scope of the present invention includes methods wherein a patient is administered an anti-insulin-like growth factor receptor-1 (IGF1R) antibody wherein the variable region of the antibody is linked to any immunoglobulin constant region. In an embodiment, the light chain variable region is linked to a K chain constant region. In an embodiment, the heavy chain variable region is linked to a γ1, γ2, γ3 or γ4 chain constant region. Any of the immunoglobulin variable regions set forth herein, in embodiments of the invention, can be linked to any of the foregoing constant regions.

In an embodiment of the invention, a linear antibody is an antibody fragment as described in Zapata et al. Protein Eng. 8(10):1057-1062 (1995). Briefly, these fragments comprise a pair of tandem Fd segments (VH-CH1-VH-CH1) which form a pair of antigen-binding regions. Linear antibodies can be bispecific or monospecific.

In an embodiment of the invention, single-chain Fv or sFv antibody fragments comprise the VH and VL domains of an antibody, wherein these domains are present in a single polypeptide chain. Generally, the Fv polypeptide further comprises a polypeptide linker between the VH and VL domains which enables the sFv to form the desired structure for antigen binding. For a review of sFv see Pluckthun in The Pharmacology of Monoclonal Antibodies, vol. 113, Rosenburg and Moore eds. Springer-Verlag, New York, pp. 269-315 (1994).

In an embodiment of the invention, an immunoliposome is a liposome including an anti-IGF1R antibody or antigen-binding fragment thereof. Liposomes containing the antibody or fragment can be prepared by methods known in the art, such as described in Epstein et al., Proc. Natl. Acad. Sci. USA, 82:3688 (1985); Hwang et al., Proc. Natl. Acad. Sci. USA, 77:4030 (1980); and U.S. Pat. Nos. 4,485,045 and 4,544,545. Liposomes with enhanced circulation time are disclosed in U.S. Pat. No. 5,013,556. Other useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab fragments of an anti-IGF1R antibody can be conjugated to the liposomes as described in Martin et al. J. Biol. Chem. 257: 286-288 (1982) via a disulfide interchange reaction.

In an embodiment of the invention, a bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai, et al., (1990) Clin. Exp. Immunol. 79: 315-321, Kostelny, et al., (1992) J. Immunol. 148:1547-1553. In addition, bispecific antibodies may be formed as "diabodies" (Holliger, et al., (1993) PNAS USA 90:6444-6448) or as "Janusins" (Traunecker, et al., (1991) EMBO J. 10:3655-3659 and Traunecker, et al., (1992) Int. J. Cancer Suppl. 7:51-52).

In an embodiment of the invention, a chimeric antibody is an antibody which comprises a variable region of the present invention fused or chimerized with an antibody region (e.g., constant region) from another, non-human species (e.g., mouse, horse, rabbit, dog, cow, chicken).

In an embodiment of the invention, a disulfide stabilized Fv fragment or dsFv is an anti-IGF1R antibody or antigen-binding fragment thereof comprising a variable heavy chain (VH) and a variable light chain (VL) which are linked by a disulfide bridge.

In an embodiment of the invention, an antigen-binding fragment is a F(ab)₂ fragments which may be produced by enzymatic cleavage of an IgG by, for example, pepsin; or a Fab fragment that may be produced by, for example, reduction of F(ab)₂ with dithiothreitol or mercaptoethylamine. In an embodiment of the invention, a Fab fragment is a VL-CL chain appended to a VH-CH1 chain by a disulfide bridge. In an embodiment of the invention, a F(ab)₂ fragment is two Fab fragments which, in turn, are appended by two disulfide bridges. The Fab portion of an F(ab)₂ molecule includes a portion of the Fc region between which disulfide bridges are located.

In an embodiment of the invention, an FV fragment is a VL or VH region of an antibody.

In an embodiment of the invention, an anti-IGFR1 antibody or antigen-binding fragment thereof is conjugated to a chemical moiety. In an embodiment of the invention, the chemical moiety is a polymer which increases the half-life of the antibody or antigen-binding fragment thereof in the body of a subject. Suitable polymers include, but are not limited to, polyethylene glycol (PEG) (e.g., PEG with a molecular weight of 2 kDa, 5 kDa, 10 kDa, 12 kDa, 20 kDa, 30 kDa or 40 kDa), dextran and monomethoxypolyethylene glycol (mPEG). Lee, et al., (1999) (Bioconj. Chem. 10:973-981) discloses PEG conjugated single-chain antibodies.

In an embodiment of the invention, an IGF1R inhibitor that is administered to a subject or patient in a method according to the invention is AEW-541 (NVP-AEW-541; NVP-AEW-541-NX-7):

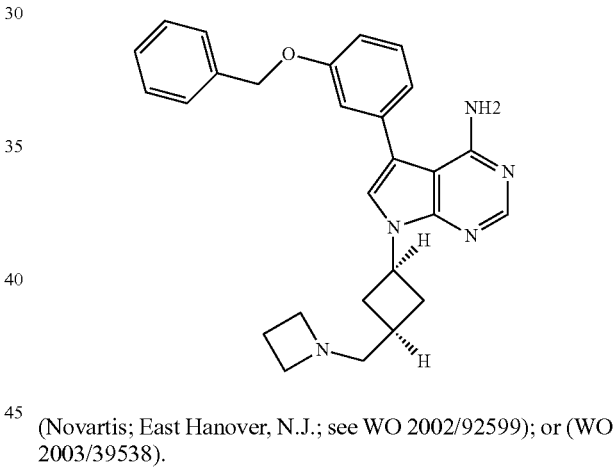

(Novartis; East Hanover, N.J.; see WO 2002/92599); or (WO 2003/39538).

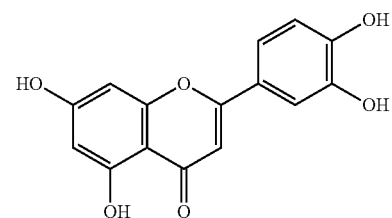 [SMILES: O=c1cc(-c2ccc(O)c(O)c2)oc2cc(O)cc(O)c12]

In an embodiment of the invention, an IGF1R inhibitor that is administered to a patient in a method according to the invention is any IGF1R anti-sense nucleic acid. For example, in an embodiment of the invention, the anti-sense IGF1R nucleic acid is ATL-1101 (Antisense Therapeutics Ltd; Australia). In an embodiment of the invention, the IGF1R anti-sense nucleic acid comprises any of the following nucleotide sequences: 5'-ATCTCTCCGCTTCCTTTC-3' (SEQ ID NO: 99), 5'-ATCTCTCCGCTTCCTTTC-3' (SEQ ID NO: 100), 5"-ATCTCTCCGCTTCCTTTC-3' (SEQ ID NO: 101) or any IGF1R antisense nucleic acid set forth in any of US Published Patent Application No. US20030096769; Published International Application No. WO 2003/100059; Fogarty et al., Antisense Nucleic Acid Drug Dev. 2002 December; 12(6):369-77; White et al, J Invest Dermatol. 2002 June; 118(6): 1003-7; White at al., Antisense Nucleic Acid Drug Dev. 2000 June; 10(3):195-203; or Wraight at al., Nat. Biotechnol. 2000 May; 18(5):521-6.

In an embodiment of the invention, an IGF1R inhibitor that is administered to a patient in a method according to the invention is an anti-IGF-I or II antibody; for example, any antibody disclosed in WO 2003/93317 or EP00492552.

The scope of the present invention includes any kinase inhibitor compound set forth in published international applications WO 2004/030627 or WO 2004/030625. In an embodiment, the kinase inhibitor is (±)-4-[2-(3-chloro-4-fluoro-phenyl)-2-hydroxy-ethylamino]-3-[6-(imidazol-1-yl)-4-methyl-1H-benzimidazol-2-yl]-1H-pyridin-2-one:

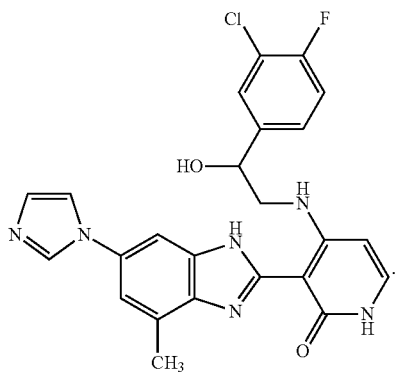 [SMILES: Cc1cc(-n2ccnc2)cc2[nH]c(-c3c(NCC(O)c4ccc(F)c(Cl)c4)cc[nH]c3=O)nc12]

In an embodiment of the invention, the IGR1R inhibitor is a soluble fragment of IGF1R (e.g., amino acids 30-902 of IGF1R) or siRNA (small interfering RNA) against IGF1R.

In an embodiment, IGF1R comprises the amino acid sequence set forth under Genbank® Accession No.: XM_052648 or NM_000612.

The present invention also includes embodiments wherein the patient receives both an IGF1R inhibitor in association with one or more other agents that are useful for the treatment or prevention of any APC-mediated medical disorder such as FAP. In an embodiment, the other agent is an anti-inflammatory agent such as a non-steroidal anti-inflammatory drug. For example, a suitable non-steroidal anti-inflammatory drug is sulindac, aptosyn (sulindac sulfone), indomethacin, rofecoxib, celecoxib or aspirin. In an embodiment of the invention, an IGF1R inhibitor is administered along with dietary calcium supplementation (e.g., 1,250 to 2,000 mg of calcium; e.g., 1500 or 3000 mg/day calcium carbonate) or dietary supplementation with retinoids, carotenoids, ascorbic acid, α-tocopherol, selenium, folate or methionine. The present invention further includes embodiment wherein two or more IGF1R inhibitors are administered in association with one another.

The present invention also comprise embodiments wherein a subject is administered an IGF1R inhibitor to treat or prevent any APC-mediated medical disorder such as FAP in association with a medical therapeutic or diagnostic procedure. For example, an IGF1R inhibitor can be administered in association with colectomy (e.g., total colectomy with mucosal proctectomy with ileo-anal pull through or subtotal colectomy with ileorectal anastomosis), surgical osteoma removal, endoscopic or surgical removal of adenomas (e.g., duodenal adenomas), screening for hepatoblastoma by ultrasound examination, measurement of serum alpha-fetoprotein concentration, sigmoidoscopy, colonoscopy, esophagogastroduodenoscopy or small bowel X-ray.

The term "in association" indicates that the components of the combinations of the invention can be formulated into a single composition for simultaneous delivery or formulated separately into two or more compositions (e.g., a kit). Moreover, compositions and procedures making up combinations of the invention can be administered simultaneously or non-simultaneously. Furthermore, each component of a combination of the invention can be administered to a subject at a different time than when the other component is administered and in any order or permutation; for example, each administration may be given non-simultaneously at several intervals over a given period of time. Moreover, the separate components may be administered to a subject by the same or by a different route (e.g., orally, intravenously, intratumorally).

The scope of the present invention encompasses compositions comprising any IGF1R inhibitor (e.g., as set forth herein) in association with any chemotherapeutic agent (e.g., as set forth herein) known to be useful for treating or preventing any APC-mediated medical disorder such as FAP (e.g., celecoxib) along with pharmaceutical compositions thereof.

Generation of Antibodies

Any suitable method can be used to elicit an antibody or antigen-binding fragment thereof with the desired biologic properties to inhibit IGF1R. It is desirable to prepare monoclonal antibodies (mAbs) from various mammalian hosts, such as mice, rodents, primates, humans, etc. Description of techniques for preparing such monoclonal antibodies may be found in, e.g., Stites, et al. (eds.) BASIC AND CLINICAL IMMUNOLOGY (4th ed.) Lange Medical Publications, Los Altos, Calif., and references cited therein; Harlow and Lane (1988) ANTIBODIES: A LABORATORY MANUAL CSH Press; Goding (1986) MONOCLONAL ANTIBODIES: PRINCIPLES AND PRACTICE (2d ed.) Academic Press, New York, N.Y. Thus, monoclonal antibodies may be obtained by a variety of techniques familiar to researchers skilled in the art. Typically, spleen cells from an animal immunized with a desired antigen are immortalized, commonly by fusion with a myeloma cell. See Kohler and Milstein (1976) Eur. J. Immunol. 6:511-519. Alternative methods of immortalization include transformation with Epstein Barr Virus, oncogenes, or retroviruses, or other methods known in the art. See, e.g., Doyle, at al. (eds. 1994 and periodic supplements) CELL AND TISSUE CULTURE: LABORATORY PROCEDURES, John Wiley and Sons, New York, N.Y. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or an antigen-binding fragment thereof by screening a DNA library from human B cells according, e.g., to the general protocol outlined by Huse, at al. (1989) Science 246:1275-1281. Modified antibodies can be generated, for example, by introducing mutations in DNA encoding an immunoglobulin chain, for example, by use of conventional recombinant biological techniques.

Other suitable techniques involve selection of libraries of antibodies in phage or similar vectors. See, e.g., Huse et al., Science 246:1275-1281 (1989); and Ward al., Nature 341: 544-546 (1989).

In an embodiment of the invention, recombinant immunoglobulins are produced, see Cabilly U.S. Pat. No. 4,816,567; and Queen et al. (1989) Proc. Nat'l Acad. Sci. USA 86:10029-10033; or made in transgenic mice, see Mendez et al. (1997) Nature Genetics 15:146-156. Further methods for producing chimeric, humanized and human antibodies are well known in the art. See, e.g., U.S. Pat. No. 5,530,101, issued to Queen et al, U.S. Pat. No. 5,225,539, issued to Winter et al, U.S. Pat. No. 4,816,397 issued to Boss et al, all of which are incorporated by reference in their entirety.

In an embodiment of the invention, a fully-human monoclonal antibody directed against IGF1R is generated using transgenic mice carrying parts of the human immune system rather than the mouse system. These transgenic mice, which may be referred to, herein, as "HuMAb" mice, contain a human immunoglobulin gene miniloci that encodes unrearranged human heavy (μ and γ) and κ light chain immunoglobulin sequences, together with targeted mutations that inactivate the endogenous μ and κ chain loci (see e.g., Lonberg N et al., (1994) Nature 368(6474): 856-859; Lonberg N, at al., (1994), supra; reviewed in Lonberg, N. (1994) Handbook of Experimental Pharmacology 113:49-101; Lonberg. N., at al., (1995) Intern. Rev. Immunol. 13:65-93, and Harding, F., et al., (1995) Ann. N.Y. Acad. Sci. 764:536-546; in Taylor, L., at al., (1992) Nucleic Acids Research 20:6287-6295; Chen, J., at al., (1993) International Immunology 5: 647-656; Tuaillon, et al., (1993) Proc. Natl. Acad. Sci. USA 90:3720-3724; Choi, et al., (1993) Nature Genetics 4:117-123; Chen, J., et al., (1993) EMBO J. 12: 821-830; Tuaillon, et al., (1994) J. Immunol. 152:2912-2920; Lonberg, et al., (1994) Nature 368(6474): 856-859; Lonberg, N. (1994) Handbook of Experimental Pharmacology 113:49-101; Taylor, L., et al., (1994) International Immunology 6: 579-591; Lonberg, N., et al., (1995) Intern. Rev. Immunol. Vol. 13: 65-93; Harding, F., et al., (1995) Ann. N.Y. Acad. Sci. 764:536-546; Fishwild, D., et al., (1996) Nature Biotechnology 14: 845-851 and Harding, at al., (1995) Annals NY Acad. Sci. 764:536-546; U.S. Pat. Nos. 5,545,806; 5,569,825; 5,625,126; 5,633,425; 5,789,650; 5,877,397; 5,661,016; 5,814,318; 5,874,299; 5,770,429 and 5,545,807; and International Patent Application Publication Nos. WO 98/24884; WO 94/25585; WO 93/12227; WO 92/22645 and WO 92/03918).

A plasmid system set forth in published U.S. patent application no. US2005/0176099 is also useful of the generation of an anti-IGF1R antibody of the present invention (e.g., LCF/HCA).

Dosage

In an embodiment of the invention, an IGF1R inhibitor is administered to a patient at a "therapeutically effective dosage" or "therapeutically effective amount" which inhibits an APC-mediated disease or condition (e.g., FAP) to any extent—e.g., by at least about 20%, 40%, 60% or 80%-100% relative to untreated subjects.

In an embodiment of the invention, the term "therapeutically effective amount" or "therapeutically effective dosage" means that amount or dosage of an IGF1R inhibitor (e.g., an anti-IGF1R antibody or antigen-binding fragment thereof) that will elicit a biological or medical response of a tissue, system, subject or host that is being sought by the administrator (such as a researcher, doctor or veterinarian) which includes any measurable alleviation of the signs, symptoms and/or clinical indicia of an APC-mediated disease (e.g., FAP) and/or the prevention, slowing or halting of progression of FAP to any degree.

A physician or veterinarian having ordinary skill in the art may determine and prescribe the effective amount of IGF1R inhibitor required for an optimal clinical result depending on the circumstances of the particular patient. For example, the physician or veterinarian could start doses of an IGF1R inhibitor employed in the pharmaceutical composition at levels lower than that required in order to achieve the desired therapeutic effect and gradually increase the dosage until the desired effect is achieved. The effectiveness of a given dose or treatment regimen of IGF1R inhibitor can be determined, for example, by consideration of any of several observed clinical indicia. Proper adjustments to dosage and/or regimen can then be made by the clinician so as to reach the best result. For example, a clinician can monitor the responsiveness of an APC-mediated disease (e.g., FAP, Gardner Syndrome or Turcot Syndrome) to a given course of treatment by any appropriate means. For example, responsiveness can be monitored by performing sigmoidoscopy or colonoscopy to visualize the condition of the subject's colon. A clinician can monitor the state of any upper gastrointestinal tract polyps (e.g., in the stomach, duodenum or papilla), in a subject, by way of an upper endoscopic examination (e.g., a forward and a side viewing endoscopic examination). Another monitoring method includes patient interviews to determine the presence and severity of any symptoms associated with FAP, for example, blood in the stool, diarrhea that is not the result of diet or illness, constipation, crampy pain in the abdomen, irregular bowel habits, decrease in the size or caliber of stool, frequent feeling of distention in the abdomen or bowel region (e.g., gas pain, bloating, fullness, with or without cramping), unexplained weight loss, vomiting and lack of energy.

The presence of any of the foregoing symptoms and clinical indicia can also aid a practitioner in identifying a patient with an APC-mediated medical disorder, such as FAP, who is thus in need of a treatment of the present invention.

As stated above, the present invention comprises methods for treatment or prevention of any medical condition mediated by a mutation in the APC gene, for example, FAP, by administration of a "therapeutically effective amount" or "therapeutically effective dose" of an IGF1R inhibitor. In an embodiment of the invention, a therapeutically effective daily amount or dose of IGF1R inhibitor or pharmaceutical composition thereof is administered as two, three, four, five, six or more sub-doses administered separately at appropriate intervals throughout the day. In an embodiment, a "therapeutically effective" dosage or amount of any anti-IGF1R antibody (e.g., 19D12/15H12 LCD/HCB, LCC/HCB or LCF/HCA) is in the range of about 0.3 mg/kg (body weight) to about 20 mg/kg (e.g., 0.5 mg/kg, 0.9 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg or 20 mg/kg) administered, for example, 1 time per week. In an embodiment of the invention, a therapeutically effective dosage or amount of an IGF1R inhibitor or any other chemotherapeutic agent (e.g., as set forth herein) is, whenever possible, as set forth in the *Physicians' Desk Reference* 2003 (Thomson Healthcare; 57$^{th}$ edition (Nov. 1, 2002)) which is herein incorporated by reference or in the scientific literature. For example, in an embodiment of the invention, a therapeutically effective dosage or amount of celecoxib is about 400 mg twice per day taken with food. In an embodiment of the invention, a therapeutically effective dosage or amount of sulindac is about 400 mg per day. In an embodiment of the invention, a therapeutically effective dosage or amount of sulindac sulfone is about 200 mg/day.

Therapeutic Methods and Administration

The term "patient" or "subject" includes any organism, preferably an animal, for example, a mammal (e.g., rat, mouse, dog, cat, rabbit) such as a human. Accordingly, the present invention includes veterinary and non-veterinary methods for treating or preventing an APC-mediated disease.

As stated above, in an embodiment of the invention, where possible, an IGF1R inhibitor or any other chemotherapeutic agent set forth herein (e.g., NSAID) is administered to a patient or subject in accordance with the Physicians' Desk Reference 2003 (Thomson Healthcare; 57th edition (Nov. 1, 2002)) or as set forth herein.

An IGF1R inhibitor and/or an additional therapeutic agent (e.g., an NSAID such as celecoxib) can be administered by an invasive route such as by injection. In an embodiment of the invention, an anti-IGF1R antibody, or pharmaceutical composition thereof, is administered intravenously, subcutaneously, intramuscularly or intraarterially. An embodiment of the invention comprises treating or preventing an APC-mediated medical condition by reconstituting a lyophilized or otherwise desiccated powder containing an IGF1R inhibitor (e.g., a pharmaceutical formulation thereof, e.g., in a glass or plastic vial or container), for example in water, DMSO or buffer, and then administering a therapeutically effective amount of the agent in the reconstituted solution to a subject in need thereof (e.g., a subject suffering from FAP), for example, parenterally (e.g., by injection with a hypodermic needle).

Administration of an IGF1R inhibitor and/or an additional therapeutic agent by a non-invasive route (e.g., orally; for example, in a pill, capsule or tablet) is also within the scope of the present invention.

The scope of the present invention comprises methods wherein the IGF1R inhibitor is administered by the same or by a different route as an additional therapeutic agent (e.g., celecoxib). In an embodiment of the invention, an anti-IGF1R antibody is administered by injection and a second therapeutic agent (e.g., celecoxib) is administered orally.

An IGF1R inhibitor and/or an additional therapeutic agent can be administered with medical devices known in the art. For example, a pharmaceutical composition of the invention (e.g., a pharmaceutical composition comprising an anti-IGF1R antibody) can be administered by injection with a hypodermic needle.

The pharmaceutical compositions of the invention may also be administered with a needleless hypodermic injection device; such as the devices disclosed in U.S. Pat. No. 6,620, 135; 6,096,002; 5,399,163; 5,383,851; 5,312,335; 5,064,413; 4,941,880; 4,790,824 or 4,596,556.

Examples of well-known implants and modules for administering pharmaceutical compositions include: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art Diagnosis of a medical disorder such as FAP, Gardner Syndrome, Turcot Syndrome and Attenuated FAP is within the scope of knowledge commonly held in the art. For example, Gardner Syndrome can be diagnosed using radiological tests which reveal long bone osteomas and subtle defects in the mandible; eye exams that reveal pigmented lesions of the fundus of the eye; and colonoscopies and other invasive tests which reveal the presence of polyps. FAP and AFAP can be diagnosed by screening of the patient's colon for the presence of polyps (e.g., by flexible sigmoidoscopy or colonoscopy) as well as by genetic screening for the presence of a mutated APC gene.

Pharmaceutical Compositions

An IGF1R inhibitor can, in an embodiment of the invention, be incorporated into a pharmaceutical composition, along with a pharmaceutically acceptable carrier, suitable for administration to a subject in vivo is within the scope of the present invention. The scope of the present invention includes pharmaceutical compositions which are suitable to be administered to a subject by any route (e.g., parenteral or non-parenteral) including, for example, oral, ocular, topical, pulmonary (inhalation), intratumoral injection, intravenous injection, subcutaneous injection or intramuscular injection.

For general information concerning formulations, see, e.g., Gilman, et al., (eds.) (1990), *The Pharmacological Bases of Therapeutics,* 8th Ed., Pergamon Press; A. Gennaro (ed.), *Remington's Pharmaceutical Sciences,* 18th Edition, (1990), Mack Publishing Co., Easton, Pa.; Avis, et al., (eds.) (1993) *Pharmaceutical Dosage Forms: Parenteral Medications* Dekker, New York; Lieberman, et al., (eds.) (1990) *Pharmaceutical Dosage Forms: Tablets* Dekker, New York; and Lieberman, et al., (eds.) (1990), *Pharmaceutical Dosage Forms: Disperse Systems* Dekker, New York, Kenneth A. Walters (ed.) (2002) *Dermatological and Transdermal Formulations (Drugs and the Pharmaceutical Sciences),* Vol 119, Marcel Dekker.

Pharmaceutically acceptable carriers are conventional and very well known in the art. Examples include aqueous and nonaqueous carriers, stabilizers, antioxidants, solvents, dispersion media, coatings, antimicrobial agents, buffers, serum proteins, isotonic and absorption delaying agents, and the like that are physiologically compatible. In an embodiment of the invention, the carrier is suitable for injection into a subject's body.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Examples of pharmaceutically-acceptable antioxidants include: water soluble antioxidants such as ascorbic acid, cysteine hydrochloride, sodium bisulfate, sodium metabisulfite, sodium sulfite and the like; and oil-soluble antioxidants such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Prevention of the presence of microorganisms may be ensured both by sterilization procedures, and by the inclusion of various antimicrobial agents such as EDTA, EGTA, paraben, chlorobutanol, phenol sorbic acid, and the like.

Suitable buffers which may be included in the pharmaceutical compositions of the invention include L-histidine-based buffers, phosphate-based buffers (e.g., phosphate buffered saline, pH≅7), sorbate-based buffers or glycine-based buffers.

Serum proteins which are, in an embodiment of the invention, included in the pharmaceutical compositions of the invention include human serum albumin.

Isotonic agents, such as sugars (e.g., sucrose), ethanol, polyalcohols (e.g., glycerol, propylene glycol, liquid polyethylene glycol, mannitol or sorbitol), sodium citrate or sodium chloride (e.g., buffered saline) are, in an embodiment of the invention, included in the pharmaceutical compositions of the invention. In an embodiment of the invention, the sugar, for example, glucose or sucrose is present at a high concentration (e.g., about 10-100 mg/ml, e.g., 50 mg/ml, 60 mg/ml or 70 mg/ml).

Prolonged absorption of an injectable pharmaceutical form may be brought about by the inclusion of agents which delay absorption such as aluminum monostearate and/or gelatin.

Dispersions can also be prepared in glycerol, liquid polyethylene glycols, and mixtures thereof and in oils.

Pharmaceutically acceptable carriers include sterile aqueous solutions or dispersions and sterile powders for the extemporaneous preparation of sterile injectable solutions or dispersions. The use of such media and agents for pharmaceutically active substances is well known in the art.

Sterile injectable solutions comprising an anti-IGF1R antibody can be prepared by incorporating the antibody or antigen-binding fragment thereof in the required amount in an appropriate solvent, optionally with one or a combination of ingredients enumerated above, as required, followed by sterilization microfiltration. Generally, dispersions are prepared by incorporating the antibody into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional, desired ingredient from a previously sterile-filtered solution thereof.

In an embodiment of the invention, an anti-IGF1R antibody or antigen-binding fragment thereof of the invention is in a pharmaceutical formulation comprising a therapeutically effective amount of said antibody or fragment, a buffer and sucrose. For example, in an embodiment of the invention, the buffer is any one of phosphate buffer, citrate buffer, histidine buffer, glycine buffer or acetate buffer. The pharmaceutical formulation can be within any suitable pH range. In an embodiment of the invention, the pH is 5.0, 5.5, 6.0, 7.5, or between about 5.5 and about 6 or between about 5 and about 7.

In an embodiment of the invention, an IGF1R inhibitor and/or other chemotherapeutic agent is orally administered. Pharmaceutical compositions for oral administration contain, in an embodiment of the invention, in addition to the active agent, additives such as starch (e.g., potato, maize or wheat starch or cellulose), starch derivatives (e.g., microcrystalline cellulose or silica), sugars (e.g., lactose), talc, stearate, magnesium carbonate or calcium phosphate. In order to ensure that oral compositions comprising an active agent are well tolerated by the patient's digestive system, mucus formers or resins may be included. It may also be desirable to improve tolerance by formulating the active agent in a capsule which is insoluble in the gastric juices. An exemplary pharmaceutical composition of this invention in the form of a capsule is prepared by filling a standard two-piece hard gelatin capsule with the active agent in powdered form, lactose, talc and magnesium stearate.

Oral administration of immunoglobulins, such as an anti-IGF1R antibody or antigen-binding fragment thereof of the invention, has been described (Foster, et al., (2001) Cochrane Database System rev. 3:CD001816).

In an embodiment of the invention, an anti-IGF1R antibody or antigen-binding fragment thereof of the invention is in a pharmaceutical formulation suitable for injection comprising, at a pH of about 5.5, about 20 mg/ml of the antibody (or any suitable concentration of the antibody); about 2.3 mg/ml of sodium acetate trihydrate; about 0.18 mg/ml of glacial acetic acid; about 70 mg/ml of sucrose and water.

An IGF1R inhibitor or other chemotherapeutic agent may also be administered by inhalation. A suitable pharmaceutical composition for inhalation may be an aerosol. An exemplary pharmaceutical composition for inhalation of an IGF1R inhibitor or other chemotherapeutic agent may include: an aerosol container with a capacity of 15-20 ml comprising the IGF1R inhibitor or other chemotherapeutic agent, a lubricating agent, such as polysorbate 85 or oleic acid, dispersed in a propellant, such as freon, preferably in a combination of 1,2-dichlorotetrafluoroethane and difluorochloromethane. Preferably, the composition is in an appropriate aerosol container adapted for either intranasal or oral inhalation administration.

EXAMPLES

The following information is provided for more clearly describing the present invention and should not be construed to limit the present invention. Any and all of the compositions and methods described below fall within the scope of the present invention.

Example 1

Inhibition of Polyposis in Human IGF1R Knock-in Mice

In this example, the ability of anti-IGF1R antibody 19D12 (LCF/HCA: amino acids 20-128 of SEQ ID NO: 8 and 20-137 of SEQ ID NO: 10) to treat familial adenomatous polyposis (FAP) is established in a mouse model for the disease. The model comprises the $Apc^{Min/+}$ allele which imparts the FAP phenotype. A phenotype that results from the allele is increased development of intestinal adenomas. The Min mutant mouse has an autosomal dominant heterozygous non-sense mutation in the mouse Apc gene (see e.g., Su et al., Science (Wash D.C.) 256: 668-670 (1992)).

The Min mice are also engineered, by a knock-in mutation, to express the human IGF1R gene. Expression of the IGF1R gene, in the Min mouse, allows determination of the ability of an anti-IGF1R antibody to alleviate the FAP phenotype. Antibody-dependent reduction of the incidence of intestinal adenomas in the hIGF1R, $Apc^{Min/+}$ mice indicates that the antibody would be an effective treatment of FAP in humans and other animals.

Twenty eight C57Bl/6J (hIGF1R, $Apc^{Min/+}$) mice are obtained commercially and broken into the following groups (4 per group):

TABLE 1

Organization of Treatment Groups.

| Treatment group | Route and dosing schedule |
|---|---|
| NT | vehicle injection once a week |
| 19D12 (LCF/HCA), 0.02 mg/mouse | i.p. injection once a week |
| 19D12 (LCF/HCA), 0.1 mg/mouse | i.p. injection once a week |
| 19D12 (LCF/HCA), 0.5 mg/mouse | i.p. injection once a week |
| Celecoxib, 150 ppm | in diet |
| Celecoxib, 500 ppm | in diet |
| Celecoxib, 1500 ppm | in diet |

Small intestinal adenomas and colonic adenomas are scored for number and diameter at postnatal day 80. The stomach, small intestine, and colon are dissected free of mesentery and opened along the longitudinal axis. Intestinal contents are cleared with phosphate buffered saline (PBS), and the small intestine is divided into three equal-length segments and laid open with the colon on the absorptive side of Benchkote® (Whatman®). Intestines are fixed in 4% (4 g/100 ml) paraformaldehyde in PBS (24 h) followed by 70% ethanol (v/v). Using a dissecting microscope (×10-30) and calipers, adenoma number and diameter are obtained for the entire length of the small intestine and colon. Adenoma analysis is performed without knowledge of genotype by one person and confirmed independently by another. Small intestine surface area is calculated by summation of the multiples of length of each fixed segment by width, which is measured at the midpoint of each segment. Colon surface area is calculated by multiplying the length of the fixed material from the anorectal junction to the point of insertion of the small intestine, omitting the appendix, by the width at the midpoint. Raw numbers of adenomas observed as well as adenomas per unit of small intestine and colon surface area are calculated.

Mice receiving the 19D12 (LCF/HCA) antibody or celecoxib exhibit a dose-dependent reduction of raw adenoma number as well as adenomas per unit surface area in the small intestine and colon.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, Genbank® Accession Numbers and publications are cited throughout this application, the disclosures of which are incorporated herein by reference in their entireties.

I claim:

1. A method for treating familial adenomatous polyposis, in a subject, comprising administering, to a mammalian subject with familial adenomatous polyposis, a therapeutically effective amount of an isolated antibody or antigen-binding fragment thereof that specifically binds human insulin-like growth factor-1 receptor comprising a light chain immunoglobulin that comprises CDR-L1, CDR-L2 and CDR-L3 of the amino acid sequence set forth in SEQ ID NO: 8; and, a heavy chain immunoglobulin that comprises CDR-H1, CDR-H2 and CDR-H3 of the amino acid sequence set forth in SEQ ID NO: 10 and which reduces the number or surface area of adenomas in the small intestine or colon of the subject.

2. The method of claim 1 wherein the antibody or antigen-binding fragment thereof is an antibody comprising a light chain immunoglobulin that comprises the amino acid sequence set forth in SEQ ID NO: 8; and, a heavy chain immunoglobulin that comprises the amino acid sequence set forth in SEQ ID NO: 10.

3. The method of claim 2 wherein the antibody comprises a light chain immunoglobulin variable region linked to a kappa light chain constant region.

4. The method of claim 3 wherein the antibody or fragment comprises a heavy chain immunoglobulin variable region linked to a gamma 1 heavy chain constant region.

5. The method of claim 4 wherein the antibody is administered to the subject in association with one or more therapeutic procedures, diagnostic procedures or additional chemotherapeutic agents.

6. The method of claim 5 wherein an additional chemotherapeutic agent is one or members selected from the group consisting of piroxicam, sulindac, sulindac sulfone, indomethacin, rofecoxib, celecoxib, aspirin, a dietary calcium supplement, a retinoid, a carotenoid, ascorbic acid, α-tocopherol, selenium, folate and methionine.

7. The method of claim 5 wherein the antibody and additional chemotherapeutic agent are in a single pharmaceutical composition along with a pharmaceutically acceptable carrier.

8. The method of claim 5 wherein the antibody and additional chemotherapeutic agent are in two or more separate pharmaceutical compositions each along with pharmaceutically acceptable carriers.

9. The method of claim 4 wherein the antibody is administered to the subject by a parenteral route.

10. The method of claim 1 wherein the antibody or antigen-binding fragment thereof is a member selected from the group consisting of a monoclonal antibody, a polyclonal antibody, an anti-idiotypic antibody, a chimeric antibody, a bispecific antibody, a humanized antibody, a fully human antibody, a recombinant antibody, a Fab, a F(ab)$_2$, an Fv, a single chain antibody, a dsFv and a linear antibody.

11. The method of claim 4 wherein the subject is human.

* * * * *

UNITED STATES PATENT AND TRADEMARK OFFICE
CERTIFICATE OF CORRECTION

PATENT NO. : 8,603,465 B1
APPLICATION NO. : 11/834303
DATED : December 10, 2013
INVENTOR(S) : Siu-Long Yao Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1018 days.

Signed and Sealed this

Twenty-third Day of May, 2017

Michelle K. Lee
*Director of the United States Patent and Trademark Office*

SEQUENCE LISTING

```
<160> NUMBER OF SEQ ID NOS: 112

<210> SEQ ID NO 1
<211> LENGTH: 384
<212> TYPE: DNA
<213> ORGANISM: Artificial Sequence
<220> FEATURE:
<223> OTHER INFORMATION: Modified 19D12/15H12 Light Chain-C
<220> FEATURE:
<221> NAME/KEY: CDS
<222> LOCATION: (1)..(384)

<400> SEQUENCE: 1 atg tcg cca tca caa ctc att ggg ttt ctg ctg ctc tgg gtt cca gcc      48
Met Ser Pro Ser Gln Leu Ile Gly Phe Leu Leu Leu Trp Val Pro Ala
1               5                   10                  15 tcc agg ggt gaa att gtg ctg act cag agc cca gac tct ctg tct gtg      96
Ser Arg Gly Glu Ile Val Leu Thr Gln Ser Pro Asp Ser Leu Ser Val
                20                  25                  30 act cca ggc gag aga gtc acc atc acc tgc cgg gcc agt cag agc att     144
Thr Pro Gly Glu Arg Val Thr Ile Thr Cys Arg Ala Ser Gln Ser Ile
            35                  40                  45 ggt agt agc tta cac tgg tac cag cag aaa cca ggt cag tct cca aag     192
Gly Ser Ser Leu His Trp Tyr Gln Gln Lys Pro Gly Gln Ser Pro Lys
        50                  55                  60 ctt ctc atc aag tat gca tcc cag tcc ctc tca ggg gtc ccc tcg agg     240
Leu Leu Ile Lys Tyr Ala Ser Gln Ser Leu Ser Gly Val Pro Ser Arg
65                  70                  75                  80 ttc agt ggc agt gga tct ggg aca gat ttc acc ctc acc atc agt agc     288
Phe Ser Gly Ser Gly Ser Gly Thr Asp Phe Thr Leu Thr Ile Ser Ser
                85                  90                  95 ctc gag gct gaa gat gct gca gcg tat tac tgt cat cag agt agt cgt     336
Leu Glu Ala Glu Asp Ala Ala Ala Tyr Tyr Cys His Gln Ser Ser Arg
            100                 105                 110 tta cct cac act ttc ggc caa ggg acc aag gtg gag atc aaa cgt acg     384
Leu Pro His Thr Phe Gly Gln Gly Thr Lys Val Glu Ile Lys Arg Thr
        115                 120                 125
```

<210> SEQ ID NO 2
<211> LENGTH: 128
<212> TYPE: PRT
<213> ORGANISM: Artificial Sequence
<220> FEATURE:
<223> OTHER INFORMATION: Synthetic Construct

<400> SEQUENCE: 2

```
Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Asp Ser Leu Ser Val
            20                  25                  30

Thr Pro Gly Glu Arg Val Thr Ile Thr Cys Arg Ala Ser Gln Ser Ile
        35                  40                  45

Gly Ser Ser Leu His Trp Tyr Gln Gln Lys Pro Gly Gln Ser Pro Lys
    50                  55                  60

Leu Leu Ile Lys Tyr Ala Ser Gln Ser Leu Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Glu Ala Glu Asp Ala Ala Ala Tyr Tyr Cys His Gln Ser Ser Arg
            100                 105                 110

Leu Pro His Thr Phe Gly Gln Gly Thr Lys Val Glu Ile Lys Arg Thr
        115                 120                 125
```

<210> SEQ ID NO 3
<211> LENGTH: 384
<212> TYPE: DNA
<213> ORGANISM: Artificial Sequence
<220> FEATURE:
<223> OTHER INFORMATION: Modified 19D12/15H12 Light Chain-D
<220> FEATURE:
<221> NAME/KEY: CDS
<222> LOCATION: (1)..(384)

<400> SEQUENCE: 3

```
atg tcg cca tca caa ctc att ggg ttt ctg ctg ctc tgg gtt cca gcc      48
Met Ser Pro Ser Gln Leu Ile Gly Phe Leu Leu Leu Trp Val Pro Ala
1               5                   10                  15 tcc agg ggt gaa att gtg ctg act cag agc cca gac tct ctg tct gtg     96
Ser Arg Gly Glu Ile Val Leu Thr Gln Ser Pro Asp Ser Leu Ser Val
            20                  25                  30 act cca ggc gag aga gtc acc atc acc tgc cgg gcc agt cag agc att    144
Thr Pro Gly Glu Arg Val Thr Ile Thr Cys Arg Ala Ser Gln Ser Ile
        35                  40                  45 ggt agt agc tta cac tgg tac cag cag aaa cca ggt cag tct cca aag    192
Gly Ser Ser Leu His Trp Tyr Gln Gln Lys Pro Gly Gln Ser Pro Lys
    50                  55                  60 ctt ctc atc aag tat gca tcc cag tcc ctc tca ggg gtc ccc tcg agg    240
Leu Leu Ile Lys Tyr Ala Ser Gln Ser Leu Ser Gly Val Pro Ser Arg
65                  70                  75                  80 ttc agt ggc agt gga tct ggg aca gat ttc acc ctc acc atc agt agc    288
Phe Ser Gly Ser Gly Ser Gly Thr Asp Phe Thr Leu Thr Ile Ser Ser
                85                  90                  95 ctc gag gct gaa gat ttc gca gtg tat tac tgt cat cag agt agt cgt    336
Leu Glu Ala Glu Asp Phe Ala Val Tyr Tyr Cys His Gln Ser Ser Arg
            100                 105                 110 tta cct cac act ttc ggc caa ggg acc aag gtg gag atc aaa cgt acg    384
Leu Pro His Thr Phe Gly Gln Gly Thr Lys Val Glu Ile Lys Arg Thr
        115                 120                 125
```

```
<210> SEQ ID NO 4
<211> LENGTH: 128
<212> TYPE: PRT
<213> ORGANISM: Artificial Sequence
<220> FEATURE:
<223> OTHER INFORMATION: Synthetic Construct

<400> SEQUENCE: 4

Met Ser Pro Ser Gln Leu Ile Gly Phe Leu Leu Leu Trp Val Pro Ala
 1               5                   10                  15

Ser Arg Gly Glu Ile Val Leu Thr Gln Ser Pro Asp Ser Leu Ser Val
            20                  25                  30

Thr Pro Gly Glu Arg Val Thr Ile Thr Cys Arg Ala Ser Gln Ser Ile
        35                  40                  45

Gly Ser Ser Leu His Trp Tyr Gln Gln Lys Pro Gly Gln Ser Pro Lys
    50                  55                  60

Leu Leu Ile Lys Tyr Ala Ser Gln Ser Leu Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Glu Ala Glu Asp Phe Ala Val Tyr Tyr Cys His Gln Ser Ser Arg
            100                 105                 110

Leu Pro His Thr Phe Gly Gln Gly Thr Lys Val Glu Ile Lys Arg Thr
        115                 120                 125

<210> SEQ ID NO 5
<211> LENGTH: 384
<212> TYPE: DNA
<213> ORGANISM: Artificial Sequence
<220> FEATURE:
<223> OTHER INFORMATION: Modified 19D12/15H12 Light Chain-E
<220> FEATURE:
<221> NAME/KEY: CDS
<222> LOCATION: (1)..(384)

<400> SEQUENCE: 5 atg tcg cca tca caa ctc att ggg ttt ctg ctg ctc tgg gtt cca gcc       48
Met Ser Pro Ser Gln Leu Ile Gly Phe Leu Leu Leu Trp Val Pro Ala
 1               5                   10                  15 tcc agg ggt gaa att gtg ctg act cag agc cca ggt acc ctg tct gtg       96
Ser Arg Gly Glu Ile Val Leu Thr Gln Ser Pro Gly Thr Leu Ser Val
            20                  25                  30 tct cca ggc gag aga gcc acc ctc tcc tgc cgg gcc agt cag agc att      144
Ser Pro Gly Glu Arg Ala Thr Leu Ser Cys Arg Ala Ser Gln Ser Ile
        35                  40                  45 ggt agt agc tta cac tgg tac cag cag aaa cca ggt cag gct cca agg      192
Gly Ser Ser Leu His Trp Tyr Gln Gln Lys Pro Gly Gln Ala Pro Arg
    50                  55                  60 ctt ctc atc aag tat gca tcc cag tcc ctc tca ggg atc ccc gat agg      240
Leu Leu Ile Lys Tyr Ala Ser Gln Ser Leu Ser Gly Ile Pro Asp Arg
65                  70                  75                  80 ttc agt ggc agt gga tct ggg aca gat ttc acc ctc acc atc agt aga      288
Phe Ser Gly Ser Gly Ser Gly Thr Asp Phe Thr Leu Thr Ile Ser Arg
                85                  90                  95 ctg gag cct gaa gat gct gca gcg tat tac tgt cat cag agt agt cgt      336
Leu Glu Pro Glu Asp Ala Ala Ala Tyr Tyr Cys His Gln Ser Ser Arg
            100                 105                 110 tta cct cac act ttc ggc caa ggg acc aag gtg gag atc aaa cgt aca      384
Leu Pro His Thr Phe Gly Gln Gly Thr Lys Val Glu Ile Lys Arg Thr
        115                 120                 125
```

<210> SEQ ID NO 6
<211> LENGTH: 128
<212> TYPE: PRT
<213> ORGANISM: Artificial Sequence
<220> FEATURE:
<223> OTHER INFORMATION: Synthetic Construct

<400> SEQUENCE: 6

```
Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Gly Thr Leu Ser Val
            20                  25                  30

Ser Pro Gly Glu Arg Ala Thr Leu Ser Cys Arg Ala Ser Gln Ser Ile
        35                  40                  45

Gly Ser Ser Leu His Trp Tyr Gln Gln Lys Pro Gly Gln Ala Pro Arg
    50                  55                  60

Leu Leu Ile Lys Tyr Ala Ser Gln Ser Leu Ser Gly Ile Pro Asp Arg
65                  70                  75                  80

Phe Ser Gly Ser Gly Ser Gly Thr Asp Phe Thr Leu Thr Ile Ser Arg
                85                  90                  95

Leu Glu Pro Glu Asp Ala Ala Tyr Tyr Cys His Gln Ser Ser Arg
            100                 105                 110

Leu Pro His Thr Phe Gly Gln Gly Thr Lys Val Glu Ile Lys Arg Thr
        115                 120                 125
```

<210> SEQ ID NO 7
<211> LENGTH: 384
<212> TYPE: DNA
<213> ORGANISM: Artificial Sequence
<220> FEATURE:
<223> OTHER INFORMATION: 19D12/15H12 Light Chain-F
<220> FEATURE:
<221> NAME/KEY: CDS
<222> LOCATION: (1)..(384)

<400> SEQUENCE: 7

```
atg tcg cca tca caa ctc att ggg ttt ctg ctg ctc tgg gtt cca gcc      48
Met Ser Pro Ser Gln Leu Ile Gly Phe Leu Leu Leu Trp Val Pro Ala
1               5                   10                  15 tcc agg ggt gaa att gtg ctg act cag agc cca ggt acc ctg tct gtg      96
Ser Arg Gly Glu Ile Val Leu Thr Gln Ser Pro Gly Thr Leu Ser Val
            20                  25                  30 tct cca ggc gag aga gcc acc ctc tcc tgc cgg gcc agt cag agc att     144
Ser Pro Gly Glu Arg Ala Thr Leu Ser Cys Arg Ala Ser Gln Ser Ile
        35                  40                  45 ggt agt agc tta cac tgg tac cag cag aaa cca ggt cag gct cca agg     192
Gly Ser Ser Leu His Trp Tyr Gln Gln Lys Pro Gly Gln Ala Pro Arg
    50                  55                  60 ctt ctc atc aag tat gca tcc cag tcc ctc tca ggg atc ccc gat agg     240
Leu Leu Ile Lys Tyr Ala Ser Gln Ser Leu Ser Gly Ile Pro Asp Arg
65                  70                  75                  80 ttc agt ggc agt gga tct ggg aca gat ttc acc ctc acc atc agt aga     288
Phe Ser Gly Ser Gly Ser Gly Thr Asp Phe Thr Leu Thr Ile Ser Arg
                85                  90                  95 ctg gag cct gaa gat ttc gca gtg tat tac tgt cat cag agt agt cgt     336
Leu Glu Pro Glu Asp Phe Ala Val Tyr Tyr Cys His Gln Ser Ser Arg
            100                 105                 110 tta cct cac act ttc ggc caa ggg acc aag gtg gag atc aaa cgt aca     384
Leu Pro His Thr Phe Gly Gln Gly Thr Lys Val Glu Ile Lys Arg Thr
        115                 120                 125
```

<210> SEQ ID NO 8

```
<211> LENGTH: 128
<212> TYPE: PRT
<213> ORGANISM: Artificial Sequence
<220> FEATURE:
<223> OTHER INFORMATION: Synthetic Construct

<400> SEQUENCE: 8

Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Gly Thr Leu Ser Val
            20                  25                  30

Ser Pro Gly Glu Arg Ala Thr Leu Ser Cys Arg Ala Ser Gln Ser Ile
        35                  40                  45

Gly Ser Ser Leu His Trp Tyr Gln Gln Lys Pro Gly Gln Ala Pro Arg
    50                  55                  60

Leu Leu Ile Lys Tyr Ala Ser Gln Ser Leu Ser Gly Ile Pro Asp Arg
65                  70                  75                  80

Phe Ser Gly Ser Gly Ser Gly Thr Asp Phe Thr Leu Thr Ile Ser Arg
                85                  90                  95

Leu Glu Pro Glu Asp Phe Ala Val Tyr Tyr Cys His Gln Ser Ser Arg
            100                 105                 110

Leu Pro His Thr Phe Gly Gln Gly Thr Lys Val Glu Ile Lys Arg Thr
        115                 120                 125

<210> SEQ ID NO 9
<211> LENGTH: 411
<212> TYPE: DNA
<213> ORGANISM: Artificial Sequence
<220> FEATURE:
<223> OTHER INFORMATION: 19D12/15H12 heavy chain-A
<220> FEATURE:
<221> NAME/KEY: CDS
<222> LOCATION: (1)..(411)

<400> SEQUENCE: 9 atg gag ttt ggg ctg agc tgg gtt ttc ctt gtt gct ata tta aaa ggt     48
Met Glu Phe Gly Leu Ser Trp Val Phe Leu Val Ala Ile Leu Lys Gly
1               5                   10                  15 gtc cag tgt gag gtt cag ctg gtg cag tct ggg gga ggc ttg gta aag     96
Val Gln Cys Glu Val Gln Leu Val Gln Ser Gly Gly Gly Leu Val Lys
            20                  25                  30 cct ggg ggg tcc ctg aga ctc tcc tgt gca gcc tct gga ttc acc ttc    144
Pro Gly Gly Ser Leu Arg Leu Ser Cys Ala Ala Ser Gly Phe Thr Phe
        35                  40                  45 agt agc ttt gct atg cac tgg gtt cgc cag gct cca gga aaa ggt ctg    192
Ser Ser Phe Ala Met His Trp Val Arg Gln Ala Pro Gly Lys Gly Leu
    50                  55                  60 gag tgg ata tca gtt att gat act cgt ggt gcc aca tac tat gca gac    240
Glu Trp Ile Ser Val Ile Asp Thr Arg Gly Ala Thr Tyr Tyr Ala Asp
65                  70                  75                  80 tcc gtg aag ggc cga ttc acc atc tcc aga gac aat gcc aag aac tcc    288
Ser Val Lys Gly Arg Phe Thr Ile Ser Arg Asp Asn Ala Lys Asn Ser
                85                  90                  95 ttg tat ctt caa atg aac agc ctg aga gcc gag gac act gct gtg tat    336
Leu Tyr Leu Gln Met Asn Ser Leu Arg Ala Glu Asp Thr Ala Val Tyr
            100                 105                 110 tac tgt gca aga ctg ggg aac ttc tac tac ggt atg gac gtc tgg ggc    384
Tyr Cys Ala Arg Leu Gly Asn Phe Tyr Tyr Gly Met Asp Val Trp Gly
        115                 120                 125 caa ggg acc acg gtc acc gtc tcc tca                                411
Gln Gly Thr Thr Val Thr Val Ser Ser
        130                 135
```

<210> SEQ ID NO 10
<211> LENGTH: 137
<212> TYPE: PRT
<213> ORGANISM: Artificial Sequence
<220> FEATURE:
<223> OTHER INFORMATION: Synthetic Construct

<400> SEQUENCE: 10

```
Met Glu Phe Gly Leu Ser Trp Val Phe Leu Val Ala Ile Leu Lys Gly
1               5                   10                  15

Val Gln Cys Glu Val Gln Leu Val Gln Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Ser Phe Ala Met His Trp Val Arg Gln Ala Pro Gly Lys Gly Leu
    50                  55                  60

Glu Trp Ile Ser Val Ile Asp Thr Arg Gly Ala Thr Tyr Tyr Ala Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Thr Ala Val Tyr
            100                 105                 110

Tyr Cys Ala Arg Leu Gly Asn Phe Tyr Tyr Gly Met Asp Val Trp Gly
        115                 120                 125

Gln Gly Thr Thr Val Thr Val Ser Ser
    130                 135
```

<210> SEQ ID NO 11
<211> LENGTH: 411
<212> TYPE: DNA
<213> ORGANISM: Artificial Sequence
<220> FEATURE:
<223> OTHER INFORMATION: Modified 19D12/15H12 heavy chain-B
<220> FEATURE:
<221> NAME/KEY: CDS
<222> LOCATION: (1)..(411)

<400> SEQUENCE: 11

```
atg gag ttt ggg ctg agc tgg gtt ttc ctt gtt gct ata tta aaa ggt    48
Met Glu Phe Gly Leu Ser Trp Val Phe Leu Val Ala Ile Leu Lys Gly
1               5                   10                  15 gtc cag tgt gag gtt cag ctg gtg cag tct ggg gga ggc ttg gta cag    96
Val Gln Cys Glu Val Gln Leu Val Gln Ser Gly Gly Gly Leu Val Gln
            20                  25                  30 ccc ggg ggg tcc ctg aga ctc tcc tgt gca gcc tct gga ttc acc ttc   144
Pro Gly Gly Ser Leu Arg Leu Ser Cys Ala Ala Ser Gly Phe Thr Phe
        35                  40                  45 agt agc ttt gct atg cac tgg gtt cgc cag gct cca gga aaa ggt ctg   192
Ser Ser Phe Ala Met His Trp Val Arg Gln Ala Pro Gly Lys Gly Leu
    50                  55                  60 gag tgg ata tca gtt att gat act cgt ggt gcc aca tac tat gca gac   240
Glu Trp Ile Ser Val Ile Asp Thr Arg Gly Ala Thr Tyr Tyr Ala Asp
65                  70                  75                  80 tcc gtg aag ggc cga ttc acc atc tcc aga gac aat gcc aag aac tcc   288
Ser Val Lys Gly Arg Phe Thr Ile Ser Arg Asp Asn Ala Lys Asn Ser
                85                  90                  95 ttg tat ctt caa atg aac agc ctg aga gcc gag gac act gct gtg tat   336
Leu Tyr Leu Gln Met Asn Ser Leu Arg Ala Glu Asp Thr Ala Val Tyr
            100                 105                 110 tac tgt gca aga ctg ggg aac ttc tac tac ggt atg gac gtc tgg ggc   384
```

```
Tyr Cys Ala Arg Leu Gly Asn Phe Tyr Tyr Gly Met Asp Val Trp Gly
        115                 120                 125 caa ggg acc acg gtc acc gtc tcc tca                            411
Gln Gly Thr Thr Val Thr Val Ser Ser
        130                 135

<210> SEQ ID NO 12
<211> LENGTH: 137
<212> TYPE: PRT
<213> ORGANISM: Artificial Sequence
<220> FEATURE:
<223> OTHER INFORMATION: Synthetic Construct

<400> SEQUENCE: 12

Met Glu Phe Gly Leu Ser Trp Val Phe Leu Val Ala Ile Leu Lys Gly
1               5                   10                  15

Val Gln Cys Glu Val Gln Leu Val Gln Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Phe Ala Met His Trp Val Arg Gln Ala Pro Gly Lys Gly Leu
    50                  55                  60

Glu Trp Ile Ser Val Ile Asp Thr Arg Gly Ala Thr Tyr Tyr Ala Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Thr Ala Val Tyr
            100                 105                 110

Tyr Cys Ala Arg Leu Gly Asn Phe Tyr Tyr Gly Met Asp Val Trp Gly
        115                 120                 125

Gln Gly Thr Thr Val Thr Val Ser Ser
        130                 135

<210> SEQ ID NO 13
<211> LENGTH: 174
<212> TYPE: PRT
<213> ORGANISM: Artificial Sequence
<220> FEATURE:
<223> OTHER INFORMATION: immunoglobulin heavy chain variable region

<400> SEQUENCE: 13

Gly Arg Leu Gly Gln Ala Trp Arg Ser Leu Arg Leu Ser Cys Ala Ala
1               5                   10                  15

Ser Gly Phe Thr Phe Ser Asp Tyr Tyr Met Ser Trp Ile Arg Gln Ala
            20                  25                  30

Pro Gly Lys Gly Leu Glu Trp Val Ser Tyr Ile Ser Ser Ser Gly Ser
        35                  40                  45

Thr Arg Asp Tyr Ala Asp Ser Val Lys Gly Arg Phe Thr Ile Ser Arg
    50                  55                  60

Asp Asn Ala Lys Asn Ser Leu Tyr Leu Gln Met Asn Ser Leu Arg Ala
65                  70                  75                  80

Glu Asp Thr Ala Val Tyr Tyr Cys Val Arg Asp Gly Val Glu Thr Thr
                85                  90                  95

Phe Tyr Tyr Tyr Tyr Tyr Gly Met Asp Val Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140
```

```
Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ser Cys Ala
            165                 170

<210> SEQ ID NO 14
<211> LENGTH: 124
<212> TYPE: PRT
<213> ORGANISM: Artificial Sequence
<220> FEATURE:
<223> OTHER INFORMATION: immunoglobulin heavy chain variable region

<400> SEQUENCE: 14

Val Gln Leu Leu Glu Ser Gly Gly Gly Leu Val Gln Pro Gly Gly Ser
1               5                   10                  15

Leu Arg Leu Ser Cys Thr Ala Ser Gly Phe Thr Phe Ser Ser Tyr Ala
                20                  25                  30

Met Asn Trp Val Arg Gln Ala Pro Gly Lys Gly Leu Glu Trp Val Ser
            35                  40                  45

Ala Ile Ser Gly Ser Gly Gly Thr Thr Phe Tyr Ala Asp Ser Val Lys
        50                  55                  60

Gly Arg Phe Thr Ile Ser Arg Asp Asn Ser Arg Thr Thr Leu Tyr Leu
65                  70                  75                  80

Gln Met Asn Ser Leu Arg Ala Glu Asp Thr Ala Val Tyr Tyr Cys Ala
                85                  90                  95

Lys Asp Leu Gly Trp Ser Asp Ser Tyr Tyr Tyr Tyr Gly Met Asp
            100                 105                 110

Val Trp Gly Gln Gly Thr Thr Val Thr Val Ser Ser
        115                 120

<210> SEQ ID NO 15
<211> LENGTH: 112
<212> TYPE: PRT
<213> ORGANISM: Artificial Sequence
<220> FEATURE:
<223> OTHER INFORMATION: immunoglobulin heavy chain variable region

<400> SEQUENCE: 15

Gly Pro Gly Leu Val Lys Pro Ser Glu Thr Leu Ser Leu Thr Cys Thr
1               5                   10                  15

Val Ser Gly Gly Ser Ile Ser Asn Tyr Tyr Trp Ser Trp Ile Arg Gln
                20                  25                  30

Pro Ala Gly Lys Gly Leu Glu Trp Ile Gly Arg Ile Tyr Thr Ser Gly
            35                  40                  45

Ser Pro Asn Tyr Asn Pro Ser Leu Lys Ser Arg Val Thr Met Ser Val
        50                  55                  60

Asp Thr Ser Lys Asn Gln Phe Ser Leu Lys Leu Asn Ser Val Thr Ala
65                  70                  75                  80

Ala Asp Thr Ala Val Tyr Tyr Cys Ala Val Thr Ile Phe Gly Val Val
                85                  90                  95

Ile Ile Phe Asp Tyr Trp Gly Gln Gly Thr Leu Val Thr Val Ser Ser
            100                 105                 110

<210> SEQ ID NO 16
<211> LENGTH: 125
<212> TYPE: PRT
<213> ORGANISM: Artificial Sequence
<220> FEATURE:
<223> OTHER INFORMATION: immunoglobulin heavy chain variable region
```

```
<400> SEQUENCE: 16

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Gly Tyr Gly Asp Phe Tyr Tyr Tyr Tyr Gly Met
            100                 105                 110

Asp Val Trp Gly Gln Gly Thr Thr Val Thr Val Ser Ser
        115                 120                 125

<210> SEQ ID NO 17
<211> LENGTH: 113
<212> TYPE: PRT
<213> ORGANISM: Artificial Sequence
<220> FEATURE:
<223> OTHER INFORMATION: immunoglobulin heavy chain variable region

<400> SEQUENCE: 17

Pro Gly Leu Val Lys Pro Ser Glu Thr Leu Ser Leu Thr Cys Thr Val
1               5                   10                  15

Ser Gly Gly Ser Ile Ser Ser Tyr Tyr Trp Ser Trp Ile Arg Gln Pro
            20                  25                  30

Pro Gly Lys Gly Leu Glu Trp Ile Gly Tyr Ile Tyr Tyr Ser Gly Ser
        35                  40                  45

Thr Asn Tyr Asn Pro Ser Leu Lys Ser Arg Val Thr Ile Ser Val Asp
    50                  55                  60

Thr Ser Lys Asn Gln Phe Ser Leu Lys Leu Ser Ser Val Thr Ala Ala
65                  70                  75                  80

Asp Thr Ala Val Tyr Tyr Cys Ala Arg Thr Tyr Ser Ser Ser Phe Tyr
                85                  90                  95

Tyr Tyr Gly Met Asp Val Trp Gly Gln Gly Thr Thr Val Thr Val Ser
            100                 105                 110

Ser

<210> SEQ ID NO 18
<211> LENGTH: 122
<212> TYPE: PRT
<213> ORGANISM: Artificial Sequence
<220> FEATURE:
<223> OTHER INFORMATION: immunoglobulin heavy chain variable region

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Thr Gly Ser Gly Gly Ser Thr Tyr Tyr Ala Asp Ser Val
    50                  55                  60
```

-continued

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Pro Gly Thr Val Ile Met Ser Trp Phe Asp Pro Trp
            100                 105                 110

Gly Gln Gly Thr Leu Val Thr Val Ser Ser
        115                 120
```

<210> SEQ ID NO 19
<211> LENGTH: 136
<212> TYPE: PRT
<213> ORGANISM: Artificial Sequence
<220> FEATURE:
<223> OTHER INFORMATION: immunoglobulin light chain variable region

<400> SEQUENCE: 19

```
Ala Ser Val Gly Asp Arg Val Thr Phe Thr Cys Arg Ala Ser Gln Asp
 1               5                  10                  15

Ile Arg Arg Asp Leu Gly Trp Tyr Gln Gln Lys Pro Gly Lys Ala Pro
                20                  25                  30

Lys Arg Leu Ile Tyr Ala Ala Ser Arg Leu Gln Ser Gly Val Pro Ser
         35                  40                  45

Arg Phe Ser Gly Ser Gly Ser Gly Thr Glu Phe Thr Leu Thr Ile Ser
 50                  55                  60

Ser Leu Gln Pro Glu Asp Phe Ala Thr Tyr Tyr Cys Leu Gln His Asn
 65                  70                  75                  80

Asn Tyr Pro Arg Thr Phe Gly Gln Gly Thr Glu Val Glu Ile Ile Arg
                 85                  90                  95

Thr Val Ala Ala Pro Ser Val Phe Ile Phe Pro Pro Ser Asp Glu Gln
            100                 105                 110

Leu Lys Ser Gly Thr Ala Ser Val Val Cys Leu Leu Asn Asn Phe Tyr
        115                 120                 125

Pro Arg Glu Ala Lys Val Gln Trp
130                 135
```

<210> SEQ ID NO 20
<211> LENGTH: 107
<212> TYPE: PRT
<213> ORGANISM: Artificial Sequence
<220> FEATURE:
<223> OTHER INFORMATION: immunoglobulin light chain variable region

<400> SEQUENCE: 20

```
Asp Ile Gln Met Thr Gln Phe Pro Ser Ser Leu Ser Ala Ser Val Gly
 1               5                  10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
             35                  40                  45

Tyr Ala Ala Ser Arg Leu His Arg Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Cys
                 85                  90                  95

Ser Phe Gly Gln Gly Thr Lys Leu Glu Ile Lys
            100                 105
```

```
<210> SEQ ID NO 21
<211> LENGTH: 100
<212> TYPE: PRT
<213> ORGANISM: Artificial Sequence
<220> FEATURE:
<223> OTHER INFORMATION: immunoglobulin light chain variable region

<400> SEQUENCE: 21

Ser Ser Leu Ser Ala Ser Val Gly Asp Arg Val Thr Phe Thr Cys Arg
1               5                   10                  15

Ala Ser Gln Asp Ile Arg Arg Asp Leu Gly Trp Tyr Gln Gln Lys Pro
            20                  25                  30

Gly Lys Ala Pro Lys Arg Leu Ile Tyr Ala Ala Ser Arg Leu Gln Ser
        35                  40                  45

Gly Val Pro Ser Arg Phe Ser Gly Ser Gly Ser Gly Thr Glu Phe Thr
    50                  55                  60

Leu Thr Ile Ser Ser Leu Gln Pro Glu Asp Phe Ala Thr Tyr Tyr Cys
65                  70                  75                  80

Leu Gln His Asn Asn Tyr Pro Arg Thr Phe Gly Gln Gly Thr Glu Val
                85                  90                  95

Glu Ile Ile Arg
            100

<210> SEQ ID NO 22
<211> LENGTH: 107
<212> TYPE: PRT
<213> ORGANISM: Artificial Sequence
<220> FEATURE:
<223> OTHER INFORMATION: immunoglobulin light chain variable region

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Ser Asp
            20                  25                  30

Leu Gly Trp Phe Gln Gln Lys Pro Gly Lys Ala Pro Lys Arg Leu Ile
        35                  40                  45

Tyr Ala Ala Ser Lys Leu His Arg Gly Val Pro Ser Arg Phe Ser Gly
    50                  55                  60

Ser Gly Ser Gly Thr Glu Phe Thr Leu Thr Ile Ser Arg Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Glu Ile Lys
            100                 105

<210> SEQ ID NO 23
<211> LENGTH: 92
<212> TYPE: PRT
<213> ORGANISM: Artificial Sequence
<220> FEATURE:
<223> OTHER INFORMATION: immunoglobulin light chain variable region

<400> SEQUENCE: 23

Gly Asp Arg Val Thr Ile Thr Cys Arg Ala Ser Gln Ser Ile Ser Thr
1               5                   10                  15

Phe Leu Asn Trp Tyr Gln Gln Lys Pro Gly Lys Ala Pro Lys Leu Leu
            20                  25                  30

Ile His Val Ala Ser Ser Leu Gln Gly Gly Val Pro Ser Arg Phe Ser
```

```
                    35                  40                  45
Gly Ser Gly Ser Gly Thr Asp Phe Thr Leu Thr Ile Ser Ser Leu Gln
            50                  55                  60

Pro Glu Asp Phe Ala Thr Tyr Tyr Cys Gln Gln Ser Tyr Asn Ala Pro
65                  70                  75                  80

Leu Thr Phe Gly Gly Gly Thr Lys Val Glu Ile Lys
                85                  90

<210> SEQ ID NO 24
<211> LENGTH: 91
<212> TYPE: PRT
<213> ORGANISM: Artificial Sequence
<220> FEATURE:
<223> OTHER INFORMATION: immunoglobulin light chain variable region

<400> SEQUENCE: 24

Arg Ala Thr Leu Ser Cys Arg Ala Ser Gln Ser Val Arg Gly Arg Tyr
1               5                   10                  15

Leu Ala Trp Tyr Gln Gln Lys Pro Gly Gln Ala Pro Arg Leu Leu Ile
                20                  25                  30

Tyr Gly Ala Ser Ser Arg Ala Thr Gly Ile Pro Asp Arg Phe Ser Gly
            35                  40                  45

Ser Gly Ser Gly Thr Asp Phe Thr Leu Thr Ile Ser Arg Leu Glu Pro
        50                  55                  60

Glu Asp Phe Ala Val Phe Tyr Cys Gln Gln Tyr Gly Ser Ser Pro Arg
65                  70                  75                  80

Thr Phe Gly Gln Gly Thr Lys Val Glu Ile Lys
                85                  90

<210> SEQ ID NO 25
<211> LENGTH: 236
<212> TYPE: PRT
<213> ORGANISM: Artificial Sequence
<220> FEATURE:
<223> OTHER INFORMATION: light chain immunoglobulin

<400> SEQUENCE: 25

Met Asp Met Arg Val Pro Ala Gln Leu Leu Gly Leu Leu Leu Leu Trp
1               5                   10                  15

Phe Pro Gly Ala Arg Cys Asp Ile Gln Met Thr Gln Ser Pro Ser Ser
                20                  25                  30

Leu Ser Ala Ser Val Gly Asp Arg Val Thr Ile Thr Cys Arg Ala Ser
            35                  40                  45

Gln Gly Ile Arg Asn Asp Leu Gly Trp Tyr Gln Gln Lys Pro Gly Lys
        50                  55                  60

Ala Pro Lys Arg Leu Ile Tyr Ala Ala Ser Ser Leu Gln Ser Gly Val
65                  70                  75                  80

Pro Ser Arg Phe Ser Gly Ser Gly Ser Gly Thr Glu Phe Thr Leu Thr
                85                  90                  95

Ile Ser Ser Leu Gln Pro Glu Asp Phe Ala Thr Tyr Tyr Cys Leu Gln
                100                 105                 110

His Asn Ser Tyr Pro Trp Thr Phe Gly Gln Gly Thr Lys Val Glu Ile
            115                 120                 125

Lys Arg Thr Val Ala Ala Pro Ser Val Phe Ile Phe Pro Pro Ser Asp
        130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
```

```
                   165                 170                 175
Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
            210                 215                 220

Ser Pro Val Thr Lys Ser Phe Asn Arg Gly Glu Cys
225                 230                 235

<210> SEQ ID NO 26
<211> LENGTH: 236
<212> TYPE: PRT
<213> ORGANISM: Artificial Sequence
<220> FEATURE:
<223> OTHER INFORMATION: light chain immunoglobulin

<400> SEQUENCE: 26

Met Asp Met Arg Val Pro Ala Gln Leu Leu Gly Leu Leu Leu Leu Trp
1               5                   10                  15

Phe Pro Gly Ala Arg Cys Asp Ile Gln Met Thr Gln Ser Pro Ser Ser
            20                  25                  30

Leu Ser Ala Ser Val Gly Asp Arg Val Thr Phe Thr Cys Arg Ala Ser
            35                  40                  45

Gln Asp Ile Arg Arg Asp Leu Gly Trp Tyr Gln Gln Lys Pro Gly Lys
        50                  55                  60

Ala Pro Lys Arg Leu Ile Tyr Ala Ala Ser Arg Leu Gln Ser Gly Val
65                  70                  75                  80

Pro Ser Arg Phe Ser Gly Ser Gly Ser Gly Thr Glu Phe Thr Leu Thr
            85                  90                  95

Ile Ser Ser Leu Gln Pro Glu Asp Phe Ala Thr Tyr Tyr Cys Leu Gln
            100                 105                 110

His Asn Asn Tyr Pro Arg Thr Phe Gly Gln Gly Thr Glu Val Glu Ile
            115                 120                 125

Ile Arg Thr Val Ala Ala Pro Ser Val Phe Ile Phe Pro Pro Ser Asp
        130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
            165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
            210                 215                 220

Ser Pro Val Thr Lys Ser Phe Asn Arg Gly Glu Cys
225                 230                 235

<210> SEQ ID NO 27
<211> LENGTH: 236
<212> TYPE: PRT
<213> ORGANISM: Artificial Sequence
<220> FEATURE:
<223> OTHER INFORMATION: light chain immunoglobulin

<400> SEQUENCE: 27

Met Asp Met Arg Val Pro Ala Gln Leu Leu Gly Leu Leu Leu Leu Trp
```

```
                1               5                  10                 15
Phe Pro Gly Ala Arg Cys Asp Ile Gln Met Thr Gln Ser Pro Ser Ser
                20                 25                 30

Leu Ser Ala Ser Val Gly Asp Arg Val Thr Ile Thr Cys Arg Ala Ser
            35                 40                 45

Gln Gly Ile Arg Asn Asp Leu Gly Trp Tyr Gln Gln Lys Pro Gly Lys
        50                 55                 60

Ala Pro Lys Arg Leu Ile Tyr Ala Ala Ser Ser Leu Gln Ser Gly Val
65                  70                 75                 80

Pro Ser Arg Phe Ser Gly Ser Gly Ser Gly Thr Glu Phe Thr Leu Thr
                85                 90                 95

Ile Ser Ser Leu Gln Pro Glu Asp Phe Ala Thr Tyr Tyr Cys Leu Gln
                100                105                110

His Asn Ser Tyr Pro Tyr Thr Phe Gly Gln Gly Thr Lys Leu Glu Ile
            115                120                125

Lys Arg Thr Val Ala Ala Pro Ser Val Phe Ile Phe Pro Pro Ser Asp
        130                135                140

Glu Gln Leu Lys Ser Gly Thr Ala Ser Val Val Cys Leu Leu Asn Asn
145                 150                155                160

Phe Tyr Pro Arg Glu Ala Lys Val Gln Trp Lys Val Asp Asn Ala Leu
                165                170                175

Gln Ser Gly Asn Ser Gln Glu Ser Val Thr Glu Gln Asp Ser Lys Asp
            180                185                190

Ser Thr Tyr Ser Leu Ser Ser Thr Leu Thr Leu Ser Lys Ala Asp Tyr
        195                200                205

Glu Lys His Lys Val Tyr Ala Cys Glu Val Thr His Gln Gly Leu Ser
    210                215                220

Ser Pro Val Thr Lys Ser Phe Asn Arg Gly Glu Cys
225                 230                235

<210> SEQ ID NO 28
<211> LENGTH: 236
<212> TYPE: PRT
<213> ORGANISM: Artificial Sequence
<220> FEATURE:
<223> OTHER INFORMATION: light chain immunoglobulin

<400> SEQUENCE: 28

Met Asp Met Arg Val Pro Ala Gln Leu Leu Gly Leu Leu Leu Leu Trp
1               5                  10                 15

Phe Pro Gly Ala Arg Cys Asp Ile Gln Met Thr Gln Phe Pro Ser Ser
                20                 25                 30

Leu Ser Ala Ser Val Gly Asp Arg Val Thr Ile Thr Cys Arg Ala Ser
            35                 40                 45

Gln Gly Ile Arg Asn Asp Leu Gly Trp Tyr Gln Gln Lys Pro Gly Lys
        50                 55                 60

Ala Pro Lys Arg Leu Ile Tyr Ala Ala Ser Arg Leu His Arg Gly Val
65                  70                 75                 80

Pro Ser Arg Phe Ser Gly Ser Gly Ser Gly Thr Glu Phe Thr Leu Thr
                85                 90                 95

Ile Ser Ser Leu Gln Pro Glu Asp Phe Ala Thr Tyr Tyr Cys Leu Gln
                100                105                110

His Asn Ser Tyr Pro Cys Ser Phe Gly Gln Gly Thr Lys Leu Glu Ile
            115                120                125

Lys Arg Thr Val Ala Ala Pro Ser Val Phe Ile Phe Pro Pro Ser Asp
        130                135                140
```

```
Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 29
<211> LENGTH: 473
<212> TYPE: PRT
<213> ORGANISM: Artificial Sequence
<220> FEATURE:
<223> OTHER INFORMATION: heavy chain immunoglobulin

<400> SEQUENCE: 29

Met Glu Phe Gly Leu Ser Trp Val Phe Leu Val Ala Ile Ile Lys Gly
1               5                   10                  15

Val Gln Cys Gln Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Asp Tyr Tyr Met Ser Trp Ile Arg Gln Ala Pro Gly Lys Gly Leu
    50                  55                  60

Glu Trp Val Ser Tyr Ile Ser Ser Ser Gly Ser Thr Ile Tyr Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Val Leu Arg Phe Leu Glu Trp Leu Leu Tyr Tyr
        115                 120                 125

Tyr Tyr Tyr Gly Met Asp Val Trp Gly Gln Gly Thr Thr Val Thr
    130                 135                 140

Val Ser Ser Ala Ser Thr Lys Gly Pro Ser Val Phe Pro Leu Ala Pro
145                 150                 155                 160

Cys Ser Arg Ser Thr Ser Glu Ser Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Asn Phe Gly
    210                 215                 220

Thr Gln Thr Tyr Thr Cys Asn Val Asp His Lys Pro Ser Asn Thr Lys
225                 230                 235                 240

Val Asp Lys Thr Val Glu Arg Lys Cys Cys Val Glu Cys Pro Pro Cys
                245                 250                 255

Pro Ala Pro Pro Val Ala Gly Pro Ser Val Phe Leu Phe Pro Pro Lys
            260                 265                 270
```

-continued

Pro Lys Asp Thr Leu Met Ile Ser Arg Thr Pro Glu Val Thr Cys Val
        275                 280                 285

Val Val Asp Val Ser His Glu Asp Pro Glu Val Gln Phe Asn Trp Tyr
    290                 295                 300

Val Asp Gly Val Glu Val His Asn Ala Lys Thr Lys Pro Arg Glu Glu
305                 310                 315                 320

Gln Phe Asn Ser Thr Phe Arg Val Val Ser Val Leu Thr Val His
                325                 330                 335

Gln Asp Trp Leu Asn Gly Lys Glu Tyr Lys Cys Lys Val Ser Asn Lys
                340                 345                 350

Gly Leu Pro Ala Pro Ile Glu Lys Thr Ile Ser Lys Thr Lys Gly Gln
            355                 360                 365

Pro Arg Glu Pro Gln Val Tyr Thr Leu Pro Pro Ser Arg Glu Glu Met
        370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Met Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470

<210> SEQ ID NO 30
<211> LENGTH: 470
<212> TYPE: PRT
<213> ORGANISM: Artificial Sequence
<220> FEATURE:
<223> OTHER INFORMATION: heavy chain immunoglobulin

<400> SEQUENCE: 30

Met Glu Phe Gly Leu Ser Trp Val Phe Leu Val Ala Ile Ile Lys Gly
1               5                   10                  15

Val Gln Cys Gln Ala Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Asp Tyr Tyr Met Ser Trp Ile Arg Gln Ala Pro Gly Lys Gly Leu
    50                  55                  60

Glu Trp Val Ser Tyr Ile Ser Ser Gly Ser Thr Arg Asp Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Val Arg Asp Gly Val Glu Thr Thr Phe Tyr Tyr Tyr
        115                 120                 125

Tyr Gly Met Asp Val Trp Gly Gln Gly Thr Thr Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr

```
                  165                 170                 175
Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
            195                 200                 205

Leu Ser Ser Val Val Thr Val Pro Ser Ser Asn Phe Gly Thr Gln Thr
        210                 215                 220

Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
                245                 250                 255

Pro Val Ala Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Gln Phe Asn Trp Tyr Val Asp Gly
    290                 295                 300

Val Glu Val His Asn Ala Lys Thr Lys Pro Arg Glu Glu Gln Phe Asn
305                 310                 315                 320

Ser Thr Phe Arg Val Val Ser Val Leu Thr Val Val His Gln Asp Trp
                325                 330                 335

Leu Asn Gly Lys Glu Tyr Lys Cys Lys Val Ser Asn Lys Gly Leu Pro
            340                 345                 350

Ala Pro Ile Glu Lys Thr Ile Ser Lys Thr Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Met Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 31
<211> LENGTH: 470
<212> TYPE: PRT
<213> ORGANISM: Artificial Sequence
<220> FEATURE:
<223> OTHER INFORMATION: heavy chain immunoglobulin

<400> SEQUENCE: 31

Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met Ser Trp Val Arg Gln Ala Pro Gly Lys Gly Leu
    50                  55                  60
```

```
Glu Trp Val Ser Ala Ile Ser Gly Ser Gly Gly Ser Thr Tyr Tyr Ala
 65                  70                  75                  80

Asp Ser Val Lys Gly Arg Phe Thr Ile Ser Arg Asp Asn Ser Lys Asn
             85                   90                  95

Thr Leu Tyr Leu Gln Met Asn Ser Leu Arg Ala Glu Asp Thr Ala Val
            100                 105                 110

Tyr Tyr Cys Ala Lys Gly Tyr Ser Ser Gly Trp Tyr Tyr Tyr Tyr Tyr
        115                 120                 125

Tyr Gly Met Asp Val Trp Gly Gln Gly Thr Thr Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Asn Phe Gly Thr Gln Thr
    210                 215                 220

Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
                245                 250                 255

Pro Val Ala Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Gln Phe Asn Trp Tyr Val Asp Gly
    290                 295                 300

Val Glu Val His Asn Ala Lys Thr Lys Pro Arg Glu Glu Gln Phe Asn
305                 310                 315                 320

Ser Thr Phe Arg Val Val Ser Val Leu Thr Val Val His Gln Asp Trp
                325                 330                 335

Leu Asn Gly Lys Glu Tyr Lys Cys Lys Val Ser Asn Lys Gly Leu Pro
            340                 345                 350

Ala Pro Ile Glu Lys Thr Ile Ser Lys Thr Lys Gly Gln Pro Arg Glu
        355                 360                 365

Pro Gln Val Tyr Thr Leu Pro Pro Ser Arg Glu Glu Met Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Met Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470
```

```
<210> SEQ ID NO 32
<211> LENGTH: 470
<212> TYPE: PRT
<213> ORGANISM: Artificial Sequence
<220> FEATURE:
<223> OTHER INFORMATION: heavy chain immunoglobulin

<400> SEQUENCE: 32

Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Thr Ala Ser Gly Phe Thr Phe
        35                  40                  45

Ser Ser Tyr Ala Met Asn Trp Val Arg Gln Ala Pro Gly Lys Gly Leu
    50                  55                  60

Glu Trp Val Ser Ala Ile Ser Gly Ser Gly Gly Thr Thr Phe Tyr Ala
65                  70                  75                  80

Asp Ser Val Lys Gly Arg Phe Thr Ile Ser Arg Asp Asn Ser Arg Thr
                85                  90                  95

Thr Leu Tyr Leu Gln Met Asn Ser Leu Arg Ala Glu Asp Thr Ala Val
            100                 105                 110

Tyr Tyr Cys Ala Lys Asp Leu Gly Trp Ser Asp Ser Tyr Tyr Tyr Tyr
        115                 120                 125

Tyr Gly Met Asp Val Trp Gly Gln Gly Thr Thr Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Asn Phe Gly Thr Gln Thr
    210                 215                 220

Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
                245                 250                 255

Pro Val Ala Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Gln Phe Asn Trp Tyr Val Asp Gly
    290                 295                 300

Val Glu Val His Asn Ala Lys Thr Lys Pro Arg Glu Glu Gln Phe Asn
305                 310                 315                 320

Ser Thr Phe Arg Val Val Ser Val Leu Thr Val His Gln Asp Trp
                325                 330                 335

Leu Asn Gly Lys Glu Tyr Lys Cys Lys Val Ser Asn Lys Gly Leu Pro
            340                 345                 350

Ala Pro Ile Glu Lys Thr Ile Ser Lys Thr Lys Gly Gln Pro Arg Glu
        355                 360                 365

Pro Gln Val Tyr Thr Leu Pro Pro Ser Arg Glu Glu Met Thr Lys Asn
    370                 375                 380
```

```
Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415

Thr Pro Pro Met Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
        450                 455                 460

Ser Leu Ser Pro Gly Lys
465             470

<210> SEQ ID NO 33
<211> LENGTH: 470
<212> TYPE: PRT
<213> ORGANISM: Artificial Sequence
<220> FEATURE:
<223> OTHER INFORMATION: immunoglobulin heavy chain of 2.12.1 fx

<400> SEQUENCE: 33

Met Glu Phe Gly Leu Ser Trp Val Phe Leu Val Ala Ile Ile Lys Gly
1               5                   10                  15

Val Gln Cys Gln Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Asp Tyr Tyr Met Ser Trp Ile Arg Gln Ala Pro Gly Lys Gly Leu
    50                  55                  60

Glu Trp Val Ser Tyr Ile Ser Ser Ser Gly Ser Thr Arg Asp Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Asp Gly Val Glu Thr Thr Phe Tyr Tyr Tyr Tyr
        115                 120                 125

Tyr Gly Met Asp Val Trp Gly Gln Gly Thr Thr Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Asn Phe Gly Thr Gln Thr
    210                 215                 220

Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
                245                 250                 255

Pro Val Ala Gly Pro Ser Val Phe Leu Phe Pro Pro Lys Pro Lys Asp
            260                 265                 270
```

-continued

```
Thr Leu Met Ile Ser Arg Thr Pro Glu Val Thr Cys Val Val Asp
        275                 280                 285

Val Ser His Glu Asp Pro Glu Val Gln Phe Asn Trp Tyr Val Asp Gly
290                 295                 300

Val Glu Val His Asn Ala Lys Thr Lys Pro Arg Glu Glu Gln Phe Asn
305                 310                 315                 320

Ser Thr Phe Arg Val Val Ser Val Leu Thr Val Val His Gln Asp Trp
                325                 330                 335

Leu Asn Gly Lys Glu Tyr Lys Cys Lys Val Ser Asn Lys Gly Leu Pro
            340                 345                 350

Ala Pro Ile Glu Lys Thr Ile Ser Lys Thr Lys Gly Gln Pro Arg Glu
        355                 360                 365

Pro Gln Val Tyr Thr Leu Pro Pro Ser Arg Glu Glu Met Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Met Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
450                 455                 460

Ser Leu Ser Pro Gly Lys
465                 470

<210> SEQ ID NO 34
<211> LENGTH: 125
<212> TYPE: PRT
<213> ORGANISM: Artificial Sequence
<220> FEATURE:
<223> OTHER INFORMATION: mature immunoglobulin heavy chain variable
      region of 2.12.1 fx

<400> SEQUENCE: 34

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Arg Asp Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Val Glu Thr Thr Phe Tyr Tyr Tyr Tyr Gly Met
            100                 105                 110

Asp Val Trp Gly Gln Gly Thr Thr Val Thr Val Ser Ser
        115                 120                 125

<210> SEQ ID NO 35
<211> LENGTH: 236
<212> TYPE: PRT
<213> ORGANISM: Artificial Sequence
<220> FEATURE:
```

<223> OTHER INFORMATION: immunoglobulin light chain of 2.12.1 fx

<400> SEQUENCE: 35

```
Met Asp Met Arg Val Pro Ala Gln Leu Leu Gly Leu Leu Leu Leu Trp
1               5                   10                  15

Phe Pro Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Asp Ile Arg Arg Asp Leu Gly Trp Tyr Gln Gln Lys Pro Gly Lys
    50                  55                  60

Ala Pro Lys Arg Leu Ile Tyr Ala Ala Ser Arg Leu Gln Ser Gly Val
65                  70                  75                  80

Pro Ser Arg Phe Ser Gly Ser Gly Ser Gly Thr Glu Phe Thr Leu Thr
                85                  90                  95

Ile Ser Ser Leu Gln Pro Glu Asp Phe Ala Thr Tyr Tyr Cys Leu Gln
            100                 105                 110

His Asn Asn Tyr Pro Arg Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 36
<211> LENGTH: 108
<212> TYPE: PRT
<213> ORGANISM: Artificial Sequence
<220> FEATURE:
<223> OTHER INFORMATION: mature immunoglobulin light chain variable region of 2.12.1 fx

<400> SEQUENCE: 36

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Arg Asp
            20                  25                  30

Leu Gly Trp Tyr Gln Gln Lys Pro Gly Lys Ala Pro Lys Arg Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Asn Tyr Pro Arg
                85                  90                  95

Thr Phe Gly Gln Gly Thr Lys Val Glu Ile Lys Arg
            100                 105
```

```
<210> SEQ ID NO 37
<211> LENGTH: 112
<212> TYPE: PRT
<213> ORGANISM: Artificial Sequence
<220> FEATURE:
<223> OTHER INFORMATION: humanized 7C10 immunoglobulin light chain
      variable region; version 1

<400> SEQUENCE: 37

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Gln Trp Tyr Leu Gln Lys Pro Gly Gln Ser
        35                  40                  45

Pro Gln Leu Leu Ile Tyr Lys Val Ser Asn Arg Leu Tyr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gln Gly Thr Lys Val Glu Ile Lys
            100                 105                 110

<210> SEQ ID NO 38
<211> LENGTH: 112
<212> TYPE: PRT
<213> ORGANISM: Artificial Sequence
<220> FEATURE:
<223> OTHER INFORMATION: humanized 7C10 immunoglobulin light chain
      variable region; version 2

<400> SEQUENCE: 38

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Gln Trp Tyr Leu Gln Lys Pro Gly Gln Ser
        35                  40                  45

Pro Gln Leu Leu Ile Tyr Lys Val Ser Asn Arg Leu Tyr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gln Gly Thr Lys Val Glu Ile Lys
            100                 105                 110

<210> SEQ ID NO 39
<211> LENGTH: 117
<212> TYPE: PRT
<213> ORGANISM: Artificial Sequence
<220> FEATURE:
<223> OTHER INFORMATION: humanized 7C10 immunoglobulin heavy chain
      variable region; version 1

<400> SEQUENCE: 39

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Gly Gly
```

```
                    20                  25                  30
Tyr Leu Trp Asn Trp Ile Arg Gln Pro Pro Gly Lys Gly Leu Glu Trp
            35                  40                  45
Met Gly Tyr Ile Ser Tyr Asp Gly Thr Asn Asn Tyr Lys Pro Ser Leu
    50                  55                  60
Lys Asp Arg Ile Thr Ile Ser Arg Asp Thr Ser Lys Asn Gln Phe Ser
65                  70                  75                  80
Leu Lys Leu Ser Ser Val Thr Ala Ala Asp Thr Ala Val Tyr Tyr Cys
                85                  90                  95
Ala Arg Tyr Gly Arg Val Phe Phe Asp Tyr Trp Gly Gln Gly Thr Leu
            100                 105                 110
Val Thr Val Ser Ser
        115

<210> SEQ ID NO 40
<211> LENGTH: 117
<212> TYPE: PRT
<213> ORGANISM: Artificial Sequence
<220> FEATURE:
<223> OTHER INFORMATION: humanized 7C10 immunoglobulin heavy chain
      variable region; version 2

<400> SEQUENCE: 40

Gln Val Gln Leu Gln Glu Ser Gly Pro Gly Leu Val Lys Pro Ser Glu
1               5                   10                  15
Thr Leu Ser Leu Thr Cys Thr Val Ser Gly Tyr Ser Ile Thr Gly Gly
            20                  25                  30
Tyr Leu Trp Asn Trp Ile Arg Gln Pro Pro Gly Lys Gly Leu Glu Trp
            35                  40                  45
Ile Gly Tyr Ile Ser Tyr Asp Gly Thr Asn Asn Tyr Lys Pro Ser Leu
    50                  55                  60
Lys Asp Arg Val Thr Ile Ser Arg Asp Thr Ser Lys Asn Gln Phe Ser
65                  70                  75                  80
Leu Lys Leu Ser Ser Val Thr Ala Ala Asp Thr Ala Val Tyr Tyr Cys
                85                  90                  95
Ala Arg Tyr Gly Arg Val Phe Phe Asp Tyr Trp Gly Gln Gly Thr Leu
            100                 105                 110
Val Thr Val Ser Ser
        115

<210> SEQ ID NO 41
<211> LENGTH: 117
<212> TYPE: PRT
<213> ORGANISM: Artificial Sequence
<220> FEATURE:
<223> OTHER INFORMATION: humanized 7C10 immunoglobulin heavy chain
      variable region; version 3

<400> SEQUENCE: 41

Gln Val Gln Leu Gln Glu Ser Gly Pro Gly Leu Val Lys Pro Ser Glu
1               5                   10                  15
Thr Leu Ser Leu Thr Cys Thr Val Ser Gly Tyr Ser Ile Ser Gly Gly
            20                  25                  30
Tyr Leu Trp Asn Trp Ile Arg Gln Pro Pro Gly Lys Gly Leu Glu Trp
            35                  40                  45
Ile Gly Tyr Ile Ser Tyr Asp Gly Thr Asn Asn Tyr Lys Pro Ser Leu
    50                  55                  60
Lys Asp Arg Val Thr Ile Ser Val Asp Thr Ser Lys Asn Gln Phe Ser
65                  70                  75                  80
```

```
Leu Lys Leu Ser Ser Val Thr Ala Ala Asp Thr Ala Val Tyr Tyr Cys
                85                  90                  95

Ala Arg Tyr Gly Arg Val Phe Phe Asp Tyr Trp Gly Gln Gly Thr Leu
            100                 105                 110

Val Thr Val Ser Ser
        115

<210> SEQ ID NO 42
<211> LENGTH: 130
<212> TYPE: PRT
<213> ORGANISM: Artificial Sequence
<220> FEATURE:
<223> OTHER INFORMATION: A12 immunoglobulin heavy chain variable region

<400> SEQUENCE: 42

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Pro Leu Arg Phe Leu Glu Trp Ser Thr Gln Asp His Tyr
            100                 105                 110

Tyr Tyr Tyr Tyr Met Asp Val Trp Gly Lys Gly Thr Thr Val Thr Val
        115                 120                 125

Ser Ser
    130

<210> SEQ ID NO 43
<211> LENGTH: 109
<212> TYPE: PRT
<213> ORGANISM: Artificial Sequence
<220> FEATURE:
<223> OTHER INFORMATION: A12 immunoglobulin light chain variable region

<400> SEQUENCE: 43

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Asn Ser Asp Asn Arg
                85                  90                  95

Leu Ile Phe Gly Gly Gly Thr Lys Leu Thr Val Leu Ser
            100                 105

<210> SEQ ID NO 44
```

```
<211> LENGTH: 119
<212> TYPE: PRT
<213> ORGANISM: Artificial Sequence
<220> FEATURE:
<223> OTHER INFORMATION: 1A immunoglobulin heavy chain variable region
<220> FEATURE:
<221> NAME/KEY: MISC_FEATURE
<222> LOCATION: (1)..(119)
<223> OTHER INFORMATION: Possible mutations: R30, S30, N31, S31, Y94,
      H94, D104, E104.

<400> SEQUENCE: 44

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Arg Asn Tyr
            20                  25                  30

Ala Met Tyr Trp Val Arg Gln Ala Pro Gly Lys Gly Leu Glu Trp Val
        35                  40                  45

Ser Ala Ile Gly Ser Gly Gly Gly Thr Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Ala Pro Asn Trp Gly Ser Asp Ala Phe Asp Ile Trp Gly Gln Gly
            100                 105                 110

Thr Met Val Thr Val Ser Ser
        115

<210> SEQ ID NO 45
<211> LENGTH: 107
<212> TYPE: PRT
<213> ORGANISM: Artificial Sequence
<220> FEATURE:
<223> OTHER INFORMATION: 1A immunoglobulin light chain variable region
<220> FEATURE:
<221> NAME/KEY: MISC_FEATURE
<222> LOCATION: (1)..(107)
<223> OTHER INFORMATION: possible mutations: P96, I96, P100, Q100, R103,
      K103, V104, L104, D105, E105

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Pro Gly Thr Lys Val Asp Ile Lys
            100                 105

<210> SEQ ID NO 46
<211> LENGTH: 251
<212> TYPE: PRT
<213> ORGANISM: Artificial Sequence
<220> FEATURE:
<223> OTHER INFORMATION: single chain fv 8A1
```

<400> SEQUENCE: 46

```
Glu Val Gln Leu Val Gln Ser Gly Ala Glu Val Lys Lys Pro Gly Glu
1               5                   10                  15
Ser Leu Thr Ile Ser Cys Lys Gly Pro Gly Tyr Asn Phe Phe Asn Tyr
            20                  25                  30
Trp Ile Gly Trp Val Arg Gln Met Pro Gly Lys Gly Leu Glu Trp Met
        35                  40                  45
Gly Ile Ile Tyr Pro Thr Asp Ser Asp Thr Arg Tyr Ser Pro Ser Phe
    50                  55                  60
Gln Gly Gln Val Thr Ile Ser Val Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Ala Arg Ser Ile Arg Tyr Cys Pro Gly Gly Arg Cys Tyr Ser Gly Tyr
            100                 105                 110
Tyr Gly Met Asp Val Trp Gly Gln Gly Thr Met Val Thr Val Ser Ser
        115                 120                 125
Gly Gly Gly Gly Ser Gly Gly Gly Ser Gly Gly Gly Gly Ser Ser
    130                 135                 140
Glu Leu Thr Gln Asp Pro Ala Val Ser Val Ala Leu Gly Gln Thr Val
145                 150                 155                 160
Arg Ile Thr Cys Gln Gly Asp Ser Leu Arg Ser Tyr Tyr Ala Ser Trp
                165                 170                 175
Tyr Gln Gln Lys Pro Gly Gln Ala Pro Val Leu Val Ile Tyr Gly Lys
            180                 185                 190
Asn Asn Arg Pro Ser Gly Ile Pro Asp Arg Phe Ser Gly Ser Ser Ser
        195                 200                 205
Gly Asn Thr Ala Ser Leu Thr Ile Thr Gly Ala Gln Ala Glu Asp Glu
    210                 215                 220
Ala Asp Tyr Tyr Cys Asn Ser Arg Asp Ser Ser Gly Asn His Val Val
225                 230                 235                 240
Phe Gly Gly Gly Thr Lys Leu Thr Val Leu Gly
                245                 250
```

<210> SEQ ID NO 47
<211> LENGTH: 245
<212> TYPE: PRT
<213> ORGANISM: Artificial Sequence
<220> FEATURE:
<223> OTHER INFORMATION: single chain fv 9A2

<400> SEQUENCE: 47

```
Gln Val Gln Leu Val Gln Ser Gly Ala Glu Val Arg Lys Pro Gly Ala
1               5                   10                  15
Ser Val Lys Val Ser Cys Lys Thr Ser Gly Tyr Thr Phe Arg Asn Tyr
            20                  25                  30
Asp Ile Asn Trp Val Arg Gln Ala Pro Gly Gln Gly Leu Glu Trp Met
        35                  40                  45
Gly Arg Ile Ser Gly His Tyr Gly Asn Thr Asp His Ala Gln Lys Phe
    50                  55                  60
Gln Gly Arg Phe Thr Met Thr Lys Asp Thr Ser Thr Ser Thr Ala Tyr
65                  70                  75                  80
Met Glu Leu Arg Ser Leu Thr Phe Asp Asp Thr Ala Val Tyr Tyr Cys
                85                  90                  95
Ala Arg Ser Gln Trp Asn Val Asp Tyr Trp Gly Arg Gly Thr Leu Val
```

```
Thr Val Ser Ser Gly Gly Gly Ser Gly Gly Gly Ser Gly Gly
        115                 120                 125
Gly Gly Ser Ala Leu Asn Phe Met Leu Thr Gln Pro His Ser Val Ser
130                 135                 140
Glu Ser Pro Gly Lys Thr Val Thr Ile Ser Cys Thr Arg Ser Ser Gly
145                 150                 155                 160
Ser Ile Ala Ser Asn Tyr Val Gln Trp Tyr Gln Gln Arg Pro Gly Ser
                165                 170                 175
Ser Pro Thr Thr Val Ile Phe Glu Asp Asn Arg Arg Pro Ser Gly Val
                180                 185                 190
Pro Asp Arg Phe Ser Gly Ser Ile Asp Thr Ser Ser Asn Ser Ala Ser
                195                 200                 205
Leu Thr Ile Ser Gly Leu Lys Thr Glu Asp Glu Ala Asp Tyr Tyr Cys
                210                 215                 220
Gln Ser Phe Asp Ser Thr Asn Leu Val Val Phe Gly Gly Gly Thr Lys
225                 230                 235                 240
Val Thr Val Leu Gly
                245

<210> SEQ ID NO 48
<211> LENGTH: 245
<212> TYPE: PRT
<213> ORGANISM: Artificial Sequence
<220> FEATURE:
<223> OTHER INFORMATION: single chain fv 11A4

<400> SEQUENCE: 48

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
                20                  25                  30
Ala Met Ser Trp Val Arg Gln Ala Pro Gly Lys Gly Leu Glu Trp Val
            35                  40                  45
Ser Ala Ile Ser Gly Ser Gly Gly Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Ser Ser Pro Tyr Ser Ser Arg Trp Tyr Ser Phe Asp Pro Trp Gly
                100                 105                 110
Gln Gly Thr Met Val Thr Val Ser Ser Gly Gly Gly Ser Gly Gly
            115                 120                 125
Gly Gly Ser Gly Gly Gly Gly Ser Ala Leu Ser Tyr Glu Leu Thr Gln
130                 135                 140
Pro Pro Ser Val Ser Val Ser Pro Gly Gln Thr Ala Thr Ile Thr Cys
145                 150                 155                 160
Ser Gly Asp Asp Leu Gly Asn Lys Tyr Val Ser Trp Tyr Gln Gln Lys
                165                 170                 175
Pro Gly Gln Ser Pro Val Leu Val Ile Tyr Gln Asp Thr Lys Arg Pro
                180                 185                 190
Ser Gly Ile Pro Glu Arg Phe Ser Gly Ser Asn Ser Gly Asn Ile Ala
                195                 200                 205
Thr Leu Thr Ile Ser Gly Thr Gln Ala Val Asp Glu Ala Asp Tyr Tyr
                210                 215                 220
```

```
Cys Gln Val Trp Asp Thr Gly Thr Val Val Phe Gly Gly Thr Lys
225                 230                 235                 240

Leu Thr Val Leu Gly
                245

<210> SEQ ID NO 49
<211> LENGTH: 251
<212> TYPE: PRT
<213> ORGANISM: Artificial Sequence
<220> FEATURE:
<223> OTHER INFORMATION: single chain fv 7A4

<400> SEQUENCE: 49

Glu Val Gln Leu Val Gln Ser Gly Ala Glu Val Lys Lys Pro Gly Glu
1               5                   10                  15

Ser Leu Thr Ile Ser Cys Lys Gly Ser Gly Tyr Asn Phe Phe Asn Tyr
            20                  25                  30

Trp Ile Gly Trp Val Arg Gln Met Pro Gly Lys Asp Leu Glu Trp Met
        35                  40                  45

Gly Ile Ile Tyr Pro Thr Asp Ser Asp Thr Arg Tyr Ser Pro Ser Phe
    50                  55                  60

Gln Gly Gln Val Thr Ile Ser Val Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Ile Arg Tyr Cys Pro Gly Gly Arg Cys Tyr Ser Gly Tyr
            100                 105                 110

Tyr Gly Met Asp Val Trp Gly Gln Gly Thr Met Val Thr Val Ser Ser
        115                 120                 125

Gly Gly Gly Ser Ser Gly Gly Gly Ser Gly Gly Gly Ser Ser
    130                 135                 140

Glu Leu Thr Gln Asp Pro Ala Val Ser Val Ala Leu Gly Gln Thr Val
145                 150                 155                 160

Arg Ile Thr Cys Arg Gly Asp Ser Leu Arg Asn Tyr Tyr Ala Ser Trp
                165                 170                 175

Tyr Gln Gln Lys Pro Gly Gln Ala Pro Val Leu Val Ile Tyr Gly Lys
            180                 185                 190

Asn Asn Arg Pro Ser Gly Ile Pro Asp Arg Phe Ser Gly Ser Ser Ser
        195                 200                 205

Gly Asn Thr Ala Ser Leu Thr Ile Thr Gly Ala Gln Ala Glu Asp Glu
    210                 215                 220

Ala Asp Tyr Tyr Cys Asn Ser Arg Asp Ser Ser Gly Asn His Met Val
225                 230                 235                 240

Phe Gly Gly Gly Thr Lys Leu Thr Val Leu Gly
                245                 250

<210> SEQ ID NO 50
<211> LENGTH: 249
<212> TYPE: PRT
<213> ORGANISM: Artificial Sequence
<220> FEATURE:
<223> OTHER INFORMATION: single chain fv 11A1

<400> SEQUENCE: 50

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Phe
            20                  25                  30
```

Ala Met His Trp Val Arg Gln Ile Pro Gly Lys Gly Leu Glu Trp Leu
            35                  40                  45

Ser Gly Leu Arg His Asp Gly Ser Thr Ala Tyr Tyr Ala Gly Ser Val
 50                  55                  60

Lys Gly Arg Phe Thr Ile Ser Arg Asp Asn Arg Asn Thr Val Tyr
 65                  70                  75                  80

Leu Gln Met Asn Ser Leu Arg Ala Glu Asp Thr Ala Thr Tyr Tyr Cys
                85                  90                  95

Val Thr Gly Ser Gly Ser Ser Gly Pro His Ala Phe Pro Val Trp Gly
            100                 105                 110

Lys Gly Thr Leu Val Thr Val Ser Gly Gly Gly Ser Gly Gly
            115                 120                 125

Gly Gly Ser Gly Gly Gly Ser Ala Leu Ser Tyr Val Leu Thr Gln
            130                 135                 140

Pro Pro Ser Ala Ser Gly Thr Pro Gly Gln Arg Val Thr Ile Ser Cys
145                 150                 155                 160

Ser Gly Ser Asn Ser Asn Ile Gly Thr Tyr Thr Val Asn Trp Phe Gln
                165                 170                 175

Gln Leu Pro Gly Thr Ala Pro Lys Leu Leu Ile Tyr Ser Asn Asn Gln
            180                 185                 190

Arg Pro Ser Gly Val Pro Asp Arg Phe Ser Gly Ser Lys Ser Gly Thr
            195                 200                 205

Ser Ala Ser Leu Ala Ile Ser Gly Leu Gln Ser Glu Asp Glu Ala Asp
210                 215                 220

Tyr Tyr Cys Ala Ala Trp Asp Asp Ser Leu Asn Gly Pro Val Phe Gly
225                 230                 235                 240

Gly Gly Thr Lys Val Thr Val Leu Gly
            245

<210> SEQ ID NO 51
<211> LENGTH: 251
<212> TYPE: PRT
<213> ORGANISM: Artificial Sequence
<220> FEATURE:
<223> OTHER INFORMATION: single chain fv 7A6

<400> SEQUENCE: 51

Glu Val Gln Leu Val Gln Ser Gly Ala Glu Val Lys Lys Pro Gly Glu
1               5                   10                  15

Ser Leu Thr Ile Ser Cys Lys Gly Ser Gly Tyr Asn Phe Phe Asn Tyr
            20                  25                  30

Trp Ile Gly Trp Val Arg Gln Met Pro Gly Lys Gly Leu Glu Trp Met
            35                  40                  45

Gly Ile Ile Tyr Pro Thr Asp Ser Asp Thr Arg Tyr Ser Pro Ser Phe
 50                  55                  60

Gln Gly Gln Val Thr Ile Ser Val Asp Lys Ser Ile Ser Thr Ala Tyr
 65                  70                  75                  80

Leu Gln Trp Ser Ser Leu Lys Ala Ser Asp Thr Ala Met Tyr Tyr Cys
                85                  90                  95

Ala Arg Ser Ile Arg Tyr Cys Pro Gly Gly Arg Cys Tyr Ser Gly Tyr
            100                 105                 110

Tyr Gly Met Asp Val Trp Gly Gln Gly Thr Leu Val Thr Val Ser Ser
            115                 120                 125

Gly Gly Gly Gly Ser Gly Gly Gly Gly Ser Gly Gly Gly Gly Ser Ser
            130                 135                 140

```
Glu Leu Thr Gln Asp Pro Ala Val Ser Val Ala Leu Gly Gln Thr Val
145                 150                 155                 160

Arg Ile Thr Cys Gln Gly Asp Ser Leu Arg Ser Tyr Tyr Thr Asn Trp
                165                 170                 175

Phe Gln Gln Lys Pro Gly Gln Ala Pro Leu Leu Val Val Tyr Ala Lys
            180                 185                 190

Asn Lys Arg Pro Ser Gly Ile Pro Asp Arg Phe Ser Gly Ser Ser Ser
        195                 200                 205

Gly Asn Thr Ala Ser Leu Thr Ile Thr Gly Ala Gln Ala Glu Asp Glu
    210                 215                 220

Ala Asp Tyr Tyr Cys Asn Ser Arg Asp Ser Ser Gly Asn His Val Val
225                 230                 235                 240

Phe Gly Gly Gly Thr Lys Leu Thr Val Leu Gly
                245                 250

<210> SEQ ID NO 52
<211> LENGTH: 5
<212> TYPE: PRT
<213> ORGANISM: Artificial Sequence
<220> FEATURE:
<223> OTHER INFORMATION: CDR

<400> SEQUENCE: 52

Ser Tyr Trp Met His
1               5

<210> SEQ ID NO 53
<211> LENGTH: 17
<212> TYPE: PRT
<213> ORGANISM: Artificial Sequece
<220> FEATURE:
<223> OTHER INFORMATION: CDR

<400> SEQUENCE: 53

Glu Ile Asn Pro Ser Asn Gly Arg Thr Asn Tyr Asn Glu Lys Phe Lys
1               5                   10                  15

Arg

<210> SEQ ID NO 54
<211> LENGTH: 15
<212> TYPE: PRT
<213> ORGANISM: Artificial Sequence
<220> FEATURE:
<223> OTHER INFORMATION: CDR

<400> SEQUENCE: 54

Gly Arg Pro Asp Tyr Tyr Gly Ser Ser Lys Trp Tyr Phe Asp Val
1               5                   10                  15

<210> SEQ ID NO 55
<211> LENGTH: 16
<212> TYPE: PRT
<213> ORGANISM: Artificial Sequence
<220> FEATURE:
<223> OTHER INFORMATION: CDR

<400> SEQUENCE: 55

Arg Ser Ser Gln Ser Ile Val His Ser Asn Val Asn Thr Tyr Leu Glu
1               5                   10                  15

<210> SEQ ID NO 56
<211> LENGTH: 7
<212> TYPE: PRT
<213> ORGANISM: Artificial Sequence
```

```
<220> FEATURE:
<223> OTHER INFORMATION: CDR

<400> SEQUENCE: 56

Lys Val Ser Asn Arg Phe Ser
1               5

<210> SEQ ID NO 57
<211> LENGTH: 9
<212> TYPE: PRT
<213> ORGANISM: Artificial Sequence
<220> FEATURE:
<223> OTHER INFORMATION: CDR

<400> SEQUENCE: 57

Phe Gln Gly Ser His Val Pro Pro Thr
1               5

<210> SEQ ID NO 58
<211> LENGTH: 123
<212> TYPE: PRT
<213> ORGANISM: Artificial Sequence
<220> FEATURE:
<223> OTHER INFORMATION: heavy chain immunoglobulin variable region

<400> SEQUENCE: 58

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Ser Asn Gly Arg Thr Asn Tyr Asn Gln Lys Phe
    50                  55                  60

Gln Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Phe
                85                  90                  95

Ala Arg Gly Arg Pro Asp Tyr Tyr Gly Ser Ser Lys Trp Tyr Phe Asp
            100                 105                 110

Val Trp Gly Gln Gly Thr Thr Val Thr Val Ser
        115                 120

<210> SEQ ID NO 59
<211> LENGTH: 118
<212> TYPE: PRT
<213> ORGANISM: Artificial Sequence
<220> FEATURE:
<223> OTHER INFORMATION: heavy chain immunoglobulin variable region

<400> SEQUENCE: 59

Gln Val Gln Phe Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Leu Met His Trp Ile Lys Gln Arg Pro Gly Arg Gly Leu Glu Trp Ile
        35                  40                  45

Gly Arg Ile Asp Pro Asn Asn Val Val Thr Lys Phe Asn Glu Lys Phe
    50                  55                  60

Lys Ser Lys Ala Thr Leu Thr Val Asp Lys Pro Ser Ser Thr Ala Tyr
65                  70                  75                  80
```

```
Met Glu Leu Ser Ser Leu Thr Ser Glu Asp Ser Ala Val Tyr Tyr Cys
            85                  90                  95

Ala Arg Tyr Ala Tyr Cys Arg Pro Met Asp Tyr Trp Gly Gln Gly Thr
            100                 105                 110

Thr Val Thr Val Ser Ser
        115

<210> SEQ ID NO 60
<211> LENGTH: 123
<212> TYPE: PRT
<213> ORGANISM: Artificial Sequence
<220> FEATURE:
<223> OTHER INFORMATION: heavy chain immunoglobulin variable region

<400> SEQUENCE: 60

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Ser Asn Gly Arg Thr Asn Tyr Asn Glu Lys Phe
    50                  55                  60

Lys Arg Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Phe
            85                  90                  95

Ala Arg Gly Arg Pro Asp Tyr Tyr Gly Ser Ser Lys Trp Tyr Phe Asp
            100                 105                 110

Val Trp Gly Ala Gly Thr Thr Val Thr Val Ser
        115                 120

<210> SEQ ID NO 61
<211> LENGTH: 120
<212> TYPE: PRT
<213> ORGANISM: Artificial Sequence
<220> FEATURE:
<223> OTHER INFORMATION: heavy chain immunoglobulin variable region

<400> SEQUENCE: 61

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ser Phe
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Gly Thr His Tyr Asn Glu Lys Phe
    50                  55                  60

Lys Gly Lys Ala Thr Phe Thr Ala Asp Lys Ser Ser Asn Thr Ala Tyr
65                  70                  75                  80

Met Gln Leu Ser Ser Leu Thr Ser Glu Asp Ser Ala Val Tyr Tyr Cys
            85                  90                  95

Ala Arg Gly His Ser Tyr Tyr Phe Tyr Asp Gly Asp Tyr Trp Gly Gln
            100                 105                 110

Gly Thr Ser Val Thr Val Ser Ser
        115                 120

<210> SEQ ID NO 62
<211> LENGTH: 120
```

```
<212> TYPE: PRT
<213> ORGANISM: Artificial Sequence
<220> FEATURE:
<223> OTHER INFORMATION: heavy chain immunoglobulin variable region

<400> SEQUENCE: 62

Gln Val Gln Leu Gln Gln Pro Gly Ser Val Leu Val Arg Pro Gly Ala
1               5                   10                  15

Ser Val Lys Leu Ser Cys Lys Ala Ser Gly Tyr Thr Phe Thr Ser Ser
            20                  25                  30

Trp Ile His Trp Ala Lys Gln Arg Pro Gly Gln Gly Leu Glu Trp Ile
        35                  40                  45

Gly Glu Ile His Pro Asn Ser Gly Asn Thr Asn Tyr Asn Glu Lys Phe
    50                  55                  60

Lys Gly Lys Ala Thr Leu Thr Val Asp Thr Ser Ser Thr Ala Tyr
65                  70                  75                  80

Val Asp Leu Ser Ser Leu Thr Ser Glu Asp Ser Ala Val Tyr Tyr Cys
                85                  90                  95

Ala Arg Trp Arg Tyr Gly Ser Pro Tyr Tyr Phe Asp Tyr Trp Gly Gln
                100                 105                 110

Gly Thr Thr Leu Thr Val Ser Ser
            115                 120

<210> SEQ ID NO 63
<211> LENGTH: 120
<212> TYPE: PRT
<213> ORGANISM: Artificial Sequence
<220> FEATURE:
<223> OTHER INFORMATION: heavy chain immunoglobulin variable region

<400> SEQUENCE: 63

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Arg Gly Leu Glu Trp Ile
        35                  40                  45

Gly Arg Ile Asp Pro Asn Ser Gly Gly Thr Lys Tyr Asn Glu Lys Phe
    50                  55                  60

Lys Ser Lys Ala Thr Leu Thr Val Asp Lys Pro Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Asp Tyr Tyr Gly Ser Ser Tyr Phe Asp Tyr Trp Gly Gln
                100                 105                 110

Gly Thr Thr Leu Thr Val Ser Ser
            115                 120

<210> SEQ ID NO 64
<211> LENGTH: 123
<212> TYPE: PRT
<213> ORGANISM: Artificial Sequence
<220> FEATURE:
<223> OTHER INFORMATION: heavy chain immunoglobulin variable region

<400> SEQUENCE: 64

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Ser Tyr
            20                  25                  30
```

Trp Met His Trp Val Lys Gln Arg Pro Gly Gln Gly Leu Glu Trp Ile
            35                  40                  45

Gly Glu Ile Asn Pro Ser Asn Gly Arg Thr Asn Tyr Asn Gln Lys Phe
 50                  55                  60

Gln Gly Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Tyr Phe
                85                  90                  95

Ala Arg Gly Arg Pro Asp Tyr Tyr Gly Ser Ser Lys Trp Tyr Phe Asp
            100                 105                 110

Val Trp Gly Gln Gly Thr Thr Val Thr Val Ser
            115                 120

<210> SEQ ID NO 65
<211> LENGTH: 124
<212> TYPE: PRT
<213> ORGANISM: Artificial Sequence
<220> FEATURE:
<223> OTHER INFORMATION: heavy chain immunoglobulin variable region

<400> SEQUENCE: 65

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
            35                  40                  45

Gly Glu Ile Asn Pro Ser Asn Gly Arg Thr Asn Tyr Asn Glu Lys Phe
 50                  55                  60

Lys Arg Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Tyr Phe
                85                  90                  95

Ala Arg Gly Arg Pro Asp Tyr Tyr Gly Ser Ser Lys Trp Tyr Phe Asp
            100                 105                 110

Val Trp Gly Ala Gly Thr Thr Val Thr Val Ser Ser
            115                 120

<210> SEQ ID NO 66
<211> LENGTH: 124
<212> TYPE: PRT
<213> ORGANISM: Artificial Sequence
<220> FEATURE:
<223> OTHER INFORMATION: heavy chain immunoglobulin variable region

<400> SEQUENCE: 66

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
            35                  40                  45

Gly Glu Ile Asn Pro Ser Asn Gly Arg Thr Asn Tyr Asn Gln Lys Phe
 50                  55                  60

Gln Gly Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Tyr Phe
                85                  90                  95

-continued

Ala Arg Gly Arg Pro Asp Tyr Tyr Gly Ser Ser Lys Trp Tyr Phe Asp
            100                 105                 110

Val Trp Gly Gln Gly Thr Thr Val Thr Val Ser Ser
            115                 120

<210> SEQ ID NO 67
<211> LENGTH: 120
<212> TYPE: PRT
<213> ORGANISM: Artificial Sequence
<220> FEATURE:
<223> OTHER INFORMATION: heavy chain immunoglobulin variable region

<400> SEQUENCE: 67

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Arg Gly Leu Glu Trp Ile
        35                  40                  45

Gly Arg Ile Asp Pro Asn Ser Gly Gly Thr Lys Tyr Asn Glu Lys Phe
    50                  55                  60

Lys Ser Lys Ala Thr Leu Thr Val Asp Lys Pro Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Asp Tyr Tyr Gly Ser Ser Tyr Phe Asp Tyr Trp Gly Gln
            100                 105                 110

Gly Thr Thr Val Thr Val Ser Ser
        115                 120

<210> SEQ ID NO 68
<211> LENGTH: 117
<212> TYPE: PRT
<213> ORGANISM: Artificial Sequence
<220> FEATURE:
<223> OTHER INFORMATION: heavy chain immunoglobulin variable region

<400> SEQUENCE: 68

Gln Ile Gln Leu Gln Gln Ser Gly Pro Glu Leu Val Arg Pro Gly Ala
1               5                   10                  15

Ser Val Lys Ile Ser Cys Lys Ala Ser Gly Tyr Thr Phe Thr Asp Tyr
            20                  25                  30

Tyr Ile His Trp Val Lys Gln Arg Pro Gly Glu Gly Leu Glu Trp Ile
        35                  40                  45

Gly Trp Ile Tyr Pro Gly Ser Gly Asn Thr Lys Tyr Asn Glu Lys Phe
    50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Gly Lys Phe Ala Met Asp Tyr Trp Gly Gln Gly Thr Ser
            100                 105                 110

Val Thr Val Ser Ser
        115

<210> SEQ ID NO 69
<211> LENGTH: 124
<212> TYPE: PRT
<213> ORGANISM: Artificial Sequence

```
<220> FEATURE:
<223> OTHER INFORMATION: heavy chain immunoglobulin variable region

<400> SEQUENCE: 69

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Glu Ile Asn Pro Ser Asn Gly Arg Thr Asn Tyr Asn Glu Lys Phe
        50                  55                  60

Lys Arg Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Phe
                85                  90                  95

Ala Arg Gly Arg Pro Asp Tyr Tyr Gly Ser Ser Lys Tyr Phe Asp
            100                 105                 110

Val Trp Gly Ala Gly Thr Thr Val Thr Val Ser Ser
        115                 120

<210> SEQ ID NO 70
<211> LENGTH: 120
<212> TYPE: PRT
<213> ORGANISM: Artificial Sequence
<220> FEATURE:
<223> OTHER INFORMATION: heavy chain immunoglobulin variable region

<400> SEQUENCE: 70

Gln Ile Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
                20                  25                  30

Tyr Ile Asn Trp Met Lys Gln Lys Pro Gly Gln Gly Leu Glu Trp Ile
            35                  40                  45

Gly Trp Ile Asp Pro Gly Ser Gly Asn Thr Lys Tyr Asn Glu Lys Phe
        50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Thr Ala Val Tyr Phe Cys
                85                  90                  95

Ala Arg Glu Lys Thr Thr Tyr Tyr Tyr Ala Met Asp Tyr Trp Gly Gln
            100                 105                 110

Gly Thr Ser Val Thr Val Ser Ala
        115                 120

<210> SEQ ID NO 71
<211> LENGTH: 115
<212> TYPE: PRT
<213> ORGANISM: Artificial Sequence
<220> FEATURE:
<223> OTHER INFORMATION: heavy chain immunoglobulin variable region

<400> SEQUENCE: 71

Val Gln Leu Gln Gln Ser Gly Ala Glu Leu Met Lys Pro Gly Ala Ser
1               5                   10                  15

Val Lys Ile Ser Cys Lys Ala Ser Gly Tyr Thr Phe Ser Asp Tyr Trp
                20                  25                  30

Ile Glu Trp Val Lys Gln Arg Pro Gly His Gly Leu Glu Trp Ile Gly
```

```
                     35                  40                  45
Glu Ile Leu Pro Gly Ser Gly Ser Thr Asn Tyr His Glu Arg Phe Lys
 50                  55                  60

Gly Lys Ala Thr Phe Thr Ala Asp Thr Ser Ser Thr Ala Tyr Met
 65                  70                  75                  80

Gln Leu Asn Ser Leu Thr Ser Glu Asp Ser Gly Val Tyr Tyr Cys Leu
                     85                  90                  95

His Gly Asn Tyr Asp Phe Asp Gly Trp Gly Gln Gly Thr Thr Leu Thr
                    100                 105                 110

Val Ser Ser
        115

<210> SEQ ID NO 72
<211> LENGTH: 120
<212> TYPE: PRT
<213> ORGANISM: Artificial Sequence
<220> FEATURE:
<223> OTHER INFORMATION: heavy chain immunoglobulin variable region

<400> SEQUENCE: 72

Gln Val Gln Leu Leu Glu Ser Gly Ala Glu Leu Met Lys Pro Gly Ala
  1               5                  10                  15

Ser Val Lys Ile Ser Cys Lys Ala Thr Gly Tyr Thr Phe Ser Ser Phe
                 20                  25                  30

Trp Ile Glu Trp Val Lys Gln Arg Pro Gly His Gly Leu Glu Trp Ile
             35                  40                  45

Gly Glu Ile Leu Pro Gly Ser Gly Gly Thr His Tyr Asn Glu Lys Phe
 50                  55                  60

Lys Gly Lys Ala Thr Phe Thr Ala Asp Lys Ser Ser Asn Thr Ala Tyr
 65                  70                  75                  80

Met Gln Leu Ser Ser Leu Thr Ser Glu Asp Ser Ala Val Tyr Tyr Cys
                 85                  90                  95

Ala Arg Gly His Ser Tyr Tyr Phe Tyr Asp Gly Asp Tyr Trp Gly Gln
                100                 105                 110

Gly Thr Ser Val Thr Val Ser Ser
        115                 120

<210> SEQ ID NO 73
<211> LENGTH: 113
<212> TYPE: PRT
<213> ORGANISM: Artificial Sequence
<220> FEATURE:
<223> OTHER INFORMATION: light  chain immunoglobulin variable region

<400> SEQUENCE: 73

Asp Val Leu Met Thr Gln Ile Pro Val Ser Leu Pro Val Ser Leu Gly
  1               5                  10                  15

Asp Gln Ala Ser Ile Ser Cys Arg Ser Ser Gln Ile Ile Val His Asn
                 20                  25                  30

Asn Gly Asn Thr Tyr Leu Glu Trp Tyr Leu Gln Lys Pro Gly Gln Ser
             35                  40                  45

Pro Gln Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Phe Thr Phe Gly Ser Gly Thr Lys Leu Glu Ile Lys
```

```
                100                 105                 110

Arg

<210> SEQ ID NO 74
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 74

Asp Val Leu Met Thr Gln Thr Pro Leu Ser Leu Pro Val Ser Leu Gly
1               5                   10                  15

Asp Pro Ala Ser Ile Ser Cys Arg Ser Gln Ser Ile Val His Ser
            20                  25                  30

Asn Val Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Arg Ile
65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
            100                 105                 110

Arg

<210> SEQ ID NO 75
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 75

Asp Val Leu Met Thr Gln Thr Pro Leu Ser Leu Pro Val Ser Leu Gly
1               5                   10                  15

Asp Pro Ala Ser Ile Ser Cys Arg Ser Gln Ser Ile Val His Ser
            20                  25                  30

Asn Val Asn Thr Tyr Leu Glu Trp Tyr Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Arg Ile
65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
            100                 105                 110

Arg

<210> SEQ ID NO 76
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 76
```

```
Asp Val Leu Met Thr Gln Thr Pro Leu Ser Leu Pro Val Ser Leu Gly
1               5                   10                  15

Asp Pro Ala Ser Ile Ser Cys Arg Ser Ser Gln Ser Ile Val His Ser
            20                  25                  30

Asn Val Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Arg Ile
65              70                  75                  80

Ser Arg Val Glu Ala Glu Asp Leu Gly Ile Tyr Tyr Cys Phe Gln Gly
            85                  90                  95

Ser His Val Pro Pro Thr Phe Gly Gly Gly Thr Lys Leu Glu Ile Lys
            100                 105                 110

Arg
```

<210> SEQ ID NO 77
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 77

```
Asp Val Leu Met Thr Gln Thr Pro Leu Ser Leu Pro Val Ser Leu Gly
1               5                   10                  15

Asp Pro Ala Ser Ile Ser Cys Arg Ser Ser Gln Ser Ile Val His Ser
            20                  25                  30

Asn Val Asn Thr Tyr Leu Glu Trp Tyr Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Arg Ile
65              70                  75                  80

Ser Arg Val Glu Ala Glu Asp Leu Gly Ile Tyr Tyr Cys Phe Gln Gly
            85                  90                  95

Ser His Val Pro Pro Thr Phe Gly Gly Gly Thr Lys Leu Glu Ile Lys
            100                 105                 110

Arg
```

<210> SEQ ID NO 78
<211> LENGTH: 113
<212> TYPE: PRT
<213> ORGANISM: Artificial Sequence
<220> FEATURE:
<223> OTHER INFORMATION: light chain immunoglobulin variable region
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (101)..(101)
<223> OTHER INFORMATION: Xaa can be any naturally occurring amino acid

<400> SEQUENCE: 78

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Xaa Ile Val His Ser
            20                  25                  30
```

```
Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Xaa Thr Phe Gly Gly Gly Thr Lys Leu Glu Ile Lys
                100                 105                 110

Arg

<210> SEQ ID NO 79
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 79

Asp Val Val Met Thr Gln Thr Pro Leu Ser Leu Pro Val Ser Leu Gly
  1                5                  10                  15

Asp Pro Ala Ser Ile Ser Cys Arg Ser Ser Gln Ser Ile Val His Ser
                 20                  25                  30

Asn Val Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
 50                  55                  60

Asp Arg Phe Ser Gly Ser Gly Ala Gly Thr Asp Phe Thr Leu Arg Ile
 65                  70                  75                  80

Ser Arg Val Glu Ala Glu Asp Leu Gly Ile Tyr Tyr Cys Phe Gln Gly
                 85                  90                  95

Ser His Val Pro Pro Thr Phe Gly Gly Gly Thr Lys Leu Glu Ile Lys
                100                 105                 110

Arg

<210> SEQ ID NO 80
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 80

Asp Val Val Met Thr Gln Thr Pro Leu Ser Leu Pro Val Ser Leu Gly
  1                5                  10                  15

Asp Pro Ala Ser Ile Ser Cys Arg Ser Ser Gln Ser Ile Val His Ser
                 20                  25                  30

Asn Val Asn Thr Tyr Leu Glu Trp Tyr Leu Gln Lys Pro Gly Gln Ser
            35                  40                  45

Pro Arg Leu Leu Ile Tyr Lys Val Ser Asn Arg Phe Ser Gly Val Pro
 50                  55                  60

Asp Arg Phe Ser Gly Ser Gly Ala Gly Thr Asp Phe Thr Leu Arg Ile
 65                  70                  75                  80

Ser Arg Val Glu Ala Glu Asp Leu Gly Ile Tyr Tyr Cys Phe Gln Gly
                 85                  90                  95

Ser His Val Pro Pro Thr Phe Gly Gly Gly Thr Lys Leu Glu Ile Lys
                100                 105                 110
```

<210> SEQ ID NO 81
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 81

```
Asp Val Leu Met Thr Gln Thr Pro Leu Ser Leu Pro Val Ser Leu Gly
1               5                   10                  15
Asp Pro Ala Ser Ile Ser Cys Arg Ser Gln Ser Ile Val His Ser
            20                  25                  30
Asn Val Asn Thr Tyr Leu Glu Trp Tyr Leu Gln Lys Pro Gly Gln Ser
        35                  40                  45
Pro Arg Leu Leu Ile Tyr Lys Val Ser Asn Arg Phe Ser Gly Val Pro
    50                  55                  60
Asp Arg Phe Ser Gly Ser Gly Ala Gly Thr Asp Phe Thr Leu Arg Ile
65                  70                  75                  80
Ser Arg Val Glu Ala Glu Asp Leu Gly Ile Tyr Tyr Cys Phe Gln Gly
                85                  90                  95
Ser His Val Pro Pro Thr Phe Gly Gly Gly Thr Lys Leu Glu Ile Lys
                100                 105                 110
Arg
```

<210> SEQ ID NO 82
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 82

```
Asp Val Leu Met Thr Gln Ile Pro Val Ser Leu Pro Val Ser Leu Gly
1               5                   10                  15
Asp Gln Ala Ser Ile Ser Cys Arg Ser Gln Ile Ile Val His Asn
            20                  25                  30
Asn Gly Asn Thr Tyr Leu Glu Trp Tyr Leu Gln Lys Pro Gly Gln Ser
        35                  40                  45
Pro Gln Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Tyr Cys Phe Gln Gly
                85                  90                  95
Ser His Val Pro Phe Thr Phe Gly Ser Gly Thr Lys Leu Glu Ile Lys
                100                 105                 110
Arg
```

<210> SEQ ID NO 83
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 83

```
Asp Val Leu Met Thr Gln Thr Pro Leu Ser Leu Pro Val Ser Leu Gly
```

```
                1               5                   10                  15
Asp Gln Ala Ser Ile Ser Cys Arg Phe Ser Gln Ser Ile Val His Ser
                20                  25                  30

Asn Gly Asn Thr Tyr Leu Glu Trp Tyr Leu Gln Lys Ser Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Arg Thr Phe Gly Gly Gly Thr Lys Leu Glu Ile Lys
                100                 105                 110

Arg
```

<210> SEQ ID NO 84
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 84

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
                20                  25                  30

Asn Val Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
                100                 105                 110

Arg
```

<210> SEQ ID NO 85
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 85

```
Asp Val Val Met Thr Gln Thr Pro Leu Ser Leu Pro Val Ser Leu Gly
1               5                   10                  15

Asp Pro Ala Ser Ile Ser Cys Arg Ser Ser Gln Ser Ile Val His Ser
                20                  25                  30

Asn Val Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ala Gly Thr Asp Phe Thr Leu Arg Ile
65                  70                  75                  80
```

-continued

```
Ser Arg Val Glu Ala Glu Asp Leu Gly Ile Tyr Tyr Cys Phe Gln Gly
            85                  90                  95

Ser His Val Pro Pro Thr Phe Gly Gly Gly Thr Lys Leu Glu Ile Lys
            100                 105                 110

Arg

<210> SEQ ID NO 86
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 86

Glu Leu Val Met Thr Gln Thr Pro Leu Ser Leu Pro Val Ser Leu Gly
1               5                   10                  15

Asp Gln Ala Ser Ile Ser Cys Arg Ser Gln Thr Ile Val His Ser
            20                  25                  30

Asn Gly Asp Thr Tyr Leu Asp Trp Phe Leu Gln Lys Pro Gly Gln Ser
            35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
            85                  90                  95

Ser His Val Pro Pro Thr Phe Gly Gly Gly Thr Lys Leu Glu Ile Lys
            100                 105                 110

Arg

<210> SEQ ID NO 87
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 87

Asp Val Leu Met Thr Gln Thr Pro Leu Ser Leu Pro Val Ser Leu Gly
1               5                   10                  15

Asp Pro Ala Ser Ile Ser Cys Arg Ser Gln Ser Ile Val His Ser
            20                  25                  30

Asn Val Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Arg Ile
65                  70                  75                  80

Ser Arg Val Glu Ala Glu Asp Leu Gly Ile Tyr Tyr Cys Phe Gln Gly
            85                  90                  95

Ser His Val Pro Pro Thr Phe Gly Gly Gly Thr Lys Leu Glu Ile Lys
            100                 105                 110

Arg

<210> SEQ ID NO 88
<211> LENGTH: 113
<212> TYPE: PRT
<213> ORGANISM: Artificial Sequence
<220> FEATURE:
```

<223> OTHER INFORMATION: light chain immunoglobulin variable region

<400> SEQUENCE: 88

```
Asp Val Val Met Thr Gln Thr Pro Leu Ser Leu Pro Val Ser Leu Gly
1               5                   10                  15
Asp Pro Ala Ser Ile Ser Cys Arg Ser Ser Gln Ser Ile Val His Ser
            20                  25                  30
Asn Val Asn Thr Tyr Leu Glu Trp Tyr Leu Gln Lys Pro Gly Gln Ser
        35                  40                  45
Pro Arg Leu Leu Ile Tyr Lys Val Ser Asn Arg Phe Ser Gly Val Pro
    50                  55                  60
Asp Arg Phe Ser Gly Ser Gly Ala Gly Thr Asp Phe Thr Leu Arg Ile
65                  70                  75                  80
Ser Arg Val Glu Ala Glu Asp Leu Gly Ile Tyr Tyr Cys Phe Gln Gly
                85                  90                  95
Ser His Val Pro Pro Thr Phe Gly Gly Gly Thr Lys Leu Glu Ile Lys
            100                 105                 110
Arg
```

<210> SEQ ID NO 89
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 89

```
Asp Val Leu Met Thr Gln Thr Pro Val Ser Leu Ser Val Ser Leu Gly
1               5                   10                  15
Asp Gln Ala Ser Ile Ser Cys Arg Ser Ser Gln Ser Ile Val His Ser
            20                  25                  30
Thr Gly Asn Thr Tyr Leu Glu Trp Tyr Leu Gln Lys Pro Gly Gln Ser
        35                  40                  45
Pro Lys Leu Leu Ile Tyr Lys Ile Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Tyr Cys Phe Gln Ala
                85                  90                  95
Ser His Ala Pro Arg Thr Phe Gly Gly Gly Thr Lys Leu Glu Ile Lys
            100                 105                 110
Arg
```

<210> SEQ ID NO 90
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 90

```
Asp Val Leu Met Thr Gln Thr Pro Leu Ser Leu Pro Val Ser Leu Gly
1               5                   10                  15
Asp Gln Ala Ser Ile Ser Cys Lys Ser Ser Gln Ser Ile Val His Ser
            20                  25                  30
Ser Gly Asn Thr Tyr Phe Glu Trp Tyr Leu Gln Lys Pro Gly Gln Ser
        35                  40                  45
Pro Lys Leu Leu Ile Tyr Lys Val Ser Asn Arg Phe Ser Gly Val Pro
```

```
                50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Ile Pro Phe Thr Phe Gly Ser Gly Thr Lys Leu Glu Ile Lys
                100                 105                 110

Arg

<210> SEQ ID NO 91
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 91

Asp Ile Glu Leu Thr Gln Thr Pro Leu Ser Leu Pro Val Ser Leu Gly
 1               5                  10                  15

Asp Gln Ala Ser Ile Ser Cys Arg Ser Ser Gln Ser Ile Val His Ser
                 20                  25                  30

Asn Gly Asn Thr Tyr Leu Glu Trp Tyr Leu Gln Lys Pro Gly Gln Ser
             35                  40                  45

Pro Lys Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Tyr Thr Phe Gly Gly Gly Thr Lys Leu Glu Ile Lys
                100                 105                 110

Arg

<210> SEQ ID NO 92
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 92

Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Ser Ile Val His Ser
                 20                  25                  30

Asn Val Asn Thr Tyr Leu Glu Trp Tyr Leu Gln Lys Pro Gly Gln Ser
             35                  40                  45

Pro Lys Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Arg Ile
 65                  70                  75                  80

Ser Arg Val Glu Ala Glu Asp Leu Gly Ile Tyr Tyr Cys Phe Gln Gly
                 85                  90                  95

Ser His Val Pro Pro Thr Phe Gly Gly Gly Thr Lys Leu Glu Ile Lys
                100                 105                 110

Arg
```

```
<210> SEQ ID NO 93
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 93

Asp Val Val Met Thr Gln Thr Pro Leu Ser Leu Pro Val Ser Leu Gly
1               5                   10                  15

Asp Pro Ala Ser Ile Ser Cys Arg Ser Ser Gln Ser Ile Val His Ser
            20                  25                  30

Asn Val Asn Thr Tyr Leu Glu Trp Tyr Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Arg Ile
65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
            100                 105                 110

Arg

<210> SEQ ID NO 94
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 94

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Val Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
            100                 105                 110

Arg

<210> SEQ ID NO 95
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 95

Asp Val Val Met Thr Gln Thr Pro Leu Ser Leu Pro Val Ser Leu Gly
1               5                   10                  15

Asp Pro Ala Ser Ile Ser Cys Arg Ser Ser Gln Ser Ile Val His Ser
            20                  25                  30
```

```
Asn Val Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
 50                  55                  60

Asp Arg Phe Ser Gly Ser Gly Ala Gly Thr Asp Phe Thr Leu Arg Ile
 65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
                100                 105                 110

Arg
```

<210> SEQ ID NO 96
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 96

```
Asp Val Leu Met Thr Gln Thr Pro Leu Ser Leu Pro Val Ser Leu Gly
 1               5                  10                  15

Asp Gln Ala Ser Ile Ser Cys Arg Ser Asn Gln Thr Ile Leu Leu Ser
                20                  25                  30

Asp Gly Asp Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
                100                 105                 110

Arg
```

<210> SEQ ID NO 97
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 97

```
Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Thr Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Thr Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                85                  90                  95

Thr His Ala Pro Tyr Thr Phe Gly Gly Gly Thr Lys Leu Glu Ile Lys
```

Arg

<210> SEQ ID NO 98
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 98

Asp Val Leu Met Thr Gln Thr Pro Leu Ser Leu Pro Val Ser Leu Gly
1               5                   10                  15

Asp Gln Ala Ser Ile Ser Cys Arg Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Ser Ile Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Gln Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
                100                 105                 110

Arg

<210> SEQ ID NO 99
<211> LENGTH: 14
<212> TYPE: DNA
<213> ORGANISM: Artificial Sequence
<220> FEATURE:
<223> OTHER INFORMATION: primer

<400> SEQUENCE: 99
ctccgcttcc tttc                                                         14

<210> SEQ ID NO 100
<211> LENGTH: 18
<212> TYPE: DNA
<213> ORGANISM: Artificial Sequence
<220> FEATURE:
<223> OTHER INFORMATION: anti-sense

<400> SEQUENCE: 100
atctctccgc ttcctttc                                                     18

<210> SEQ ID NO 101
<211> LENGTH: 18
<212> TYPE: DNA
<213> ORGANISM: Artificial Sequence
<220> FEATURE:
<223> OTHER INFORMATION: anti-sense

<400> SEQUENCE: 101
atctctccgc ttcctttc                                                     18

<210> SEQ ID NO 102
<211> LENGTH: 19
<212> TYPE: DNA
<213> ORGANISM: Artificial Sequence
<220> FEATURE:
<223> OTHER INFORMATION: primer -continued

<400> SEQUENCE: 102
aggagctcga ggcgttcag                                                       19

<210> SEQ ID NO 103
<211> LENGTH: 22
<212> TYPE: DNA
<213> ORGANISM: Artificial Sequence
<220> FEATURE:
<223> OTHER INFORMATION: primer

<400> SEQUENCE: 103
gtcttgggtg ggtagagcaa tc                                                   22

<210> SEQ ID NO 104
<211> LENGTH: 21
<212> TYPE: DNA
<213> ORGANISM: Artificial Sequence
<220> FEATURE:
<223> OTHER INFORMATION: primer

<400> SEQUENCE: 104
aggccaaacg tcaccgtccc c                                                    21

<210> SEQ ID NO 105
<211> LENGTH: 109
<212> TYPE: PRT
<213> ORGANISM: Artificial Sequence
<220> FEATURE:
<223> OTHER INFORMATION: A12 immunoglobulin light chain variable region

<400> SEQUENCE: 105

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Thr Trp Tyr Gln Gln Lys Pro Gly Gln Ala Pro Ile Leu Val Ile Tyr
        35                  40                  45

Gly Glu Asn Lys Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Lys Ser Arg Asp Gly Ser Gly Gln His
                85                  90                  95

Leu Val Phe Gly Gly Gly Thr Lys Leu Thr Val Leu Gly
            100                 105

<210> SEQ ID NO 106
<211> LENGTH: 11
<212> TYPE: PRT
<213> ORGANISM: Artificial Sequence
<220> FEATURE:
<223> OTHER INFORMATION: CDR-L1

<400> SEQUENCE: 106

Arg Ala Ser Gln Ser Ile Gly Ser Ser Leu His
1               5                   10

<210> SEQ ID NO 107
<211> LENGTH: 7
<212> TYPE: PRT
<213> ORGANISM: Artificial Sequence
<220> FEATURE:
<223> OTHER INFORMATION: CDR-L2'

```
<400> SEQUENCE: 107

Tyr Ala Ser Gln Ser Leu Ser
1               5

<210> SEQ ID NO 108
<211> LENGTH: 9
<212> TYPE: PRT
<213> ORGANISM: Artificial Sequence
<220> FEATURE:
<223> OTHER INFORMATION: CDR-L3

<400> SEQUENCE: 108

His Gln Ser Ser Arg Leu Pro His Thr
1               5

<210> SEQ ID NO 109
<211> LENGTH: 5
<212> TYPE: PRT
<213> ORGANISM: Artificial Sequence
<220> FEATURE:
<223> OTHER INFORMATION: CDR-H1

<400> SEQUENCE: 109

Ser Phe Ala Met His
1               5

<210> SEQ ID NO 110
<211> LENGTH: 10
<212> TYPE: PRT
<213> ORGANISM: Artificial Sequence
<220> FEATURE:
<223> OTHER INFORMATION: CDR-H1 alternate

<400> SEQUENCE: 110

Gly Phe Thr Phe Ser Ser Phe Ala Met His
1               5                   10

<210> SEQ ID NO 111
<211> LENGTH: 16
<212> TYPE: PRT
<213> ORGANISM: Artificial Sequence
<220> FEATURE:
<223> OTHER INFORMATION: CDR-H2

<400> SEQUENCE: 111

Val Ile Asp Thr Arg Gly Ala Thr Tyr Tyr Ala Asp Ser Val Lys Gly
1               5                   10                  15

<210> SEQ ID NO 112
<211> LENGTH: 10
<212> TYPE: PRT
<213> ORGANISM: Artificial Sequence
<220> FEATURE:
<223> OTHER INFORMATION: CDR-H3

<400> SEQUENCE: 112

Leu Gly Asn Phe Tyr Tyr Gly Met Asp Val
1               5                   10
```